(12) United States Patent
Varona et al.

(10) Patent No.: US 10,799,400 B2
(45) Date of Patent: Oct. 13, 2020

(54) ELASTIC CORE COMPOSITE OR ASSEMBLY, AND A SYSTEM AND METHOD FOR MAKING THE ELASTIC COMPOSITE ASSEMBLY

(71) Applicant: DSG TECHNOLOGY HOLDINGS LTD., Kwai Chung (HK)

(72) Inventors: Eugenio Varona, Marietta, GA (US); Andrew Wright, Derbyshire (GB)

(73) Assignee: DSG Technology Holdings Ltd., Kwai Chung, N.T. (HK)

( * ) Notice: Subject to any disclaimer, the term of this patent is extended or adjusted under 35 U.S.C. 154(b) by 627 days.

(21) Appl. No.: 15/360,776

(22) Filed: Nov. 23, 2016

(65) Prior Publication Data

US 2017/0165131 A1 Jun. 15, 2017

Related U.S. Application Data

(60) Provisional application No. 62/259,071, filed on Nov. 24, 2015, provisional application No. 62/301,484, filed on Feb. 29, 2016.

(51) Int. Cl.
*A61F 13/49* (2006.01)
*A61F 13/532* (2006.01)
(Continued)

(52) U.S. Cl.
CPC .. *A61F 13/49017* (2013.01); *A61F 13/49019* (2013.01); *A61F 13/5323* (2013.01);
(Continued)

(58) Field of Classification Search
CPC .......... A61F 13/49017; A61F 13/49019; A61F 2013/49022; A61F 2013/49033
See application file for complete search history.

(56) References Cited

U.S. PATENT DOCUMENTS 4,685,914 A * 8/1987 Holtman ............. A61F 13/4702
604/367
4,891,258 A * 1/1990 Fahrenkrug ........... B32B 37/144
428/138
(Continued)

FOREIGN PATENT DOCUMENTS

EP 0238334 A1 9/1987
EP 0321980 A2 6/1989
(Continued)

OTHER PUBLICATIONS

International Preliminary Report on Patentability issued in PCT Application No. PCT/US2016/063426, dated Jun. 7, 2018; 12 pages.
(Continued)

*Primary Examiner* — Susan S Su
(74) *Attorney, Agent, or Firm* — Alberto Q. Amatong, Jr.; Amatong McCoy LLC

(57) ABSTRACT

Described herein is an elastic core assembly having a base nonwoven layer, a top nonwoven layer, and a plurality of spaced apart elastics sandwiched therebetween. The elastics are secured to one or both layers and form therewith, a plurality of elongated spaces wherein SAP material is deposited. Also described are s system and method of making the elastic core composite or assembly, and a disposable absorbent article incorporating the elastic core assembly.

29 Claims, 36 Drawing Sheets

(51) Int. Cl.
*A61F 13/15* (2006.01)
*A61F 13/53* (2006.01)

(52) U.S. Cl.
CPC .................. *A61F 13/15593* (2013.01); *A61F 2013/530481* (2013.01)

(56) References Cited

U.S. PATENT DOCUMENTS

| | | | |
|---|---|---|---|
| 5,295,987 A * | 3/1994 | Widlund | A61F 13/532 604/385.26 |
| 5,389,095 A | 2/1995 | Suzuki et al. | |
| 5,451,219 A * | 9/1995 | Suzuki | A61F 13/515 604/358 |
| 5,681,300 A * | 10/1997 | Ahr | A61F 13/47218 604/358 |
| 5,681,302 A | 10/1997 | Melbye et al. | |
| 5,728,083 A * | 3/1998 | Cohen | A61F 13/15658 156/296 |
| 6,399,854 B1 | 6/2002 | Vartiainen | |
| 6,403,857 B1 | 6/2002 | Gross et al. | |
| 6,436,081 B1 * | 8/2002 | Wada | A61F 13/4752 604/385.01 |
| 6,520,945 B1 | 2/2003 | Hansson | |
| 6,610,900 B1 | 8/2003 | Tanzer | |
| 7,087,044 B2 | 8/2006 | Ohnishi | |
| 7,361,246 B2 | 4/2008 | Chang et al. | |
| 7,462,172 B2 | 12/2008 | Wright et al. | |
| 7,740,727 B2 | 6/2010 | Chang et al. | |
| 8,148,598 B2 | 4/2012 | Tsang et al. | |
| 8,168,024 B2 | 5/2012 | Chang et al. | |
| 8,235,961 B2 | 8/2012 | Nakaoka et al. | |
| 8,257,332 B2 | 9/2012 | Tsang et al. | |
| 8,474,502 B2 | 7/2013 | Chang et al. | |
| 8,568,377 B2 | 10/2013 | Tsang et al. | |
| 8,685,190 B2 | 4/2014 | Chang et al. | |
| 8,702,671 B2 | 4/2014 | Tsang et al. | |
| 2002/0102392 A1 * | 8/2002 | Fish | A61F 13/5323 428/198 |
| 2003/0139721 A1 | 7/2003 | Melius et al. | |
| 2004/0127874 A1 * | 7/2004 | Nishizawa | A61F 13/15699 604/385.01 |
| 2005/0033254 A1 | 2/2005 | Fell et al. | |
| 2006/0020250 A1 * | 1/2006 | Chester | A61F 13/53747 604/378 |
| 2006/0206073 A1 * | 9/2006 | Crane | A61F 13/5323 604/378 |
| 2006/0206074 A1 | 9/2006 | Bernal et al. | |
| 2007/0088308 A1 | 4/2007 | Ehrnsperger et al. | |
| 2008/0312628 A1 | 12/2008 | Hundorf et al. | |
| 2011/0130736 A1 | 6/2011 | Tsang et al. | |
| 2013/0011601 A1 | 1/2013 | Fenske | |
| 2014/0052089 A1 | 2/2014 | Fenske | |
| 2014/0128831 A1 | 5/2014 | Tsang et al. | |
| 2014/0213997 A1 | 7/2014 | Tsang et al. | |
| 2014/0303582 A1 | 10/2014 | Wright et al. | |
| 2016/0067115 A1 * | 3/2016 | Ishikawa | A61F 13/15593 604/385.29 |

FOREIGN PATENT DOCUMENTS

| | | |
|---|---|---|
| EP | 1116479 A2 | 7/2001 |
| EP | 1627618 A1 | 2/2006 |
| EP | 2730261 A1 | 5/2014 |
| WO | 9908639 A1 | 2/1992 |
| WO | 9534264 A1 | 12/1995 |
| WO | 9825999 A1 | 6/1998 |
| WO | 0105440 A2 | 1/2001 |
| WO | 2012036750 A2 | 3/2012 |
| WO | 2012146748 A1 | 11/2012 |
| WO | 2014145668 A1 | 9/2014 |
| WO | 2016019018 A1 | 2/2016 |

OTHER PUBLICATIONS

Supplementary EP Search Report, issued in EP Application No. 16869201.0 dated Mar. 18, 2019 [8 pages].

International Search Report and Written Opinion dated Mar. 24, 2017, during the prosecution of International Application No. PCT/US2016/063426 [13 pages].

International Search Report and Written Opinion dated Aug. 22, 2014, during the prosecution of International Application No. PCT/US2014/030473 [9 pages].

Notification of Transmittal of International Preliminary Report on Patentability dated Mar. 2, 2015, during the prosecution of International Application No. PCT/US2014/030473 [10 pages].

Supplementary Examination Report issued in Singapore Application No. 11201507598R dated Dec. 13, 2016 [2 pages].

\* cited by examiner

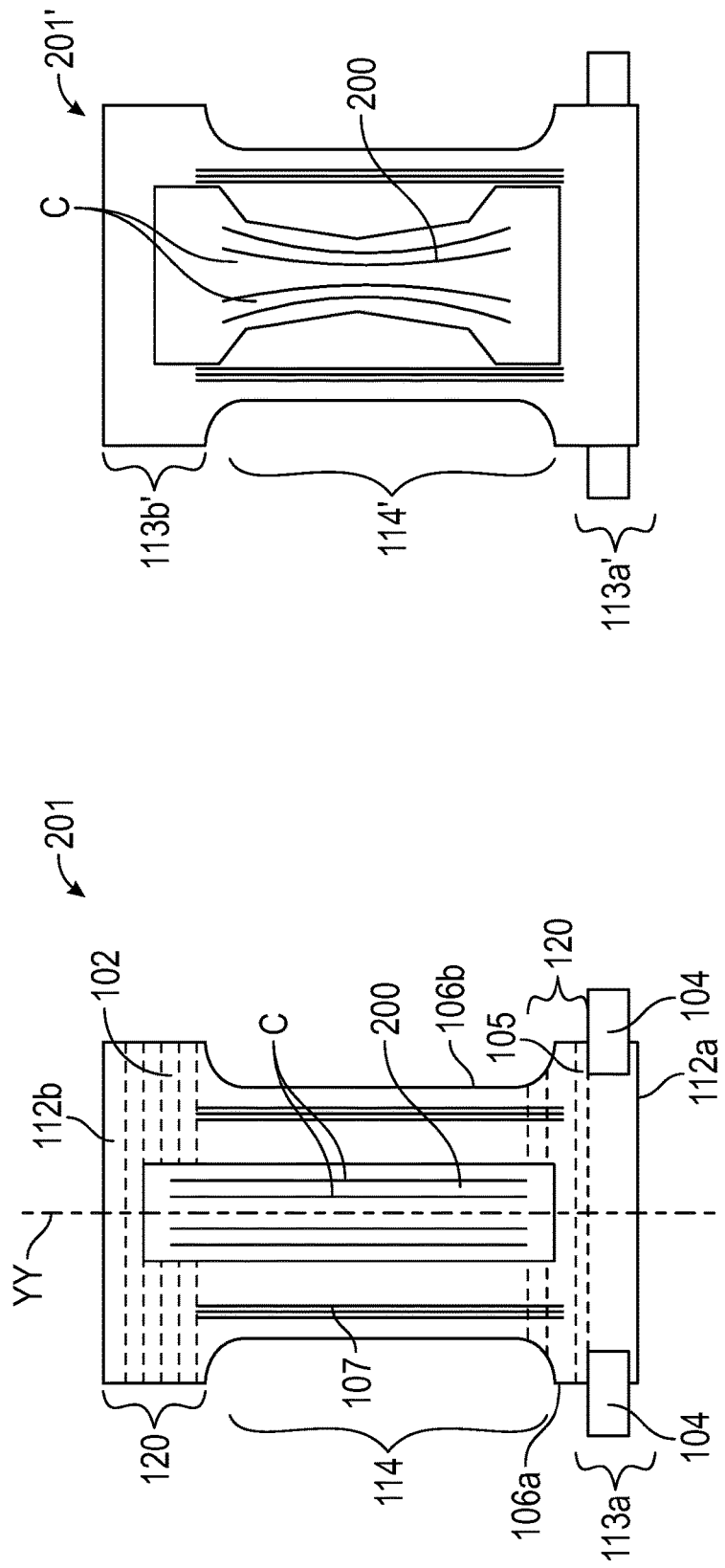
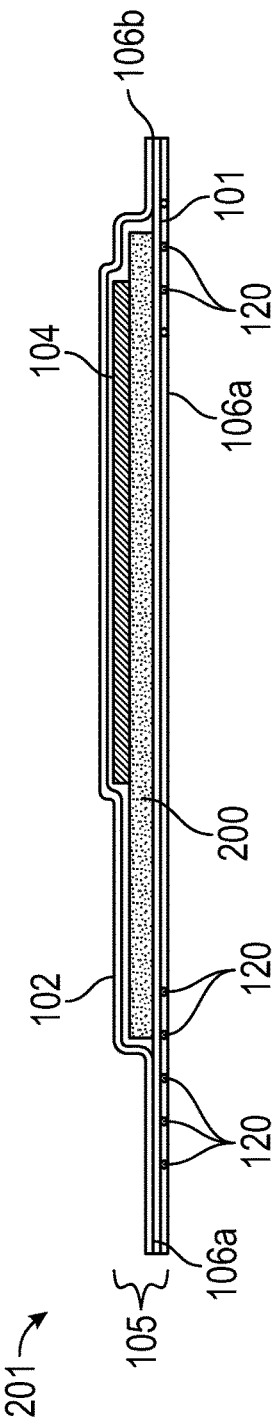
FIG. 2B
FIG. 2A
FIG. 2C

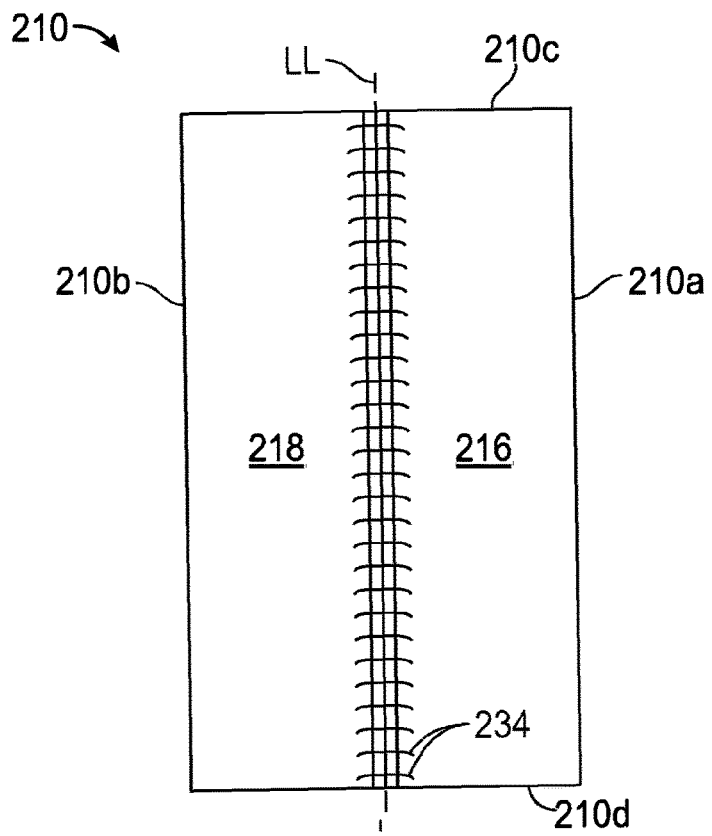
FIG. 3
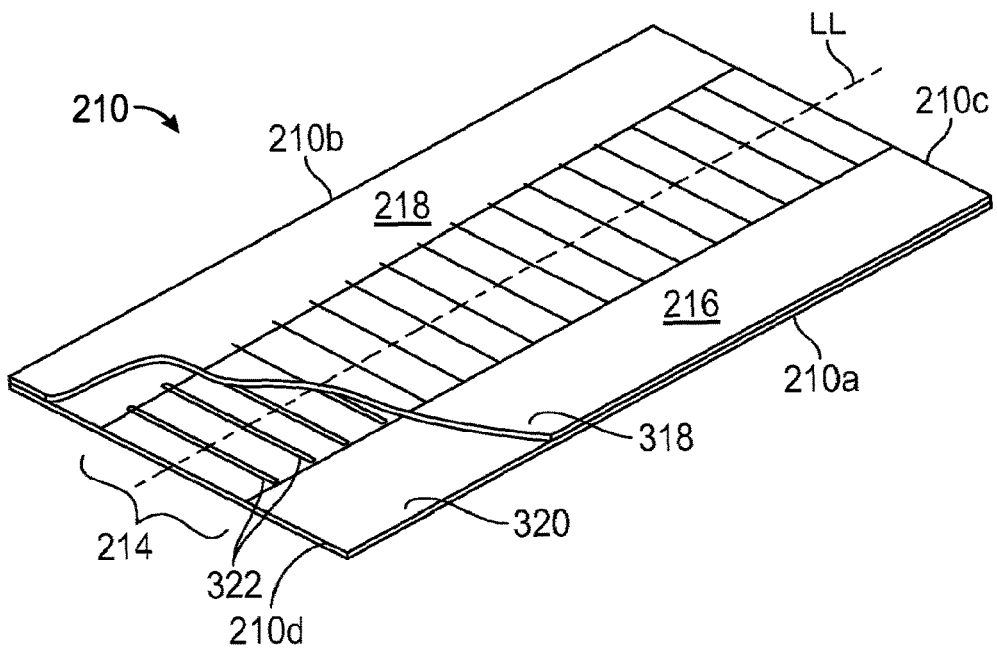
FIG. 4
FIG. 5
(NOT USED)

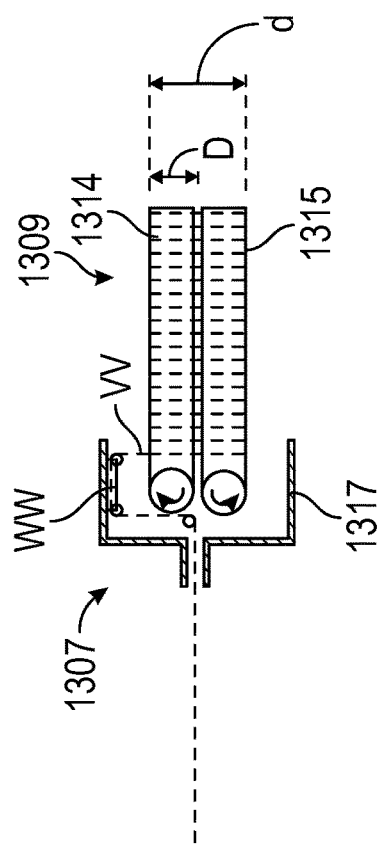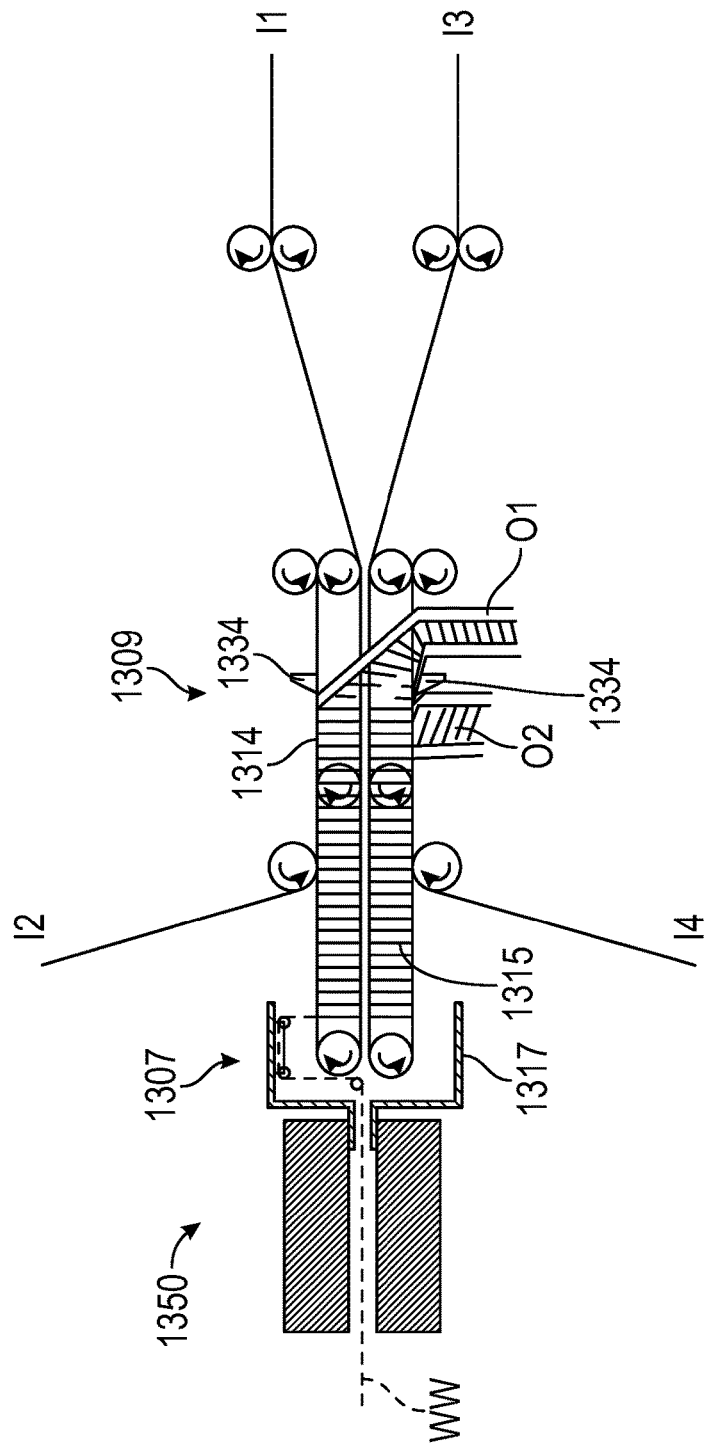

"Stretched State"

"Relaxed State"

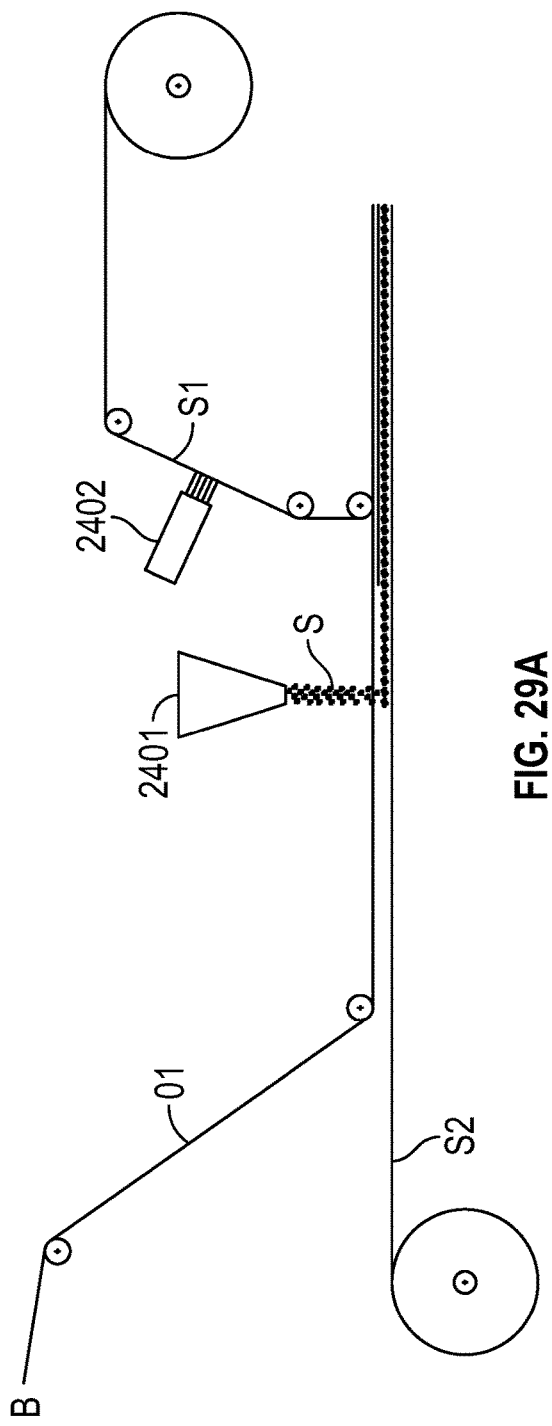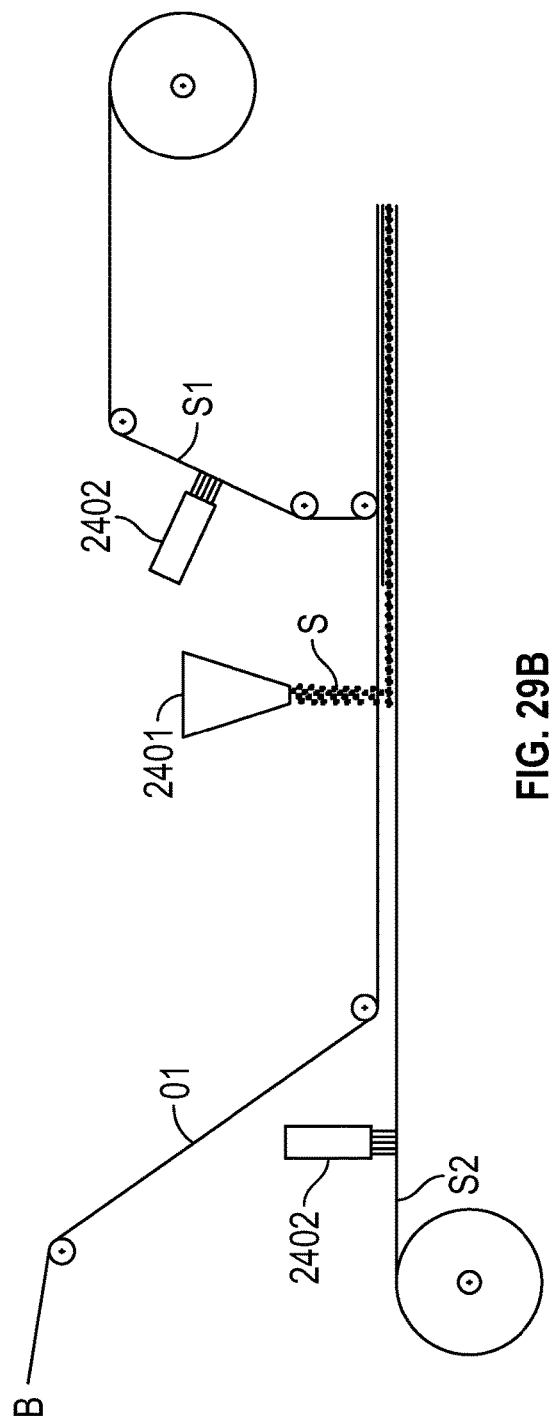

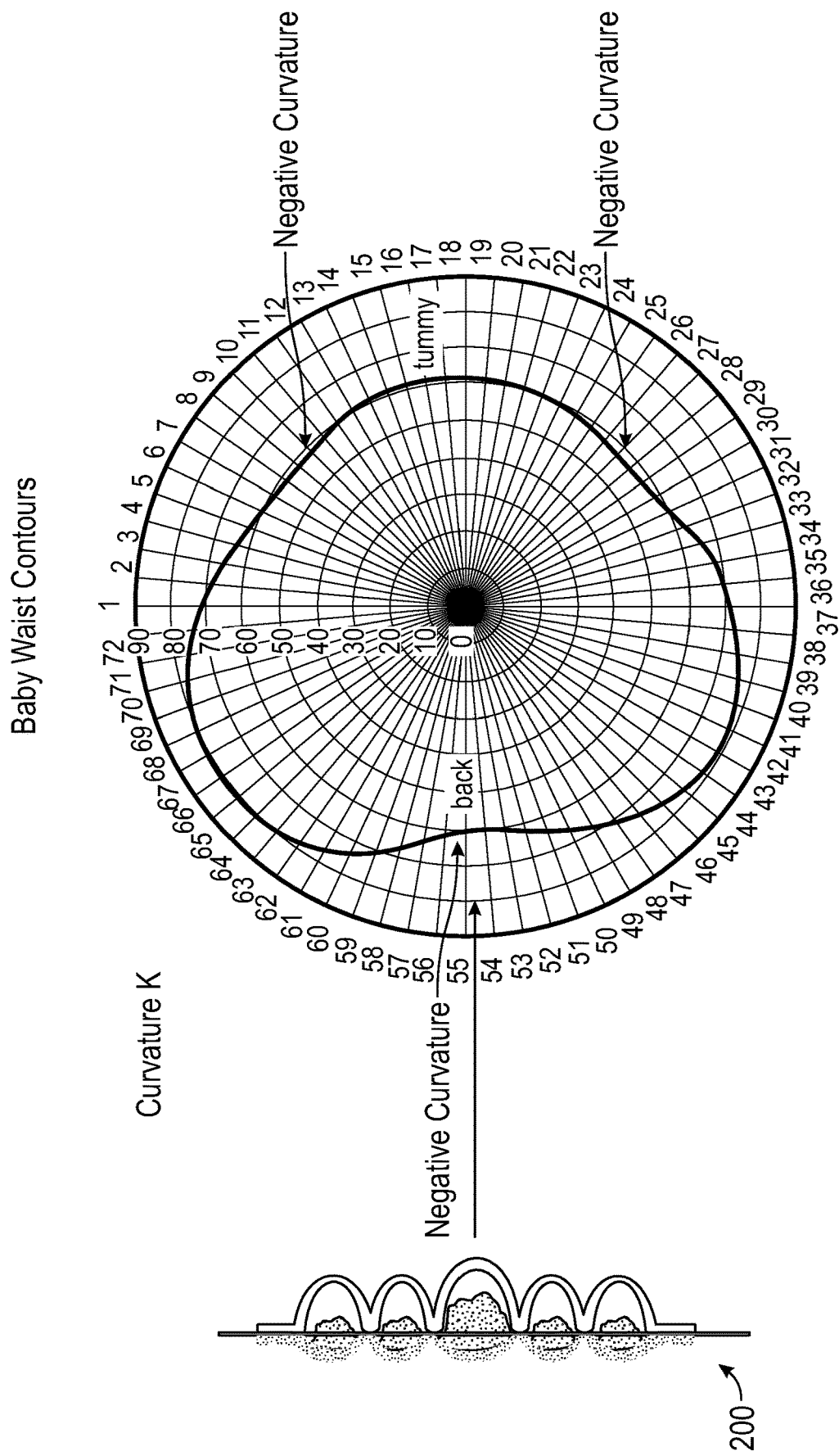

ELASTIC CORE COMPOSITE OR ASSEMBLY, AND A SYSTEM AND METHOD FOR MAKING THE ELASTIC COMPOSITE ASSEMBLY

The present application claims the benefit of U.S. Provisional Application Ser. No. 62/259,071 filed on Nov. 24, 2015 and U.S. Provisional Application Ser. No. 62/301,484 filed on Feb. 29, 2016. Each of these disclosures is hereby incorporated by reference for all purposes and made a part of the present disclosure.

BACKGROUND OF THE DISCLOSURE

The present disclosure relates generally to elastic composites and alternatively, to absorbent cores. More particularly, the present disclosure relates to elastic absorbent assemblies. Such an elastic absorbent assembly is well suited as an elastic absorbent core for a disposable absorbent article, preferably disposed centrally on the chassis thereof. The present disclosure also relates to a system and method of making the elastic absorbent assembly or elastic core assembly, or a disposable absorbent article incorporating the elastic core assembly. To illustrate various aspects of the disclosure, exemplary and preferred embodiments are described herein in the context of disposable absorbent garments.

Disposable absorbent garments contemplated by the disclosure include disposable diapers, disposable pull-on garments, training pants, and the like. These garments are worn about the lower torso or waist of the user so as to receive and contain urine and other bodily waste. Disposable pull-on garments include training pants, pull-on diapers, disposable underwear, and adult incontinence garments. As for training pants, these garments are used by young children to facilitate a child's transition from using diapers to wearing regular underpants (i.e., during toilet training). Training pants and other disposable pull-on pants have closed sides such that the user or caregiver raises the garment about the user's legs to wear the garment and slips the garment downward about the user's legs to take it off.

The principal elements of a typical disposable absorbent garment generally include a liquid permeable inner layer (or topsheet), a liquid impermeable outer layer (or backsheet), and an absorbent core sandwiched between the inner and outer layers. Elastic members may be incorporated into different parts of the garment. For example, elastic members may be positioned longitudinally along a diaper, generally outboard of the absorbent core to effect a seal around the buttocks or legs of the user. In addition, several elastic members (e.g., in the form of elongated elastic threads or strands) may be positioned laterally throughout the waist regions (including the side waist regions) of a disposable absorbent garment. The resulting elastication allows the garment to stretch when it is put on and when it is worn. The elastication allows the garment to accommodate variations in waist size and leg size of the user, while fitting snugly about the waist and legs.

Most absorbent articles used today as baby diapers have a general configuration similar to that of the absorbent article 10 depicted in FIGS. 1A and 1B. The conventional absorbent article 10 is shown in a laid out flat position in FIG. 1A, and in cross sectional view in FIG. 1B. It is common, among those skilled in the art, to describe the garment and its construction, especially the relative positions of its components, with the garment in the laid out flat position. This absorbent article 10 includes an outer-side fluid impermeable backsheet 101, a bodyside, fluid permeable nonwoven coverstock or topsheet 102, and an absorbent construction 110 positioned between the backsheet 101 and topsheet 102. An absorbent core 103 provides the primary component of the absorbent construction 110 and is designed and positioned to receive and retain bodily fluids. The absorbent construction 110 may also include at least one fluid management, fluid distribution and/or surge layer 104.

As shown in FIG. 1A, the backsheet 101 and topsheet 102 together form or define a chassis or central body 105 of the absorbent article 10. The central body 105 may be described as having a first longitudinal end edge 112a, a second longitudinal end edge 112b, and a longitudinal centerline YY that extends through the central body 111, bisecting both the first and second end edges 112a, 112b. Left and side margins 106a, 106b extend from one end edge 112a to the other end edge 112b. Each end edge 112a, 112b partly defines waist regions 113a, 113b of the central body 105 which are generally characterized as having a lateral width significantly greater than a lateral width of a central region or crotch region 114 of the central body 105. The waist regions 113a, 113b are designed to allow the absorbent article 10 to be placed about the waist of the user. In this respect, the first and second waist regions 113a, 113b may be described as front and rear waist regions 113a, 113b, respectively. The conventional absorbent article 10 further includes a fastening means 104 attached to each side of the rear waist region 113a. The fastening means 104 are extendible and thereby, fastenable to a corresponding side of the front waist region 113b. The fastening means 104 helps to retain the article 10 around and on the body of the user. The absorbent article 10 also includes a means for elasticizing 107 the article 10 to maintain closure and sealing around the user's legs. The elasticizing means 1057 (e.g., leg cuffs and/or leg cutters) are necessarily positioned outboard of and along longitudinal side margins 106 of the absorbent construction 110. Referring to FIG. 1A, the conventional absorbent core 110 is centrally positioned in and about a crotch region 114 of the absorbent article 10.

Most diaper cores are made from mixtures of fibers and superabsorbent particles, specifically cellulose based fibers derived from wood pulp and superabsorbent particles (SAP) derived from polyacrylic acid derivatives. See e.g. U.S. Pat. No. 6,540,853 (hereby incorporated by reference and made a part of the present disclosure). SAP-nonwoven absorbent composites of the type disclosed in this patent reference are available to the diaper manufacturing process in roll form and allow much greater freedom for the design of absorbent cores. Nevertheless, because fluff pulp-superabsorbent cores are generally provided as a continuous stream or web of absorbent material, the simpler and most cost efficient processes require the absorbent core to be maintained in a generally rectangular shape.

These cores are typically formed into rectangular shapes that are designed for incorporation into an absorbent article. The core shape, particularly its width, is maintained at dimensions that accommodate placement within a diaper corresponding with the crotch area of the user. Moreover, it is preferred in many applications for the absorbent core to take on a nearly hourglass shape. Such diaper cores are known in the art as providing a narrower crotch region that presents a better fit and comfort for the user. The hourglass shape also provides wider regions at the longitudinal ends of the core, which enhances the absorbency and leakage control capability of the diaper at those regions above the central crotch region.

As known in the art, the preferred diaper assembly process is a substantially linear and efficient machine directed process that produces a high volume of packaged products. Because of the nature of the consumer product as a disposable, high frequency of use item and the abundance of competing products and alternative products (e.g., reusable cloth diapers), it is imperative to maintain the low cost of the final product. Accordingly, it is also imperative to control the complexity of the manufacturing process and to minimize steps and material waste. This presents a technical challenge to one attempting to create alternative shapes and functionalities in the conventional disposable absorbent article. For example, although an hourglass shaped diaper core is generally desirable or, in some applications, a core having distinct areas of absorbency, additional cutting or forming steps or increased material cost may make the alternative design less effective.

FIG. 1C illustrates another prior art disposable absorbent article 10'. The absorbent article 10' employs a design in which an absorbent core 110' is reduced in width in the crotch region 114', but is wider at the front and rear waist regions 113a', 113b'. The result is an absorbent core 110' having a more hourglass shape. To achieve this desired hourglass shaped core, a rectangular absorbent core section is cut from a continuous web of absorbent material and shaped further, particularly in forming the narrow central region.

In any event, absorbent core configurations achieving further functionalities and/or improved fit and comfort for the user or wearer are desirable. Caution must be exercised, however, to minimize material cost and manufacturing complexity.

United States patent application publications US2005/0131373A1 and US/2005/0139311A1 provide background information on elastic composites (and the manufacture of such composites) of the type relevant to the present disclosure. Accordingly, some portions of the publications have been included herein to facilitate description of the disclosure. In any event, these two publications are also hereby incorporated by reference and made a part of the present disclosure, but only to the extent that incorporated subject matter provides background information and/or exemplary composites and processes suitable for use on, or with, the present inventive composites, systems, and methods. Thus, the incorporated subject matter shall not serve to limit the scope of the present disclosure. These publications and documents are also directed to an elastic composite having cross-directional elasticity, as well as a system and method of making the same. More specifically, these prior publications describe elastic composites in which an elastic construction imparts generally lateral elasticity to the composite in a direction that corresponds to the cross-machine direction. Such an elastic composite provides certain advantages and benefits for the disposable absorbent article, and also, the system and method of making the elastic composite and the disposable absorbent article. For example, the provision of such an elastic composite or a sub-process of making an improved elastic composite affords flexibility, efficiency, and productivity in the system and process. These advantages and benefits translate further to cost efficiency and cost savings.

SUMMARY OF THE DISCLOSURE

The present disclosure relates generally to elastic composites and alternatively, absorbent cores. Specifically disclosed herein are elastic absorbent assemblies and a system and method of making the elastic absorbent assembly. Such an elastic absorbent assembly is well suited as an elastic absorbent core for a disposable absorbent article, disposed centrally on the chassis thereof. Thus, the elastic absorbent assembly may be referred to as an elastic or elasticated core composite or assembly, and in the context of a disposable absorbent garment. Whether referred to as an elastic absorbent assembly, elastic core composite, or elastic core assembly, it is contemplated that the elasticized absorbent product or products disclosed has applications beyond disposable absorbent garments.

Also disclosed are a system and a method of making the elastic absorbent assembly or elastic core assembly, and further, a disposable absorbent article incorporating the elastic core assembly.

In one aspect, an elastic absorbent assembly includes a top layer, a bottom layer, and an elastic construction therebetween. The elastic absorbent assembly further includes absorbent material supported between the two layers. Preferably, the elastic construction is composed of spaced apart elastic strands sandwiched between the two material sheet-like layers, and preferably adhered to one or both layers (to elasticize the absorbent assembly). Furthermore, the nonwoven layers are preferably bonded, at least partially, along a direction generally transverse to the elastic strands, thereby forming or urging a plurality of encapsulating spaces between the layers and in which absorbent material is supported. A line along which one or more bond sites are situated to bond the layers together may be disposed along the sides of the encapsulating spaces to further define the encapsulating space. A plurality of such bond lines may be disposed transverse to the plurality of elastics to define a plurality of said encapsulating spaces.

In one embodiment, an elastic absorbent assembly for incorporation into a disposable absorbent garment is presented. The elastic absorbent assembly comprises an a base layer, a top layer, and an elastic construction disposed in between, or sandwiched by, the top and base layers. The elastic construction is provided by a plurality of spaced apart elastic elements forming, with the base and top layers, a plurality of encapsulating spaces or preferably elongated capsules, wherein absorbent material is disposed. Preferably, the top and base layers are nonwoven and the absorbent material includes, but is not limited to, superabsorbent polymer particles.

Moreover, the elastic construction preferably comprises a plurality of spaced apart elastic elements in the form of strands, filaments, and the like. The elastic elements are preferably secured to one or both of the top and base layers at spaced apart or intermittent bond sites or points, thereby forming the encapsulating spaces. In such a core construction or assembly, the elastic elements are directed transversely to the direction of the elongated encapsulating capsules, which direction of the elastic elements being the lateral and cross-machine direction and the direction of the capsules being the longitudinal and machine direction. Between the bond sites mutually securing the top and base layers and the elastics, the two layers may be unbonded or bonded. Thus, the two layers may be bonded continuously at laterally spaced, preferably continuous bond lines that also hits or crosses most, if not all, of the spaced apart elastic elements at the aforementioned bond sites or bond points.

In another embodiment, the elastic absorbent assembly further comprises another top or cover layer, preferably nonwoven, extending over the first top layer. The cover layer may be substantially unsecured to the top layer and may form additional void spaces therebetween (upper void spaces). In some embodiments, additional absorbent material may be provided in portions of the upper void spaces.

In some embodiment, the superabsorbent polymer particles are located in at least some of the plurality of capsules.

In certain embodiments, the sizes or shapes of the capsules are non-uniform and may vary from capsule to capsule or from one region of the core assembly to another region.

In still other embodiments, the elastic absorbent assembly further comprises an acquisition layer.

In specific embodiments, the elastic absorbent assembly further comprises a distribution layer between an acquisition layer and the primary elastic core assembly comprising the capsules.

In some embodiments, the constituents of the capsules are non-uniform and may vary from capsule to capsule or from one region of the core assembly to another region.

In some embodiments, the top and base layers are bonded between the capsules so as to segregate one capsule from adjacent capsules.

In some embodiments, the top and base layers are un-bonded between the capsules or in certain segments between bond sites of the elastic elements, such that one capsule is disposed in fluid communication with or open to adjacent capsules.

In some embodiments, the elastic construction is comprised of two sets of spaced apart elastic elements that are disposed transverse to one another, such that elastics of the first set cross elastics of the second set.

In some embodiments, the elastic construction is comprised of two sets of spaced apart elastic elements that are disposed transversely to one another, thereby forming pockets or cells bounded by elastics and the top and base layers.

In some embodiments, the elastic construction is comprised of two sets of spaced apart elastic elements that are disposed transversely to one another, thereby forming pockets or cells bounded by four segments of elastics and the top and base layers bonded to the four segments of elastics. In further embodiments, the pockets provide an all-around cell or pocket enclosure in which absorbent material is deposited.

BRIEF DESCRIPTION OF THE DRAWINGS

FIG. 2A is a simplified plan view of the disposable absorbent garment in FIG. 2, in an open, flat configuration;

FIG. 2B is an end cross sectional view of the disposable absorbent garment in FIG. 2A;

FIG. 2C is a simplified plan view of an alternate disposable absorbent garment, according to the present disclosure, in an open, flat configuration;

FIG. 3 is a plan view of an elastic composite shown in an extended, stretched condition, according to the prior art;

FIG. 4 is a perspective view of the elastic composite with a cut-out to show an elasticized region, according to the prior art;

FIG. 5 is NOT USED AND IS LEFT OUT;

FIGS. 13B-C are simplified illustrations of a system of making the elastic composite in FIG. 12;

FIG. 13D is a simplified illustration of an alternative system of making elastic composites;

FIGS. 29A and 29B are simplified schematics of alternate systems and methods of making an elastic core assembly, according to the present disclosure;

FIG. 33 is an illustration for showing the selective placement SAP-filled capsules relative to a baby waist contours;

DETAILED DESCRIPTION OF PREFERRED EMBODIMENTS OF THE DISCLOSURE

Generally, the present disclosure relates to an elastic composite, and to a system and method for making the elastic composite. More particularly, the disclosure is directed to an elastic composite having cross-machine or cross-directional elastic or stretch properties. Such an elastic composite is sometimes referred to herein as an elastic composite having cross-directional elasticity and further, as a cross-directional elastic composite.

As described previously, various aspects of the present disclosure are particularly suited to or for a disposable absorbent garment, such as baby diapers and training pants. To illustrate the disclosure and preferred embodiments of the disclosure, much of the following Detailed Description will be provided in the context of such disposable absorbent garments. It is contemplated that various aspects of the inventive composite, garment, system, and process may be applicable to other material structures and processes. This Detailed Description and exemplary embodiment should not, therefore, be construed as limiting the disclosure to the structures, configurations, methods, and processes described herein.

Figure 1C:
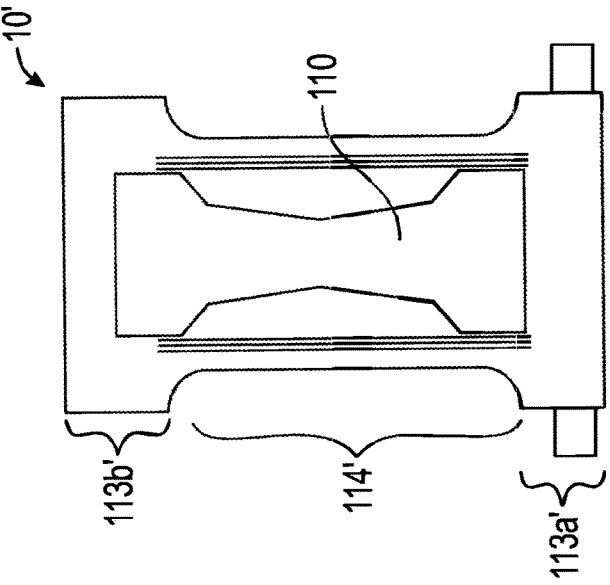
FIGS. 1A and 1C are plan views of a conventional disposable absorbent garment in the unfolded configuration.
Figure 1A:
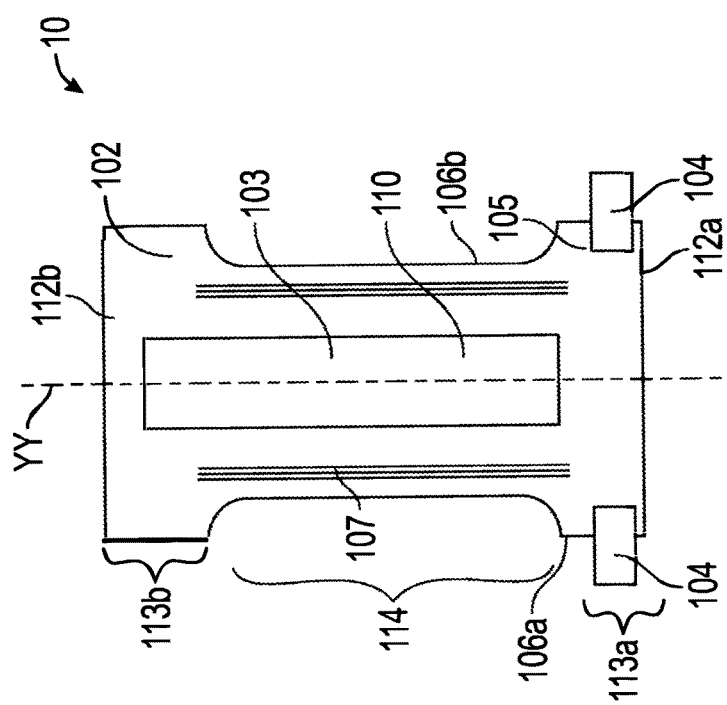
Figure 1B:
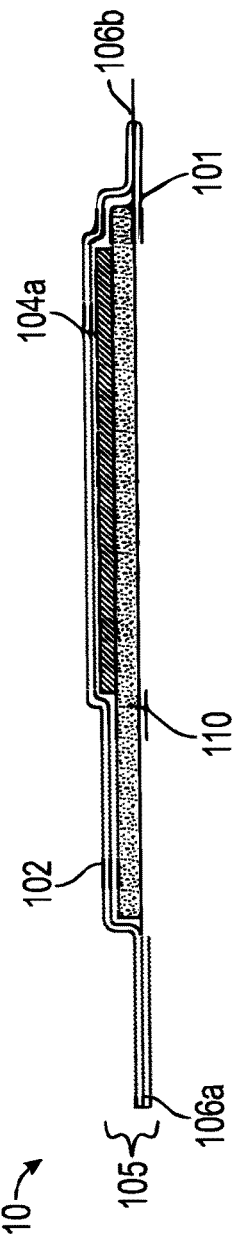
FIG. 1B is an longitudinal cross sectional view of the disposable absorbent garment in FIG. 1A.

As described previously, the conventional absorbent article 10 is shown in a laid out flat position in FIG. 1A, and in cross sectional view in FIG. 1B. An absorbent core 103 provides the primary component of the absorbent construction 110 and is designed and positioned to receive and retain bodily fluids. For purposes of the present description, the backsheet 101 may be further formed from two or more backsheet material, and include elastics incorporated therewith, to define an elasticized chassis or central body 105 of the absorbent article 10

Figure 2:
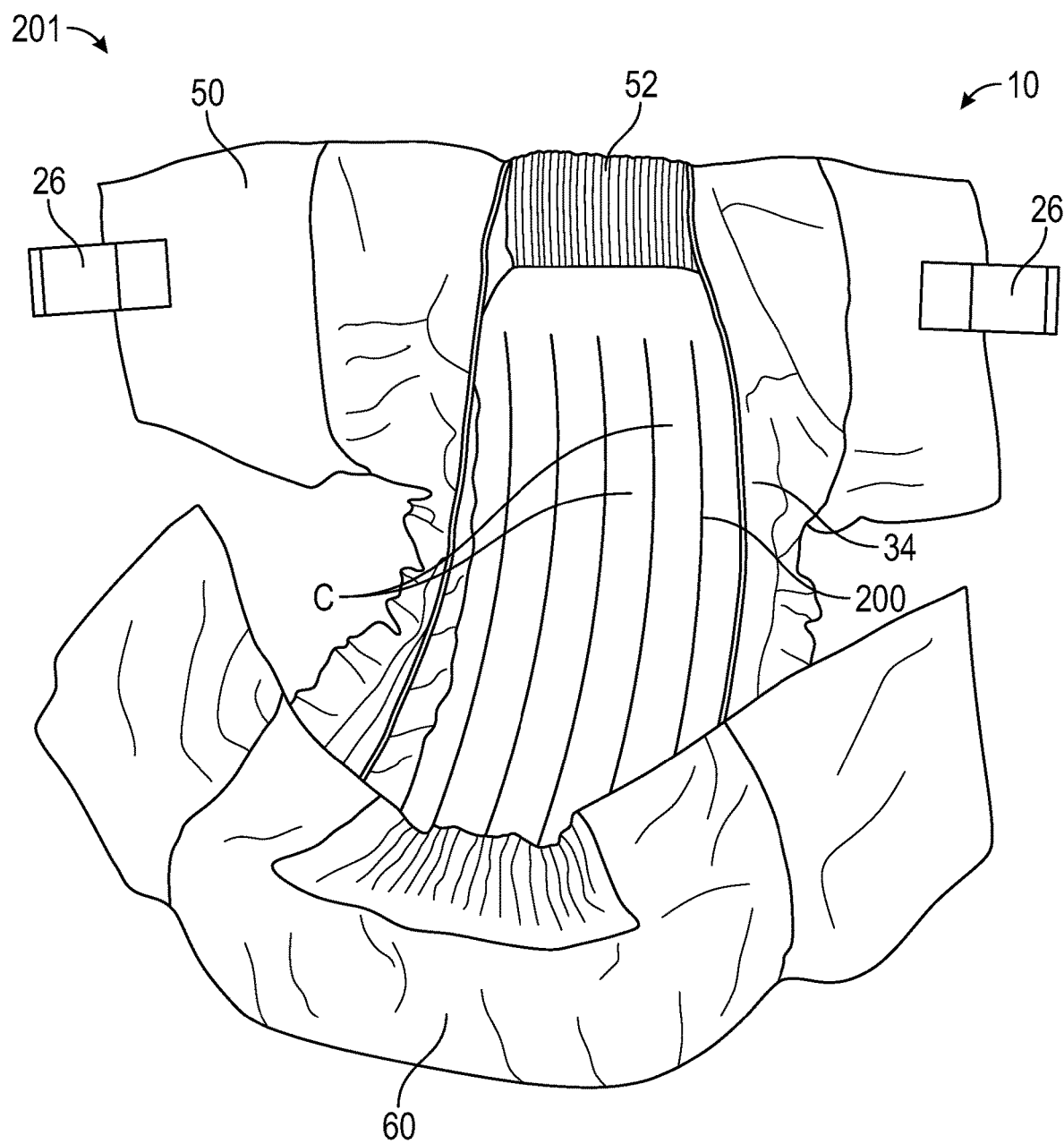
FIG. 2 is a perspective view of a disposable absorbent garment in the form of a diaper, in the open, unfastened configuration, according to the present disclosure.

FIGS. 2 and 2A-2C are simplified illustrations of one embodiment of a disposable absorbent garment in the form of a diaper, according to the present disclosure. FIG. 2 shows the diaper 200 in an open configuration, incorporating an elastic core assembly 201 according to descriptions further provided below. FIGS. 2A-2C provides additional views of such a typical diaper 201, except modified in design, to incorporate the elastic core assembly. In respect to FIGS. 1A-1C, like reference numerals are used in FIGS. 2A-2C to indicate like elements. To illustrate beneficial characteristics of the elastic core assembly 201, when incorporated with elasticized chassis, the diaper 200 is further provided with two backsheet materials 106a that sandwich a series of elastic strands 120, as known in the art. Notably, elastics 120 are placed beneath the core assembly 201, as well as beyond.

Figure 6:
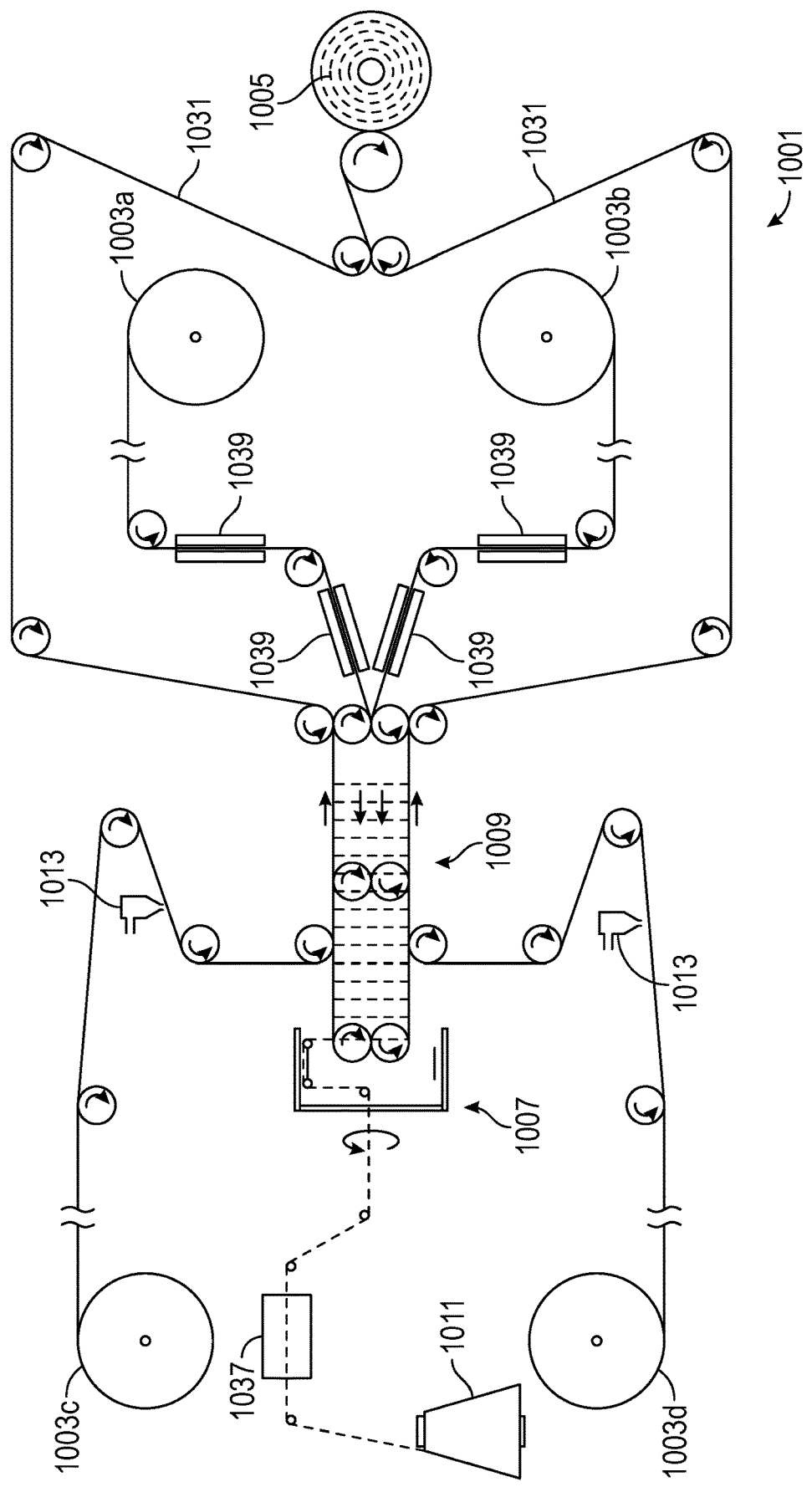
FIG. 6 is a schematic of prior art system and process for making a elastic composite.
Figure 7:
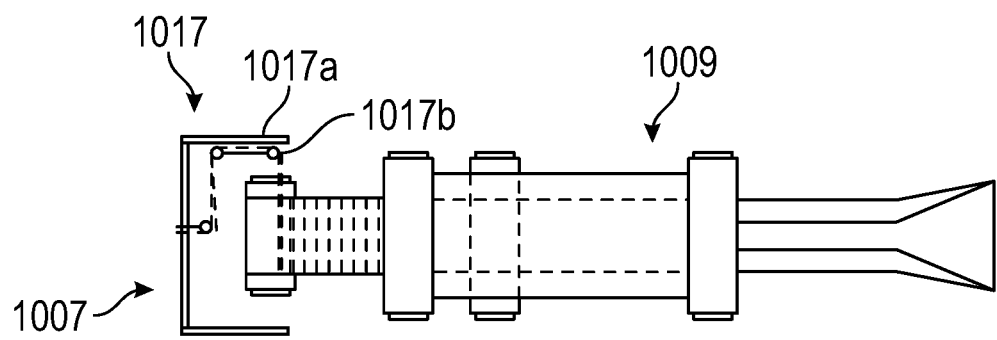
FIG. 7 is a top view of an elastic element applicator assembly for use with the system of FIG. 6.
Figure 8:
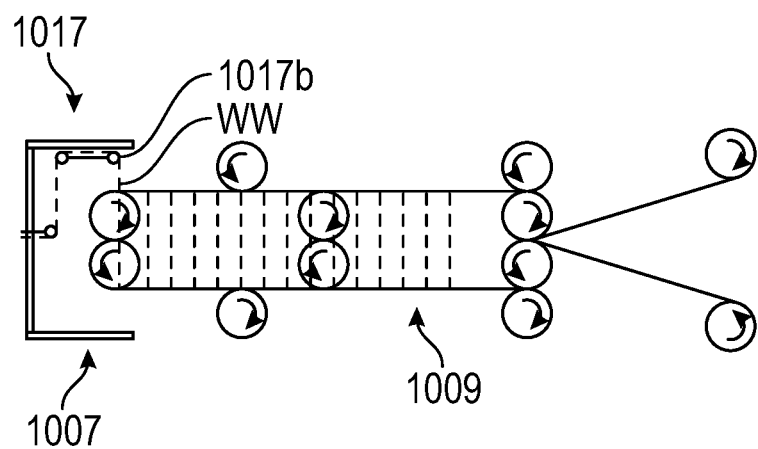
FIG. 8 is a side view of the assembly of FIG. 7.
Figure 9:
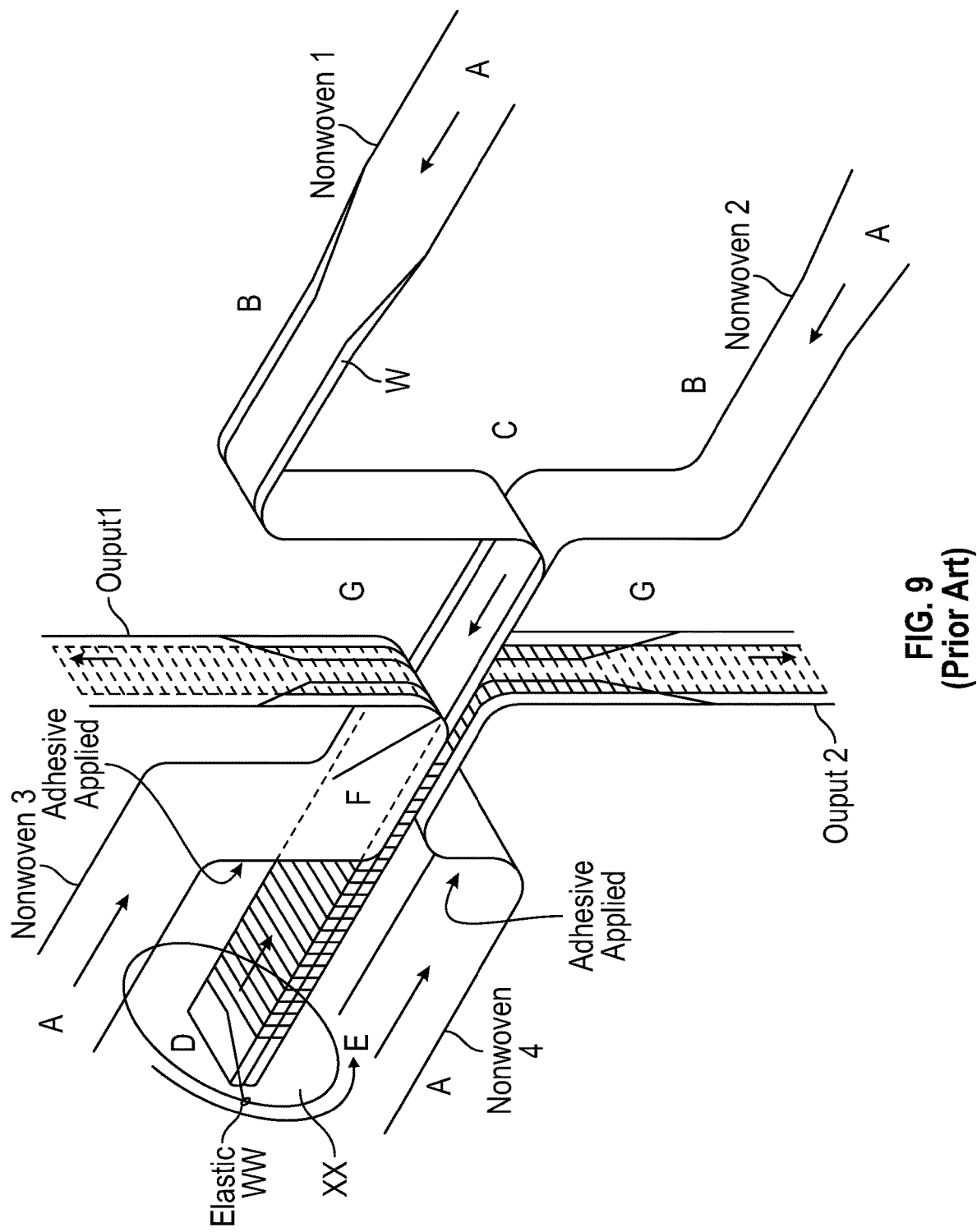
FIG. 9 is a simplified process illustration of making an elastic composite, according to the prior art.
Figure 10:
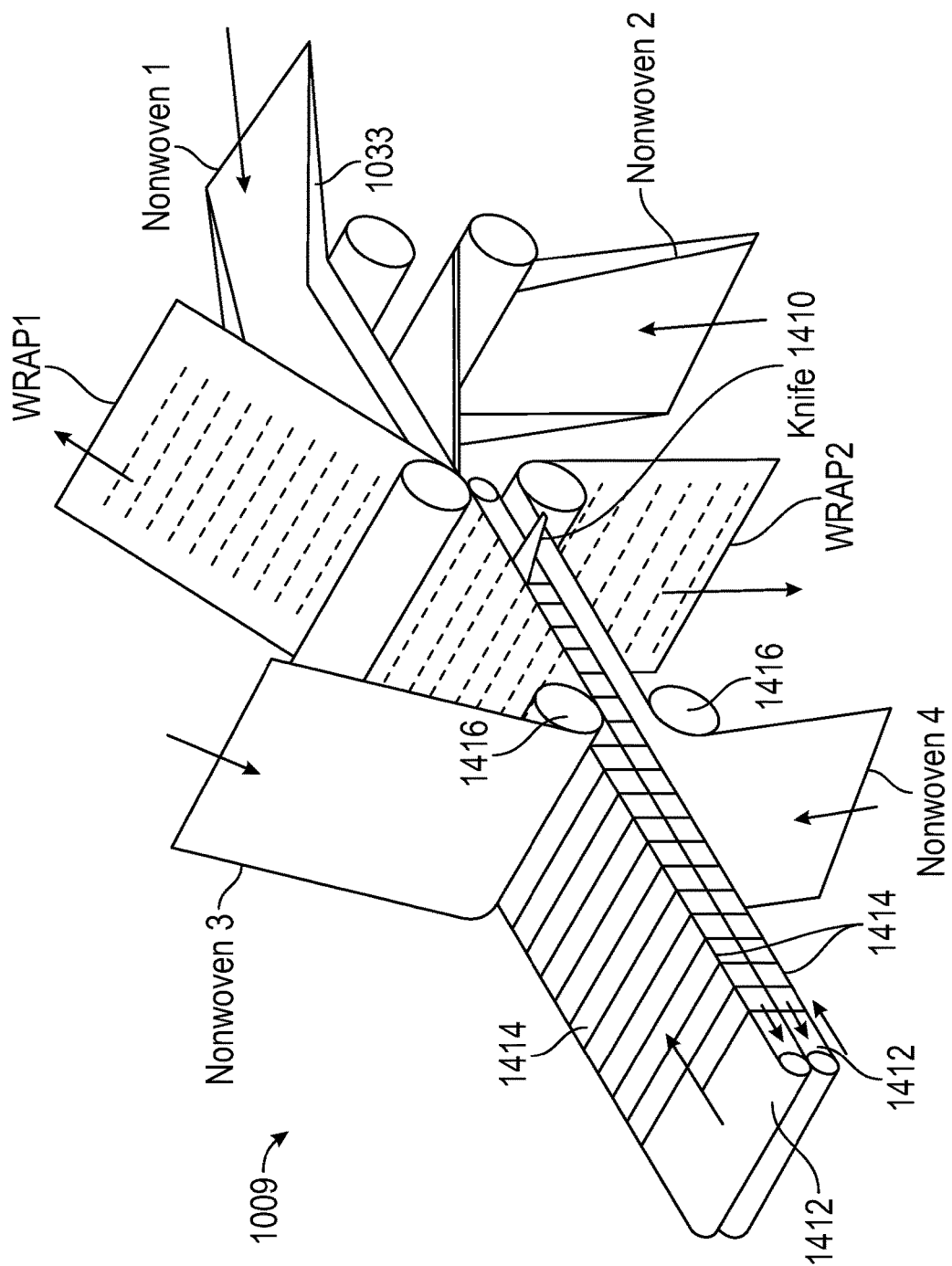
FIG. 10 is a simplified process illustration of making the elastic composite, according to the prior art

FIGS. 3, 4, and 6-8 are provided for background and to illustrate elasticized composite and processes for making the elastic composite related to the present disclosure. Some Figures, and accompanying description, are provided to illustrate the prior art and for the purpose of highlighting the contributions to the prior art provided by the present disclosure. The same Figures also illustrate use of the elastic composite, system, or method of the disclosure, and/or a product derived from the inventive elastic composite. FIGS. 3 and 4 show prior art elastic composites. FIG. 6 illustrates a prior art system, system components, and a process of making the elastic composite having a single elasticized region as previously described and disclosed in the prior art. See U.S. patent application Ser. Nos. 10/733,649 and 11/021,424 (hereby incorporated by reference and made a part of the present disclosure). These Figures and accompanying descriptions of the prior art are provided to facilitate description of the present inventive elastic composite and highlight the differences and improvements provided by the present inventive system and method.

FIG. 3 depicts a typical elastic composite band 210, now generally known in the art, but which may also be derived from the elastic composite of the present disclosure. The elastic composite band 210 is one particularly suited for use as a side panel or fastening tab of a disposable absorbent garment. FIG. 5 provides a perspective view and partial cutout of the elastic composite band 210. The elastic composite band 210 may be characterized by an imaginary centerline LL. The centerline LL preferably corresponds with the machine direction of the elastic composite band 210 during manufacture. The elastic band 210 also has side or longitudinally extending side edges 210a and 210b and laterally extending end edges 210c and 210d. In FIG. 3, the elastic composite band 210 is shown in the stretched state as, for example, when a garment incorporating the elastic composite band 210 is worn. In this state, the elastic composite band 210 stretches, in the lateral or cross-machine direction (denoted by arrows XX).

As used herein, the term "machine" direction refers to the direction at which the component, or more particularly, the material web from which the elastic composite is derived (e.g., cut from) is driven in an assembly line during manufacturing. The term "cross-machine direction" or "cross-directional," on the other hand, refers to the direction that is transverse to the machine direction. With reference to the elastic composite 210 of FIG. 3, the cross machine direction is the direction XX extending laterally relative to the longitudinal line LL. As sometimes described herein, such an elastic composite may be described as a "cross-directional" elastic composite or as exhibiting cross-sectional elastic properties.

The elastic composite band 210 has a central region 214 in which an elastic construction 214 is situated. Extending laterally from this central elastic or elasticized region 214 are regions 216 and 218, which are substantially non-elasticized ("dead zones"). As shown in FIG. 3, the regions 216, 218 occupy the expanse between the central elastic region 214 and the side edges 210a, 210b.

FIG. 6 is provided to illustrate a known system, and system components, and process of making or manufacturing an elastic composite, as previously practiced and described in more detail in U.S. patent application Ser. Nos. 10/733,649 and 11/021,424. In the prior art process illustrated therein, two elastic composite web outputs 1031 are produced from four separate non-woven web inputs 1003a, 1003b, 1003c, and 1003d. Referring first to FIG. 6, a system 1001 includes four separate non-woven web inputs 1003a-1003d, which provide a web or roll of non-woven material for the elastic composite. The system further includes an output assembly or reel 1005 that receives two elastic composite webs 1031 from the rest of the process. These two separate elastic webs may be later fixed together after manufacturing to produce the kind of composite having two elasticized regions.

Central to the system 1001 is a conveyor assembly 1009 for receiving, manipulating, and conveying each of the non-woven web inputs. The conveyor assembly 1009 is positioned and operatively associated with an elastic element applicator such as a spinning head assembly 1007. The assembly 1007 applies elastic fibers or strands upon, onto, and/or integrally with the non-woven web inputs. The spinning head assembly 1007 further includes a spinhead 1017, preferably in the form of a spinning bracket, or cylinder 1017 and the like. The spin cylinder 1017 is configured to hold an "end section" of the continuous strand WW of elastic and move it about a generally vertical plane XX in a reciprocal or repetitive pattern (relative to the conveyor assembly 1009). This plane XX is defined by the area within the spinning perimeter of the cylinder 1017 and which is traced by the outer most bracket or eye 1017b securing the strand of elastic WW to the spin cylinder 1017. The paths of the spinhead 1017 and the section of elastic strand retained thereby are provided on the plane XX.

As shown in the schematic of FIG. 6, non-woven inputs 603a and 603b are fed, utilizing a series of rollers, into the conveyor assembly 1009. Before the two non-woven webs are fed into the conveyor assembly 1009, the webs are directed through the folding guides or plates 1039. The folding guides 1039 serve to effectively reduce the overall width of the non-woven web by folding the lateral or side edges along a pre-determined, longitudinally-extending side fold line YY. The first folding guide 1039a initiates the first 90° turn while the second folding guide 1039b initiates a second 90° turn. The roller 1039 disposed in between the guide 1039a, 1039b facilitates the folding process. The two folding guides 1039 and roller 1369 may be referred together as a folding guide assembly.

The conveyor assembly 1009 is set up so as to guide these two non-woven webs 1003a and 1003b through the center of the assembly 1009 towards and eventually inside the elastic spin cylinder 1007 (into the spinning path). Once inside the spin cylinder 1017 the conveyor assembly 1009 delivers the non-woven webs to each outside, upper and lower faces (outward faces) of the conveyor assembly 1009. At this point, the direction of travel of the non-woven webs is reversed and the webs are directed outward from the spin cylinder 1007. As the non-woven webs exit the spin cylinder 1017, an elastic strand WW is wrapped around the entire conveyor assembly 1009, and as it contacts the upper and lower face of the web platforms it comes into contact with the non-woven web. As shown in several of the Figures, the elastic strand WW is applied crosswise or laterally on the web, and transverse to the direction of the moving web. The friction between the tensioned elastic strand and the non-woven webs on the upper and lower faces of the conveyor assembly draws the "wrapped" elastic strand out of the spin cylinder 1017 and towards contact with two further non-woven webs 1003c and 1003d.

The non-woven webs 1003c and 1003d are operatively positioned upstream of an adhesive applicator 1013. Utilizing a system of rollers in conjunction therewith, the non-woven inputs 1003c, 1003d and adhesive applicators 1013 apply a web of pre-glued non-woven material onto the conveyor assembly 1009 and onto the elastic strand "wrapped" around the non-woven webs 1003a and 1003b.

Furthermore, the system 1001 employs a standard elastic input source, e.g., a bobbin of elastic yarn, that feeds elastic strands or fibers WW onto a tensioning/speed controlling unit 1037 and then to the spin cylinder or the spinning head 1017, so as to apply the strands WW onto the conveyor assembly 1009 and the non-woven material webs conveyed therethrough. Elastic is taken off the bobbin, box or positive drive system and fed through a tension and speed controlling motor towards the spin cylinder 1017. The elastic WW is delivered through a hollow shaft in the motor controlling the spin cylinder 1017. The elastic WW then passes into the spin cylinder 1017 and is guided by rollers, eyes or any other suitable mechanism around the inside face of the spin cylinder 1017.

As shown in FIG. 6, the spinning head assembly 1007 is positioned about and in the vicinity of one end of the conveyor assembly 1009. In operation, the spinning head 1017 spins about the vertical plane XX which intersects the ends of the web moving platforms 1412 so as to deliver the elastic strands WW around and about both web moving platforms 1412. In operation, the first and second non-woven move along the outside or exposed surfaces or sides of the web moving platforms 1412 and receives the elastic strands WW delivered by the spinning head 1017. By way of its movement away from the spinning head 1017, the moving web draws the continuous elastic strand WW from the spinning head 1017.

FIG. 6 and the above accompanying description illustrates a method of making an elastic composite that is different from and precedes the present disclosure. Most of the steps, sub-processes, components and sub-systems associated with the method may be employed, however, in the systems and methods of the present disclosure. In fact, applicable detail descriptions of system components and operation may be borrowed from this portion of the specification to illustrate the inventive systems and methods. Differences between the previously disclosed systems and the systems to be described, in respect to the present disclosure, represent, or arise from, improvements provided by the present disclosure. Such differences are discussed below in more detail.

The descriptions shifts now to an alternative and, for some applications, improved but still prior art system and process for producing an elastic composite having a plurality of mutually spaced-apart elastic elements, and, more preferably, such an elastic composite having cross-directional elasticity. FIGS. 11 through 17 are provided to help illustrate such an elastic composite with cross directional elasticity, and systems and method of making the elastic composite. In further design variations, the elastic composite has a pair of non-elasticized regions or dead zones and a central elastic region positioned therebetween. Of particular concern is an alternate method of making a continuous web of elastic composite having cross-directional elastic properties, with marked improvements in efficiency, productivity, flexibility, and/or economy. As discussed herein, such an elastic composite may lend itself to post-processing and integration of the elastic composite into various components of a disposable absorbent article.

As discussed previously, the term "elastic composite" is used to refer to a multi-component material construction that includes elastic elements. In some products, the elastic components include one or more nonwoven layers and elastic elements that impart elasticity on the nonwoven layer(s). In further designs, such an elastic composite is in a form suitable for direct integration as a component in a disposable absorbent article. Such an elastic composite may be fed directly into a system and main process for making a disposable absorbent article. In other product designs, the elastic composite is in a form that is well suited for further processing before integration as a component in a disposable absorbent article. For example, the elastic composite provided herein may be a novel construction that captures the target cross-directional elastic properties of a plurality of elastic elements and provided in a form that facilitates further processing. In one further example, the elastic composite is a laminate construction that captures a desired multi-layered elastic construction and in a form that can yield a plurality of individual cross-directional elastic composites in ready form. In other examples, the novel laminate construction is further processed to yield individual cross directional elastic composites having a multilayered central elastic region and, in a further example, a pair of non-elastic regions or dead zones.

With the methods of manufacturing discussed earlier, particularly, elastic composites featured a central elastic region having a width that is depended on, and thereby, limited by, certain manufacturing parameters. Specifically, the lateral or cross-directional width of the elastic region in the stretched state is fixed by the dimensions of certain manufacturing components. For example, the diameter of the spin head (and also of the vertical plane XX; imposes a length limitation on the elastic elements in the central elastic region. The spin head encircles the conveyor assembly and thus, the width of the nonwoven web that is supported on the conveyor assembly must be less than the diameter of the spin head. Such a limitation on the length of the elastic element also dictates the minimum width of the nonwoven sheet onto which the elastic element is applied. Similarly, the width of the conveyor that conveys the nonwoven to the spin head, and about which the elastic is wrapped, dictates the practical width of the nonwoven sheet and thus, the length of the elastic elements. Furthermore, the diameter of the spin head is limited by the practical speed of the manufacturing process. In FIGS. 13-19, systems and methods are provided that readily allow for a cross directional elastic composite having a relatively wider elastic region. In yet another example, a system and method are provided for varying the width of the elastic region.

Figure 11:
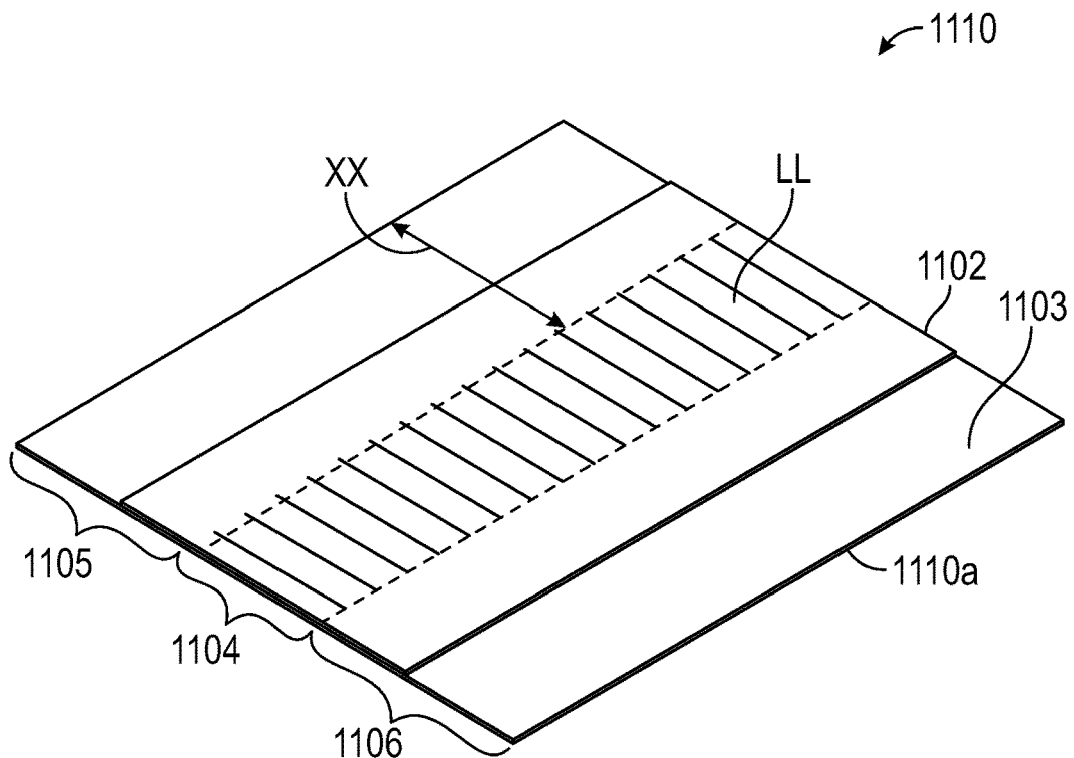
FIG. 11 is a simplified illustration of a prior art cross-directional elastic composite.

FIG. 11 is provided to illustrate a type of elastic composite 1110 relevant to the present disclosure. The conventional elastic composite 1110 has a central elastic region 1114 in which an elastic construction 1114 is situated and non-elastic regions (dead zones) 1105, 1106, each aside the central elastic region 1114. The elastic composite 1110 is composed of an upper nonwoven layer 1102, a lower nonwoven layer 1103, and a plurality of mutually spaced apart elastic elements 1101 sandwiched therebetween. The plurality of elastic elements 1101 are positioned centrally and are aligned generally laterally, preferably generally perpendicular to a longitudinal centerline LL of the elastic composite 1110. Preferably, the elastic elements 1101 are strands that are tensioned when applied to the nonwoven layers 1102, 1103 so that the nonwoven layers are later gathered by the elastic elements 1101 as the elastics relax.

Figure 12:
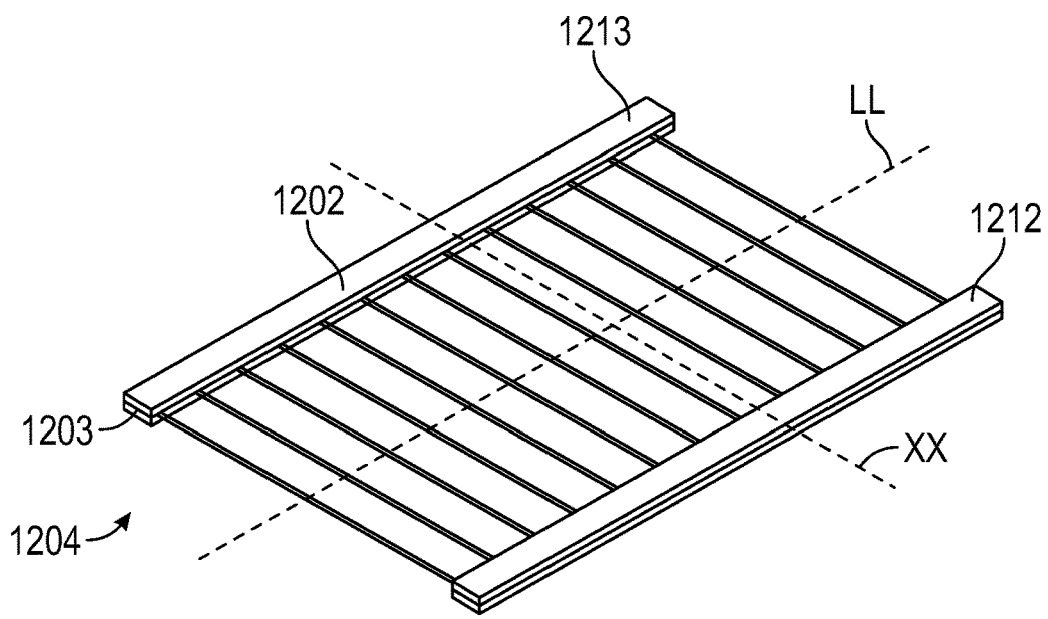
FIG. 12 is a simplified illustration of a cross-directional elastic composite in the prior art.

FIG. 12 depicts one elastic composite 1210. In one respect, the elastic composite 1210 features the same basic construction as the previous elastic composite 1110: a multi-layered, cross-directional elastic composite 1210 with a central elastic region 1204 and a plurality of mutually spaced apart elastic elements 1201 in the central elastic region 1204. The plurality of elastic elements 1201 provides a central elastic region 1204 that is clear of nonwoven layers. The elastic elements 1201 are, therefore, exposed and define an open elastic area or region 1204. Furthermore, the elastic region 1204 is situated in between a first nonwoven composite carrier 1212, and a second nonwoven composite carrier 1213 (hereinafter "carriers"). Each of carriers 1212, 1213 is preferably composed of a first or upper nonwoven layer 1202, a second or lower nonwoven layer 1203, and the ends of cross directional elastic elements 1201 sandwiched therebetween. In further designs, the upper and/or lower layers may employ a sheet material other than woven (e.g., a film). The carriers 1212, 1213 are spaced in the lateral or cross machine direction XX from a longitudinal centerline or machine direction LL of the elastic composite 1210. The carriers 1212, 1213 are placed generally in parallel relation with the centerline LL and provide the side border of the elastic composite 1210. More preferably, the open elastic region 1204 is generally centered about the composite centerline LL, and the elastic elements 1201 are equally spaced and centered about the longitudinal centerline LL in generally perpendicular relation.

A comparison of the elastic composite 1210 with the earlier elastic composite 1110, as depicted in FIG. 11, reveals at least a few important physical distinctions. A primary feature of the elastic composite 1210 is that the elastic elements 1201 are substantially uncovered or revealed between the carriers 1212, 1213. Moreover, the three-layered composite, which is now referred to as carriers 1212, 1213, has a substantially reduced width as compared to the width of the elastic region 1204. As will be further described, the nonwoven carriers 1202, 1203 serve primarily to hold elastic elements 1201 in place (even if only temporarily) and facilitate further processing of the elastic composite.

Figure 13A:
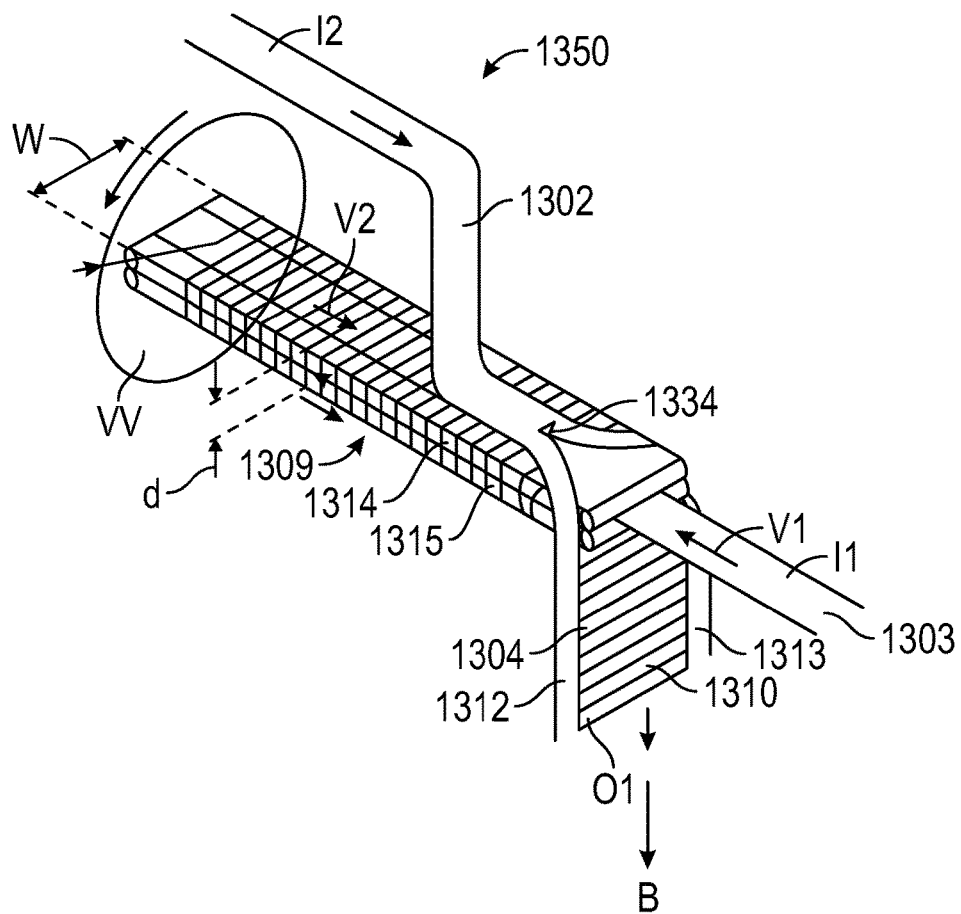
FIG. 13A is a simplified process illustration of a system and method of making the elastic composite in FIG. 12.
Figure 13B:
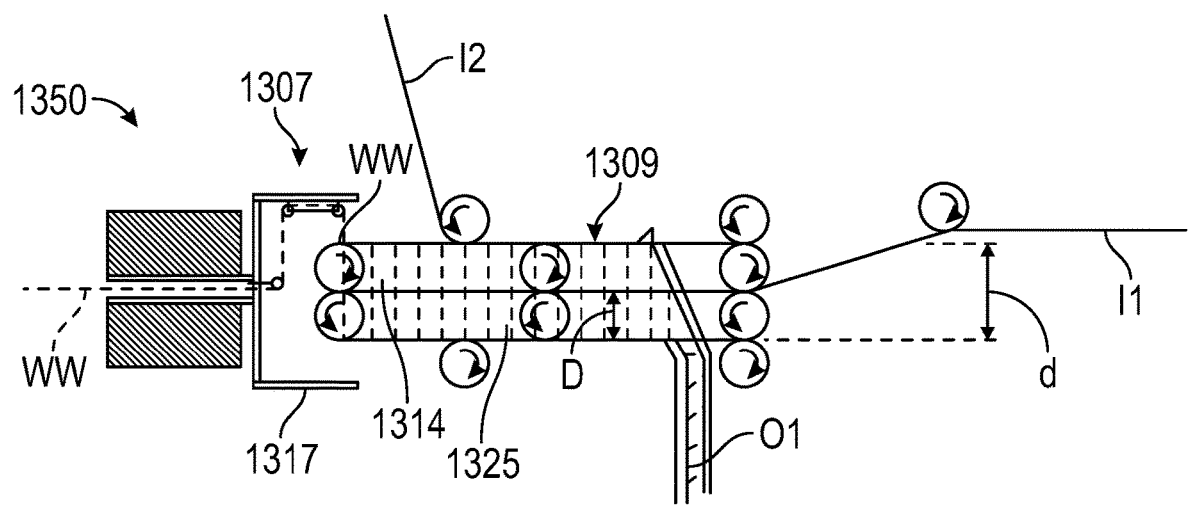

FIGS. 13A-13C are simplified illustrations used herein to describe a related, prior art system and process for making the elastic composite 1210. Suitable components for the system and apparatus shown in FIGS. 13A, 13B, are substantially the same as or equivalent to those previously described herein (see FIG. 6). Moreover, the function and operation of the components have also been described previously or are generally known in the art. Accordingly, details as to the configuration and operation of these components are not provided herein, but will be apparent to those skilled in the art.

A system 1350 suitable for the preferred embodiment includes a first nonwoven input I1 (or other suitable material), a second nonwoven input I2 (or other suitable material), and a web output O1 of a continuous elastic composite 1310. The first nonwoven input I1 provides or feeds a web or roll (not shown) of a first nonwoven layer 1303 (or other sheet of material), while the second nonwoven input I2 provides or feeds a web or roll (not shown) of a second nonwoven layer 1303. The nonwoven layers 1302, 1303 ultimately provide upper and lower composite layers for each of the two carriers 1212, 1213 of the elastic composite 1310. The system 1350 further includes an output assembly or reel (not shown) to receive the continuous web of elastic composite 1310 or output O1 and, in some applications, direct the output O1 into a main manufacturing process.

Central to the system 1350 is a conveyor assembly 1309 for receiving, manipulating, and conveying the nonwoven web inputs I1, I2 as well as the elastic composite output O1. As described previously, the conveyor assembly 1309 preferably includes an upper conveyor and platform (hereinafter upper conveyor 1314) and a lower conveyor and platform (hereinafter lower conveyor 1315). Referring to FIG. 13C, the two conveyors 1314, 1315 are placed substantially adjacent each other but still sufficiently spaced apart to allow independent movement. Preferably, the two conveyors 1314, 1315 have substantially the same dimensions of length, L, width, W, and depth, D, and are positioned in parallel relation such that one substantially mirrors the other. The vertical distance from the top or outside of the upper conveyor to the bottom or outside of the lower conveyor is the dimension "d". In most prior applications, this dimension, d, is equal to (twice the width, W) plus the gap or distance between the conveyors.

The conveyor assembly 1309 is operatively associated with a suitable elastic element applicator such as a spinning head assembly 1307 and spin head 1317 ("elastic spinners"), as described previously. The spin head 1317 extends slightly over and about the ends of the two conveyors 1314, 1315, and is configured to hold an "end section" of a continuous elastic strand WW of elastic. Revolution of the spin head 1317 moves the end section about a generally vertical plane VV and about the conveyor assembly 1309. The vertical plane VV preferably has a diameter that is just slightly less than the inside diameter of the spin head 1317. The vertical plane intersects the conveyors 1314, 1315 and further, webs moving on the conveyors 1314, 1315. As generally known, the two conveyors 1314, 1315 reciprocate such that the inside platform surface moves linearly toward and past the vertical plane VV in a first web moving direction V1, before turning as the outside platform surface. The outside platform surface moves linearly past the vertical plane VV in a second web moving direction V2 that is the reverse of the first web moving direction V1. The path of the outside platform surface is spaced outwardly of the path of the inside platform surface and in generally parallel relation therewith.

Accordingly, a first nonwoven carrier web 1303 is directed to the conveyor assembly 1309. The conveyed web 1303 is then conveyed by the upper conveyor 1314 along the first web moving direction V1 and through the vertical plane VV. After arriving at the end of the conveyors 1314, 1315, the nonwoven carrier web 1303 is passed onto the top conveyor 1314 as shown in FIG. 13A, (or, onto the bottom conveyor 1315 in alternate designs). As the nonwoven carrier web 1303 is conveyed through the vertical plane VV, a section of the elastic strand WW is applied across the nonwoven carrier web 1303. Actually, the spin head 1317 revolves about the conveyors 1314, 1315 and wraps a section of elastic strand WW about the two conveyors 1314, 1315.

Noting that the section of elastic WW is applied across the outside surface of the lower conveyor 1315 as well, the moving conveyors 1314, 1315 draw continuous strand WW away from the spin head 1317. The new substrate now consisting of the nonwoven web 1303 and the elastics applied thereon is subsequently met by a second nonwoven web 1304. The second nonwoven web 1302 is directed onto and in union with the upper conveyor 1315*a* and atop the substrate of the first nonwoven web 1303 and elastics applied thereon. As generally known, the second nonwoven carrier web 1304 is preferably applied with a process adhesive upstream of the upper conveyor 1315*a*. The adhesive is sufficiently applied to provide a secure bond between the two nonwoven carrier webs 1302, 1303 and the elastics therebetween. In alternate embodiments, another suitable process or means of bonding the layers and elastics may be employed (e.g., thermal bonding, ultrasonic bonding, embossing, etc.)

Thus, a new composite or subcomposite is provided as a result of the union of several components. This union includes: a first nonwoven web 1303 supported on the outside surface of the upper conveyor 1314; a section of elastic strand WW applied across the first nonwoven web 1303 multiple times; and a second nonwoven web 1302 applied atop the first nonwoven web 1303 and the elastics applied thereon. As shown in FIG. 13A, the section of elastic strand WW extends outward from one side of the first non woven web-second non woven web sandwich (on the upper conveyor 1314) (the "union"), wraps around the lower conveyor 1314, and encircles by returning into the sandwich or union through an opposite side. Prior to cutting, the section of elastic strand WW actually encircles or enwraps both conveyors 1314, 1315 and the first nonwoven web 1303 multiple times. Although the lower conveyor 1315 does not convey a sheet of material in the traditional way, it does support and convey (in the web moving direction V2) a series of elastic segments (of the elastic strand WW).

Referring specifically to FIG. 13A, this new composite is moved further in the second web moving direction V2 by both the upper conveyor 1314 and the lower conveyor 1315. The composite is specifically directed to a cutting or slitting mechanism ("slitter" 1334) positioned generally centrally and jutting into the path of the upper conveyor 1314. The moving composite intersects the slitter 1334 and is slit preferably longitudinally across the center of the nonwoven-elastic-nonwoven sandwich ("elastic sandwich"). The elastic sandwich is divided to create the two carriers 1312, 1313 and an open or exposed elastic region 1304 therebetween. The section of continuous elastic strand WW, which had encircled or enwrapped the conveyors 1314, 1315, is also severed to create separate elastic segments 1301. The resulting composite 1310 moves forward, which causes the two carriers 1312, 1313 to slide downward off the conveyors 1314, 1315, as shown in FIG. 13A. Preferably, the carriers fall and unwrap below the conveyor assembly 1309. By slitting the previously enwrapped elastic composite, the resulting composite output O1 may be readily removed from the conveyor assembly 1309 and further received for storage or post-processing.

In one respect, an elastic composite 1210 is provided having an exposed elastic construction or open elastic region 1204 formed by the plurality of mutually spaced apart elastic elements 1201, as shown in FIG. 12. In this composite 1210, the elastics 1210 of the exposed or open elastic region 1204 are independent or clear of any nonwoven layers. The elastic elements 1201 extend generally laterally from one carrier 1212 to the second carrier 1213, and across the longitudinal centerline LL. The elastic elements 1201 are therefore generally oriented along the cross-machine direction, and may be referred to as cross-directional elastics. Interestingly, the width of the open elastic region 1204 (i.e., the lateral spacing between the two carriers 1212, 1213) is primarily dependent on two processing parameters. Firstly, the width of the open elastic region 1204 is dependent on the total circumference of the conveyor assembly 1309, i.e., the circumference about the upper conveyor 1314 and the lower conveyor 1315. This circumference is also substantially equal to the travel length of the section of elastic strand WW about the conveyor assembly 1309 upon one revolution of the spin head 1317. This length is the sum of the width W of the upper conveyor 1314, the width W of the lower conveyor 1315, and twice the distance, d, between the upper surface of the upper conveyor 1314 and the lower surface of the lower conveyor 1315. Secondly, the width of the open elastic region 1204 is dependent on the tension applied to the elastic strand WW when the strand is applied about the nonwoven web 1303. If a relatively higher tension is applied, the width of the open elastic region 1204 in the relaxed state will be decreased.

Figure 14:
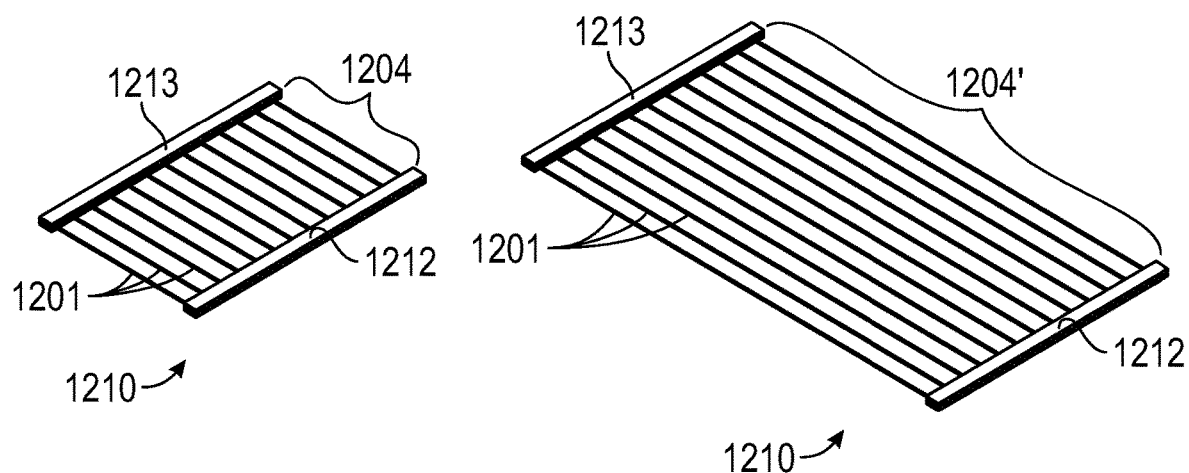
FIG. 14 are comparative illustrations of the elastic composite in FIG. 12 in a relaxed state and in an extended state.

The width of the open elastic region 1204 is also dependent on and provided by the extension state of the elastic elements when the measurement is taken. Generally, the important reference measurements are those made when the elastic elements are fully relaxed (extension factor equals 1×), and measurements taken when the elastic elements are fully extended (typical extension factor equals 4× to 6×, depending on the type of elastic used). FIG. 14 illustrates an elastic composite 1210 in a relaxed state, i.e., no tension is applied to the elastic. To the right of the relaxed elastic composite 1210 is a depiction of the elastic composite 1210' under tension, i.e., the extended state.

Example 1

In one design, the width of open elastic region may be approximated as follows:

Given, conveyor width, W=100 mm;

distance, d, from upper surface of upper conveyor to lower surface of lower conveyor=40 mm;

extension applied to continuous elastic strand=4×;

full extension of elastics=5×.

Width of open elastic region (fully extended) =

$$5 \times ((100 \text{ mm} + 100 \text{ mm} + (40 \text{ mm} \times 2))/4 = 350 \text{ mm}$$

Width of open elastic region (relaxed) =

$$(100 \text{ mm} + 100 \text{ mm} + (40 \text{ mm} \times 2))/4 = 70 \text{ mm}$$

Example 2

In another design, the width of the open elastic region is increased by reducing the extension applied to the elastic strand as it is applied to the nonwoven carrier web. The circumference of the conveyor assembly is also increased by increasing the separation of the upper and lower conveyors. In some suitable systems, one of the conveyor platforms is simply moved further from the other platform. It should also be noted that one of the conveyors is not required to move a sheet of material, but only the elastic wrapped about it. This allows for use of conveyors different from the generally flat platforms or belts commonly used to support a sheet of nonwoven.

Given, conveyor width, W=100 mm, distance, d, from upper surface of upper conveyor to lower surface of lower conveyor=100 mm, extension applied to elastics=1.5×, full extension of elastics=5×.

Open elastic region (fully extended) =

$$5 \times ((100 \text{ mm} + 100 \text{ mm} + (100 \text{ mm} \times 2))/1.5 = 1333 \text{ mm}$$

Open elastic region (relaxed) =

$$(100 \text{ mm} + 100 \text{ mm} + (100 \text{ mm} \times 2))/4 = 267 \text{ mm}$$

Examples 1 and 2 above illustrate that the width of the open elastic area may be adjusted by making small changes to the applied extension of the elastics and to the dimensions of the conveyor assembly. In certain designs, the tension is determined by the feed rate of the elastic strands into the spin head and the frictional characteristics of the feeding and spinning process. The circumference can be varied mechanically by changing the distance between the upper and lower conveyors.

Notably, the elastic composite 1210 is characterized by mutually spaced apart, cross-directional elastic elements 1201 that extend laterally between the first and second carriers 121, 1213 and in transverse relation with the machine direction of the elastic composite (LL). Each of the layers 1202, 1203 of the carriers 1212, 1213 preferably extends generally longitudinally in generally parallel relation with the machine direction LL and has a lateral width that is substantially less than a lateral width between the first and second carriers 121, 1213 (across the open elastic region 1204). In a further aspect, the elastic elements 1201 of the open central elastic region 12104 are "discrete disconnected segments of one elastic strand". This means that the elastic elements 1201 originate from the same elastic strand and are, in fact, severed sequentially from the same elastic strand while that strand is in a generally uniform state of tension or application (e.g., secured in tension between adhered nonwoven layers). Being discrete disconnected segments of one elastic strand further means that the elastic elements have substantially identical material and mechanical properties (particularly, dimensions, strength, and elastic properties). The inclusion of such elastic elements can offer benefits in the ultimate elastic composite as well as the processes in the making of the elastic composite. For example, having uniformity and consistency in the plurality of elastic elements facilitates handling of the elastic composite, provides a cleaner and more aesthetically pleasing gathering in the ultimate disposable absorbent article, and may also produce a better quality product with less flaws.

Applications—Post Processing

A variety of applications for the cross directional elastic composite 1210 and output composite 1303, O1 described above are contemplated. These applications include direct incorporation of the elastic composite 1210 (having the open elastic region) as a component in a disposable absorbent article and particularly, into a process of making the article. For example, the elastic composite 1210 may be integrated as a wide elastic waistband of a diaper type product. The elastic composite 1210 may also be applied as a body encircling elastic component for training pants.

Figure 15:
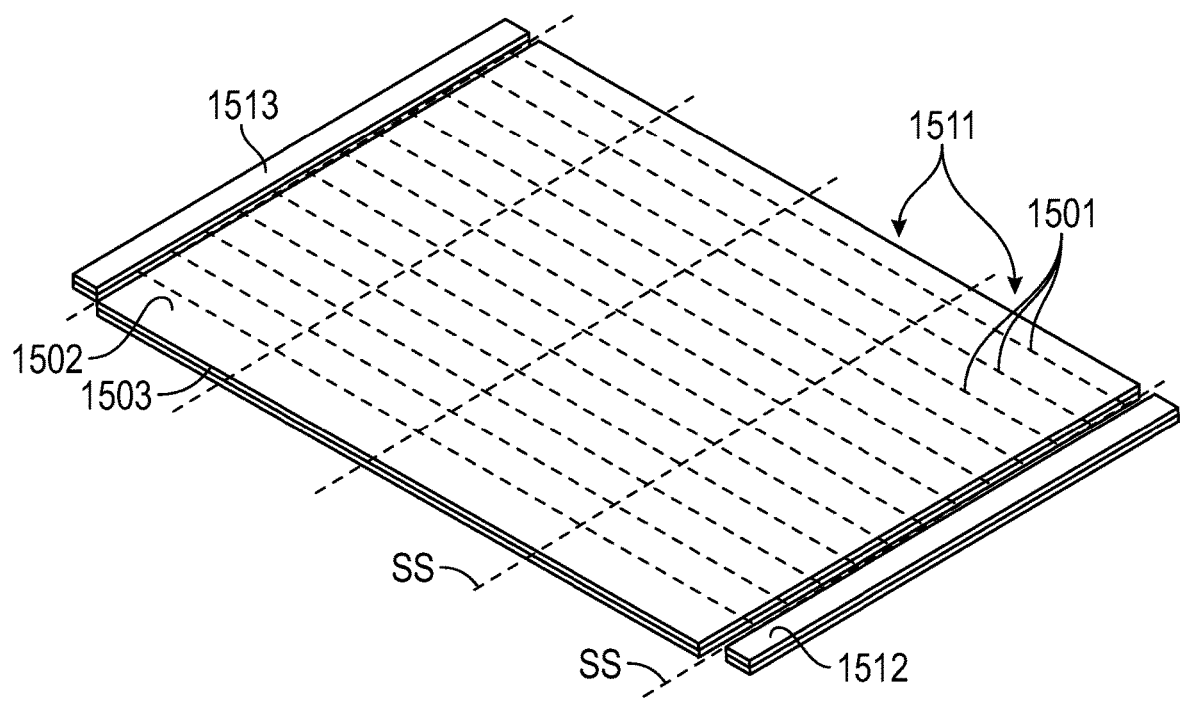
FIG. 15 is a simplified illustration of yet another elastic composite.
Figure 16:
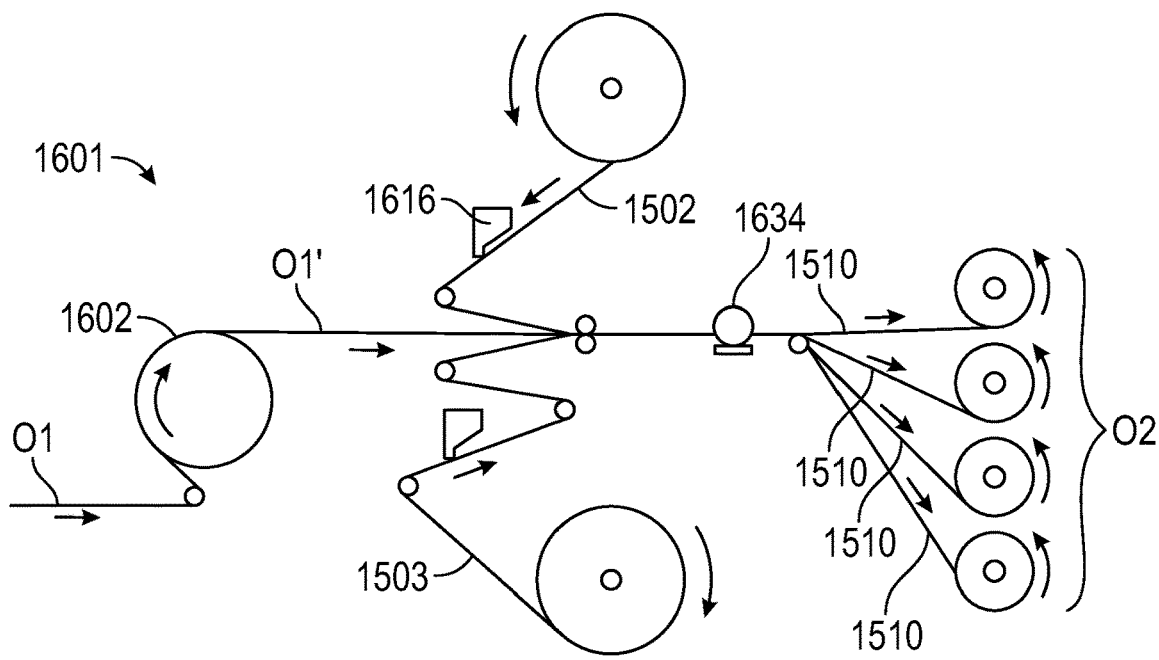
FIG. 16 is a simplified system and process illustration of making the elastic composite in FIG. 15.

A cross directional elastic composite with open elastic region is also well suited for further processing prior to integration into a disposable absorbent article. FIGS. 15 and 15A depict an exemplary product of further processing of elastic composite 1310. FIG. 15A depicts an elastic composite in the form of an elastic laminate 1511 derived from a method according to an embodiment of the disclosure. The laminate 1511 includes an upper nonwoven layer 1502, a lower nonwoven layer 1503, and a plurality of tensioned elastic elements 1501 sandwiched therebetween. The laminate 1511 further includes first and second carriers 1512, 1513 serving as the side borders of the laminate 1511. The elastic laminate 1511 may yield, in turn, several multi-layered, cross directional elastic composites 1510. These elastic composites 1510 are also in a form that is particularly suited for further processing and ultimately, for fastening tape and elastic side panel applications. FIG. 16 illustrates an exemplary system 1601 and process that receives the elastic composite web output O1 and further processes the web O1 to produce the elastic laminate 1511 and the multilayered elastic composites 1510. In particular, the exemplary system 1601 and process illustrates the flexibility of various embodiments of the disclosure to create cross-directional elastic sheet materials of varying width.

Figure 17:
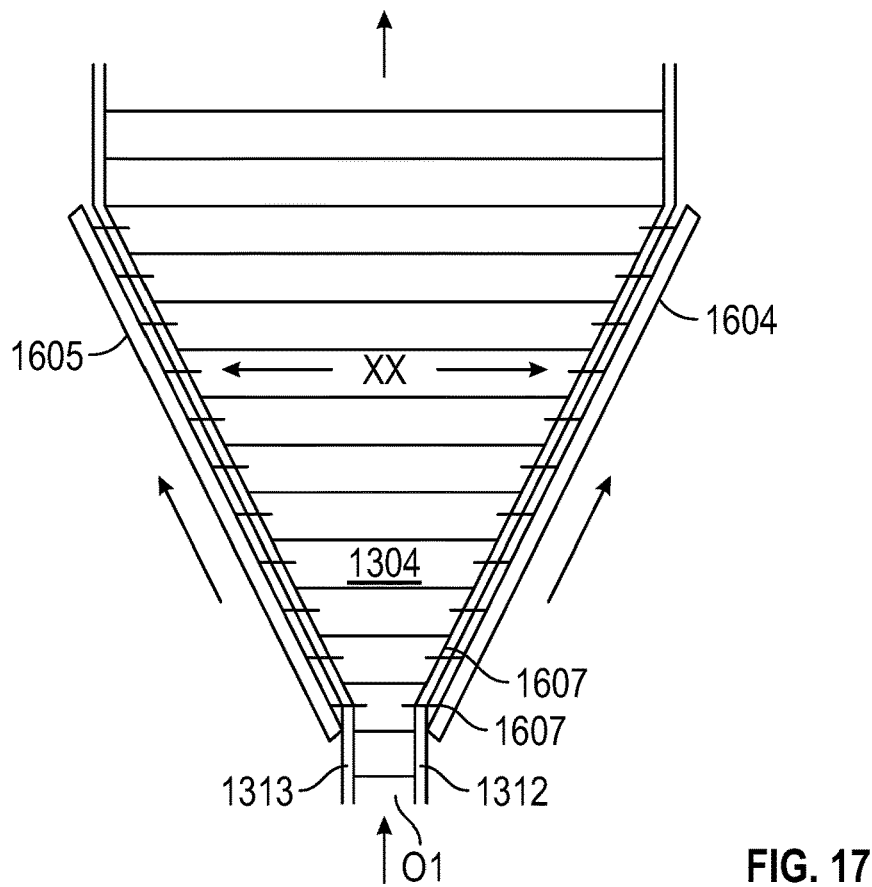
FIG. 17 is a simplified illustration of an extender subsystem suitable for use with the system and process illustrated in FIG. 16.

In accordance with one method, the output O1 (continuous web of elastic composite 1310) of system 1350, as described in respect to FIG. 13, is received by the present system 1601 and more particularly, by a conveying device, referred to hereafter as extender 1602. The extender 1602, shown in further detail in FIG. 17, secures the continuous web O1 along each carrier 1312, 1313 and stretches the open elastic region 1304 to a desired width, while moving the web O1 forwardly in the system 1601. The extender 1602 includes a pair of identical reciprocating components 1604, 1605. The reciprocating components 1604, 1605 may employ a wheel, belt or chain based system to reciprocate. As shown in FIG. 17, the two reciprocating components 1604 are situated upright and spaced apart from another at an angle such that a lateral space XX between the two expands along the web moving direction. The reciprocating components 1604, 1605 are adapted with engagement means 1607 for securing the web O1 preferably at the carriers 1312, 1313. The engagement means can be found in the form of pins, mechanical grips, or the like. The web O1 is stretched as the web O1 is moved forwardly between the two components 1604, 1605 and as the lateral space XX expands. In this way, the extender 1602 extends the width of the open elastic region 1304 to a target width, and carries the elastic web O1 from its original relaxed state to a desired extended or tensioned state (O1').

The tensioned elastic composite O1' is then fed to a laminating stage, wherein a lower nonwoven web 1503 is continuously directed to the web O1' from below and an upper nonwoven web 1502 is continuously directed to the web O1' from above. Prior to reaching the web O1', hot melt adhesive is applied to each of the nonwoven webs 1502, 1503 using suitable adhesive application equipment 1616. Thereafter, the lower nonwoven web 1503 is applied to the "underside" of open elastic region 1504' of the web O1' and the upper nonwoven web 1502 is applied to the "topside" of the open elastic region 1504'. The applied adhesive ensures proper bonding between the nonwoven layers and the tensioned elastic elements. The resulting laminate 1511 includes, therefore, an upper nonwoven layer 1502, a matching lower nonwoven layer 1502, 1503, a pair of carriers 1512, 1513 providing the side borders of the laminate 1511, and a plurality of mutually spaced apart elastic elements 1501 extending between the carriers 1512, 1513 and sandwiched between the nonwoven layers 1502, 1503. As compared to the output web O1, the elastic elements 1501 are now in an extended state, but remain laterally oriented, thereby imparting cross-directional elasticity to the laminate 1511.

Notably, the two carriers 1512, 1513 serve a handling function during the process. The carriers 1512, 1513 ensure that the configuration of elastic elements is maintained as the webs O1, O1' are processed. The carriers 1512, 1513 also provide a solid base for the components of the system 1601 to secure and handle (e.g., convey and stretch) webs O1, O1'.

As shown in the exemplary diagram of FIG. 16, the resulting laminate 1611 is directed forward to a slitting mechanism 1634. In this embodiment, the slitting mechanism(s) includes five slitters that sever the carriers 1512, 1513 from the laminate 1511 and slits the laminate 1511 into four separate webs of yet another cross-directional elastic material or multilayer elastic composite 1510 according an embodiment of the disclosures. The slitters 1634 are positioned in alignment with slitting lines SS along the web O1'. In this embodiment, the set of five slitting lines SS is equally spaced apart and include slitting lines SS adjacent the carriers 1512, 1513. As a result, the slitters 1634 divide the laminate 1511 into four separate but identical webs O2 of cross directional elastic composite 1510. Each of the four webs O2 is then directed as web output O2 to a reel or spool. Further, the web output O2 of elastic composite 1510 may be packaged for easy handling and for further processing, or fed directly into a manufacturing process.

Elastic Composites Having Dead Zones

The preferred elastic composite may be equipped with a pair of non-elasticized regions or dead zones, the utility of which has already been described. As generally known, the dead zones are preferably situated on either lateral side of a central elastic region having an elastic construction (as discussed previously). Various ways are envisaged to create the dead zones within methods of making the elastic composite according to the disclosure. In one exemplary method, an adhesive pattern is applied to the nonwoven web input. The adhesive pattern is selectively applied so that adhesive is provided only to areas of the nonwoven web wherein the elastic strands are to be retained.

Figure 18:
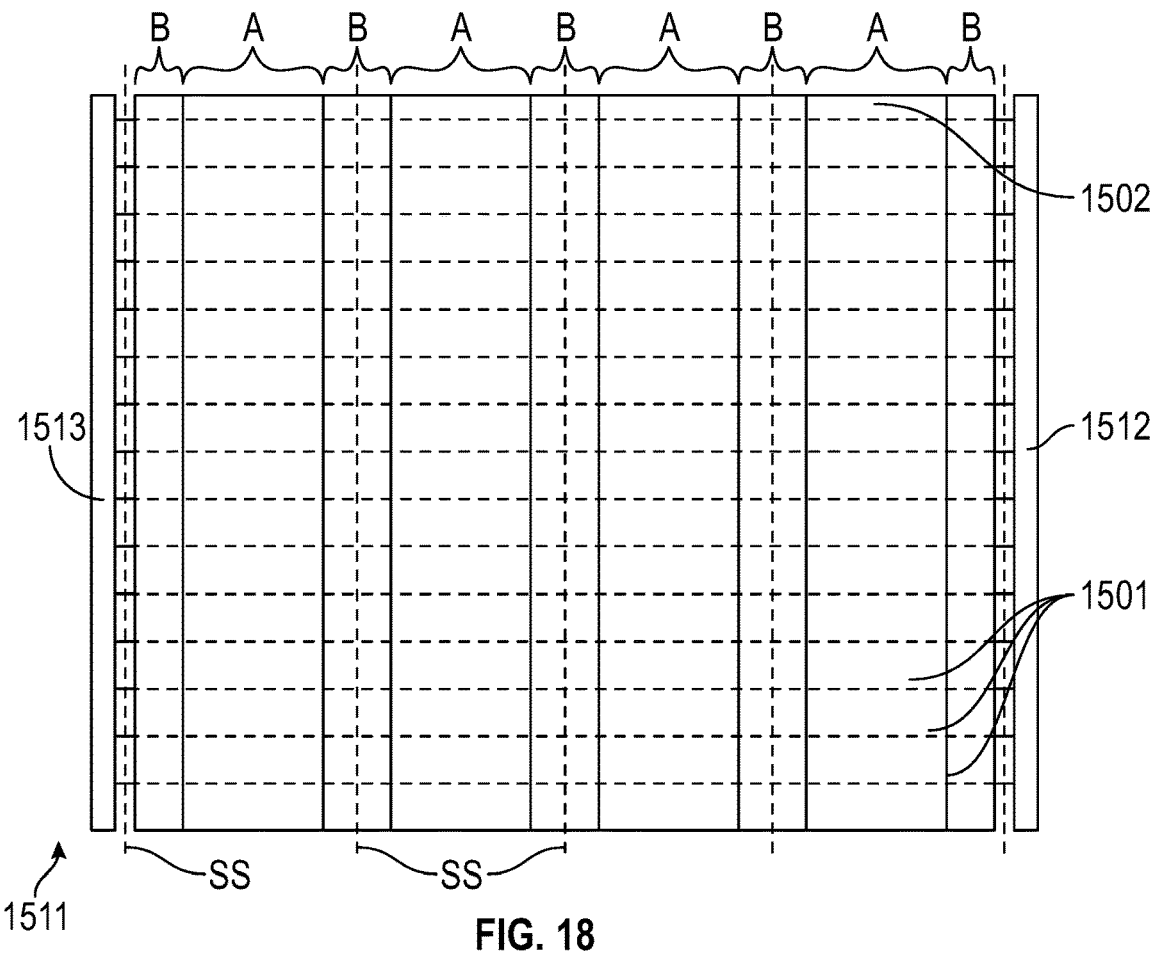
FIG. 18 is a simplified illustration of yet another elastic composite in the form of an elastic laminate.

To illustrate, FIG. 18 shows an elastic composite laminate 1511 generated by a process such as that described above in respect to FIG. 16 and in a stage prior to passage of the web of the laminate 1511 through a set of slitting mechanisms. Tensioned elastic elements 1501 are sandwiched between the upper and lower nonwoven webs 1502, 1503 and extend between the carriers 1512, 1513. In this example, adhesive is applied only to prescribed areas of nonwoven webs 1512, 1513 ("adhered areas"), which areas are indicated as shaded areas A in FIG. 18. The adhesive application means 1616 described previously are precisely positioned over the path of the webs 1512, 1513 that correspond to the shaded areas A and operated to apply adhesive only to these areas A. The areas between the shaded areas A (i.e., "non-adhered areas" indicated as un-shaded areas B in FIG. 18) in the resulting laminate 1511 are clear of adhesive such that the portions of the elastic elements 1501 found therein remain loose. As indicated by slitting lines SS, slitting mechanisms provided downstream are aligned with the center of these non-adhered areas B. As the web of the laminate passes the slitters, the elastics in the non-adhered areas B are cut. Furthermore, the non-adhered areas B are divided into two sections. Each half section provides, thereafter, one non-elastic or dead zone of the multi-layered elastic composite 1510.

In the illustrated design, a non-adhered area B is located adjacent each of the two carriers 1512, 1513 and a slitting line SS is aligned along the inside of the carrier 1512, 1513. As a result, the carrier 1512, 1513 is cut and removed from the web during the slitting process. The formerly adjacent non-adhered area B remains as a dead zone of the resulting cross-directional elastic composite.

Figure 19:
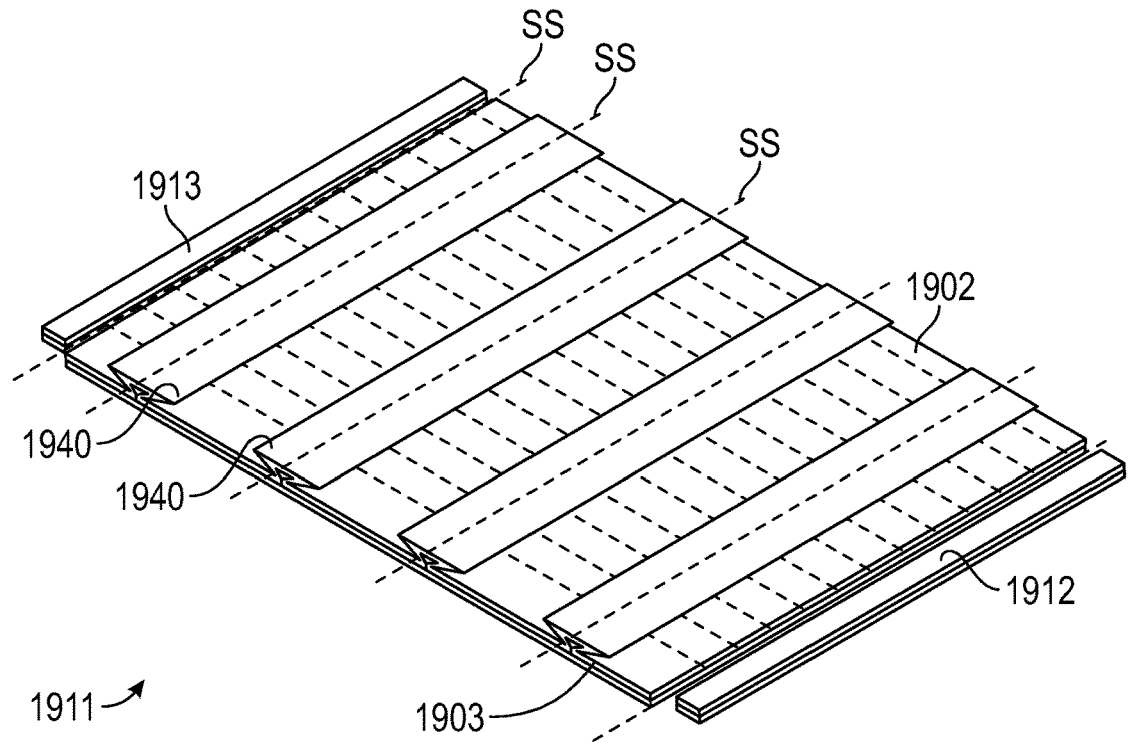
FIG. 19 is a simplified illustration of yet another elastic composite in the form of an elastic laminate having pre-folded sections.

FIG. 19 illustrates yet another laminate 1911 (an elastic composite). The illustrated laminate 1911 helps explain an alternate method of making a cross directional elastic composite featuring a pair of dead zones and a central elastic region therebetween. According to this method, the step of applying an upper (or lower) nonwoven web 1902 is modified by providing several folds 1940 in the nonwoven web 1902. A suitable folding sub-process is one substantially equivalent to the sub-process described in respect to FIGS. 6-10, and are now known in the art. The web 1902 is pre-folded to provide an excess folded section 1940 in the tensioned elastic composite O1' and in the resulting laminate 1911, as shown in FIG. 19 for the use of multiple folding boards. A slitting line SS may be aligned with the center of each folded section 1940 much in the same manner as described above in respect to FIG. 18. In the slitting step, each folded section is divided into two separate folded sections and the elastic elements beneath the fold are severed. For each resulting individual elastic composite, the two folded sections are then unfolded to reveal dead zones on each side of a central elastic region.

FIG. 13D depicts an alternative system that employs or receives into the conveyor assembly 1309 two additional input webs of non-woven (I3 and I4) to double the output of the inventive system and process as described previously in respect to FIGS. 13A-C. As before, non-woven web input I1 is initially directed in between the upper and lower conveyors 1314, 1315, before being redirected and conveyed atop the upper conveyor 1314 whereon it receives the spun elastic WW. Then, the second nonwoven input I2 is applied over the transversely applied elastics WW and nonwoven input I1. Nonwoven input web I3 is also directed in between the upper and lower conveyors, in a manner similar to the conveyance of I2. The non-woven input I3 is, however, redirected and conveyed upon the lower conveyor 1315. With the nonwoven input I3 moving in the reverse direction on the lower conveyor 1315, the spin head 1317 applies elastic WW onto and about both conveyors 1414, 1315 and both I1, I3 during each revolution. With the elastics applied generally transversely thereupon, the fourth feed of nonwoven I4 is applied to the sub-composite of the non-woven I3 and elastic elements. Two multi-layer elastic composites or sandwiches are conveyed by the upper and lower conveyors 1314, 1315, respectively, while joined together by the continuous elastic strand WW. At this point, a slitter or other cutting mechanism 1334 placed in the path of each of the two composites preferably slits the composite centrally, thereby producing two separate but substantially identical carriers (as shown in FIG. 13D). With the slitters 1334 cutting the nonwoven webs centrally on the upper and bottom conveyors, the two resulting webs of elastic composite outputs O1, O2 conveniently slides to either side of the conveyor assembly 1309 and is received for further processing.

Figure 20A:
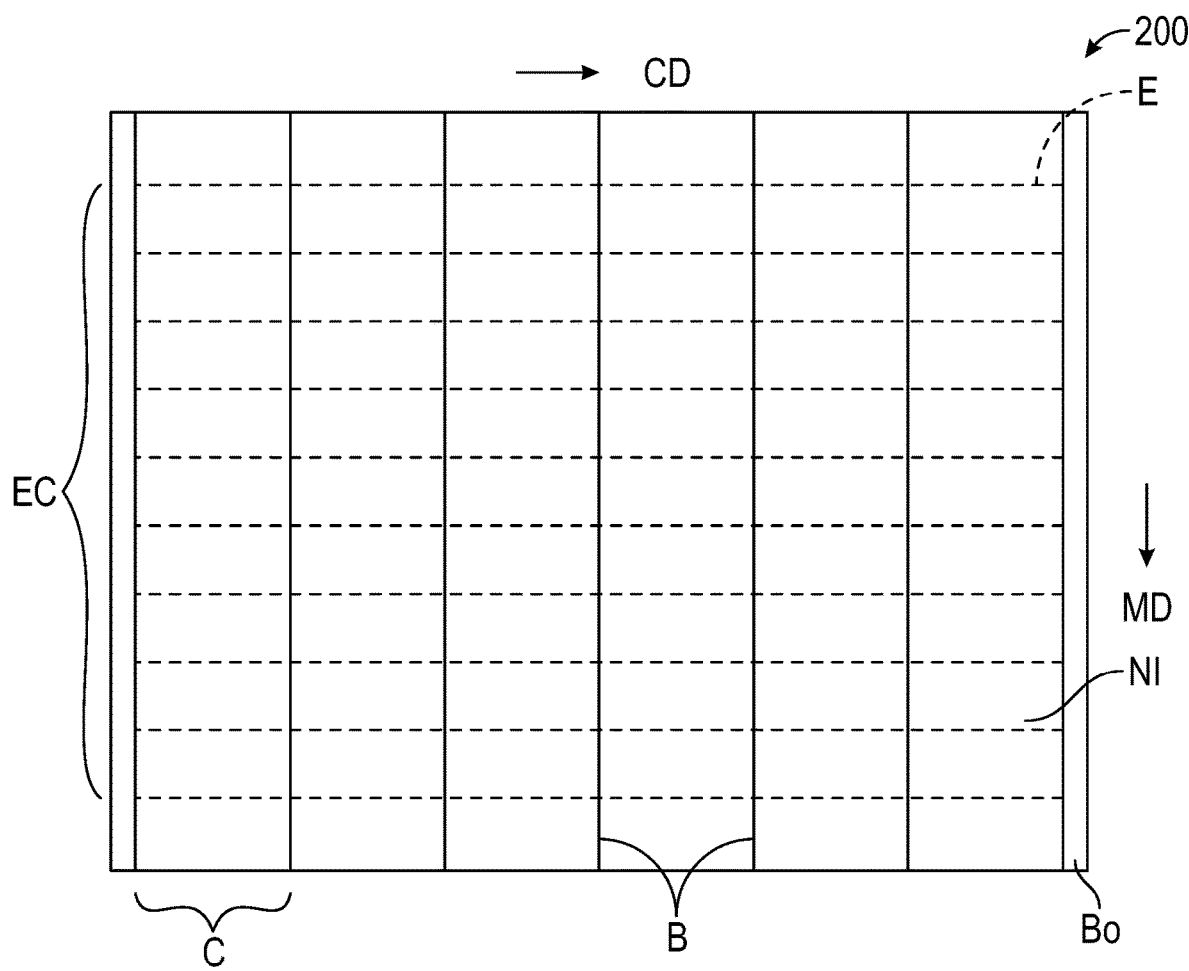
FIG. 20A is a simplified illustration, in plan view, of an exemplary elastic core assembly, according to the present disclosure.
Figure 20B:
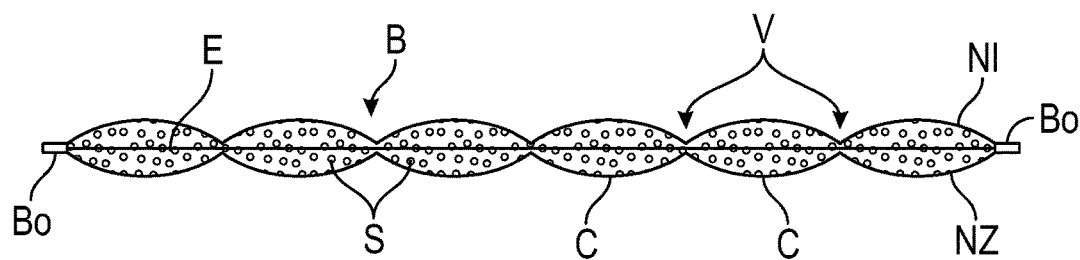
FIG. 20B is a simplified illustration, in cross-sectional end view, of the exemplary elastic core assembly in FIG. 20A, according to the present disclosure.

In some respects, FIGS. 20-38 illustrate an elastic absorbent assembly (or the making of) that is made by a process that borrows from or employs modified aspects of the methods earlier described of making the elastic composite of FIGS. 13-19. Moreover, certain aspects unique to the present disclosure may be readily merged with or practiced in conjunction with at least parts of systems, methods, and products previously described. In accordance with the present disclosure, an elastic absorbent assembly is provided particularly suited for incorporation into a disposable absorbent garment. Referring first to FIGS. 20A and 20B and in accordance with one embodiment, the elastic absorbent assembly 201 has a top layer N1, a base layer N2, and an elastic construction EC disposed in between, or sandwiched by, the top and base layers N1, N2. (MD) In FIG. 20, the elastic construction EC is composed of plurality of spaced apart elastic elements E (hidden but represented in dash lines) forming, with the base and top layers N1, N2, a plurality of encapsulating spaces or preferably elongated capsules C, wherein absorbent material S is disposed. "Encapsulating"—has defied void space between N1 wherein materials such as a.m. may be retained. Preferably, the top and base layers N1, N2 are nonwoven and the absorbent material includes, but is not limited to, superabsorbent polymer particles S.

The elastic absorbent assembly 200 may be provided as the product of a sub-process (of making elastic absorbent assemblies) and delivered or merged with a process of making a disposable absorbent article. For example, the elastic absorbent assembly 200 may be delivered onto a chassis for an unfinished diaper 201 prior to application of a topsheet over the elastic core assembly 200. Preferably, the elastic absorbent assembly 200 is delivered as a self-supporting core construction with the capsules C confining SAP therein and the side edges (at B0) and end edges of the assembly sealed or otherwise secured to prevent SAP escape during manufacturing. See elastic core assembly 200 with the outline or contour of longitudinally directed SAP-containing capsules C shown in each of FIGS. 2, 2A-2C.

As shown, the elastic construction EC is preferably provided by a plurality of spaced apart elastic filaments E, strands, and the like. The filaments E are preferably secured to one or both of the top and base layers N1, N2 at spaced apart or intermittent bond sites or points B, thereby forming the encapsulating spaces C. The bond sites B may be effected using adhesives, ultrasonic bonding, heat induced bonding, embossing and the like. In the core construction or assembly, the elastic filaments E are directed transversely to the direction of the elongated encapsulating capsules C, which direction of the elastic elements being the lateral and cross-machine direction CD and the direction of the capsules being the longitudinal and machine direction MD. Accordingly, the elastic core assembly 201 may be described as being cross-directionally elasticized due to the elasticity of the filaments E. Between the bond sites B mutually securing the top and base layers N1, N2 and the elastic filaments E, the two layers N1, N2 may be un-bonded or bonded. Thus, the two layers N1, N2 may be bonded continuously at laterally spaced, preferably continuous bond lines B that also hits or crosses most, if not all, of the spaced apart elastic filaments E at the aforementioned bond points B.

In the embodiment of FIG. 20, adhesive is applied linearly and continuously to adhere the layers N1, N2 substantially continuously, including at and with the elastics E at the mutual intersection of the three elements (E, N1,N2). A plurality of said continuous bond lines B are disposed spaced apart in the lateral or cross direction, which spacing generally dictates, at least in this embodiment, the width of each capsule C. See also FIG. 20B. At the longitudinal side edges or margins of the composite 200, the nonwoven layers N1, N2 are also secured or sealed by a bond B0 (preferably by adhesive or ultrasonic bonding). As further described herein, such adherence between the elastics E and one or both layers N1, N2 may be effected while the elastics C are in an extended or stretched mode. As the elastics E relaxes, the adhered layer(s) shirrs and the capsule C may sag or bulge outwardly (above or below according to the view of FIG. 20B) with excess material. With the elastics E secured intermittently to both layers N1, N2 and the bond lines B continuously attaching to the layers N1, N2 together, the capsules C have a rounded cross section. The capsule C also takes on an elongated, almost tubular shape.

Furthermore, the spaced apart bond lines B and top layer N1 form valleys V between the capsules C and above the shirred nonwoven layer N1. In further embodiments, one or more of the valleys V may be deposited with absorbent material that may or may not be the same as the absorbent material S situated in the capsules. In further embodiments, only the valleys near the center of the core assembly C and\or in the target receiving areas of the diaper, such as the center and near, rear center of the crotch region of the diaper 200, may be deposited with additional absorbent material (i.e., SAP). In further embodiments, another sheet layer is provided over the top layer N1 and the valleys V thereon. This creates additional encapsulating spaces for absorbent material.

Figure 21A:
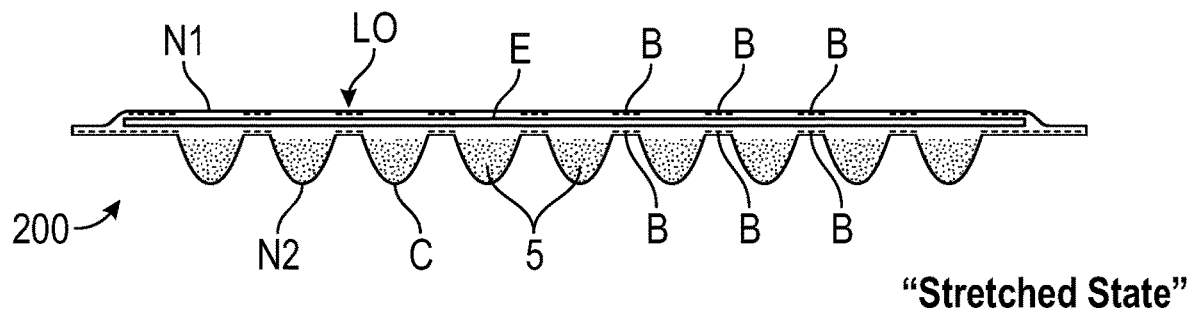
FIGS. 21A-21C are simplified illustrations, in cross sectional end view, of alternate elastic core assemblies, according to the present disclosure.
Figure 21B:
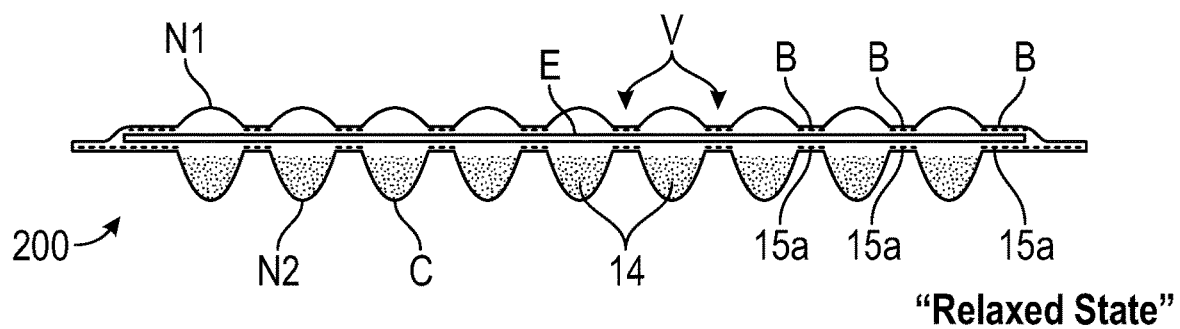

FIGS. 21A and 21B provide an end cross-sectional view of another embodiment of the elastic core assembly 200, wherein like reference numerals are used to indicate like elements. Elastic E is secured to each of a top nonwoven layer N1 and a base nonwoven layer N2 at bond sites B. Elongated capsules C are formed between longitudinally aligned series of bond sites B. The capsules C are provided with SAP that initially fills at least the void of the capsule C below the elastic. Advantageously, the capsule C has sufficient capacity, and void space, to allow for expansion of the SAP aggregate S during liquid intake. The additional void space is typically provided at the upper part of the capsule C, as most SAP particles S fall and rest on the bottom nonwoven layer N2. In the embodiment of FIGS. 21A-21B, the bond sites are generally wider and correspond to SAP-free lanes L0 (during the process of making the composite). Also, the resulting valleys V are wider and flatter, and can accommodate more absorbent material for storage as needed.

FIG. 21A illustrate the state of the elastic core assembly 200 upon securement of the elastics E with the top and base layers N1, N2. The elastics E are in a stretched state, while the top layer N1 is in an extended, generally flat state. The base layer N2 may also be referred to as being in a relatively stretched state, but, in this embodiment, is wider (in lateral direction) than the top layer N1 and provided with greater slack. Even in the stretched state, the base non woven layer N2 has sufficient slack to bulge downward and create void space for the capsule C. This void space accommodates the SAP particles S below elastic E. When the elastics E are released and then reverts to a relaxed state, as illustrated in FIG. 21B, the top nonwoven layer N1 contracts and urges material upwards. This action creates more void space above the elastic C and presents an upper bulge to the capsule C. As well, valleys V are formed between the capsules C. During wear, the elastic core assembly 200 may take on a slightly stretched profile or configuration, somewhere between FIGS. 21A and 21B.

In further embodiments, the different capsules C may vary in size or SAP capacity. For example, the capsules C in the central region may be made wider (than capsules outward thereof) due to greater lateral spacing of the bond sites B. The capsules C in the central region may be provided with greater capacity due to a wider exposure of nonwoven material N1, N2 and greater slack in the reduced N1, or L. Furthermore, the larger cells may be deposited with greater volume of absorbent material. Further yet, certain of the capsules may be deposited with different constituents having differing properties, as further described below.

Figure 21C:
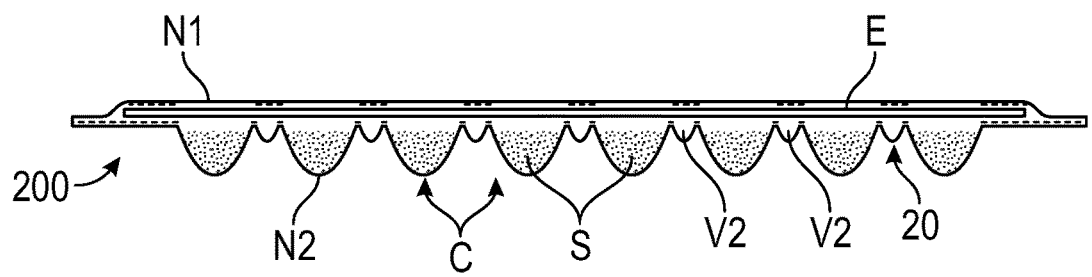

FIG. 21C provides an end cross-sectional view of another embodiment of the elastic core assembly 200, wherein like reference numerals are used to indicate like elements. In this embodiment, two (or more) space apart bond sites B1 are provided to secure the base layer N2 (or top layer N1 in other embodiments) to the elastics E and top layer N1. The spaced apart bond sites B1 are preferably continuously extending bond lines (such as adhesive) and form an unsecured gap over the SAP-free lanes L0. After bonding the base layer N2, top layer N1, and elastics E together, tension on the elastics E is released. The relaxing elastics E contracts the top layer N1 and base layer N2, as shown in FIG. 21C. The material of the base layer N2 contracts and gathers at the gap to form void spaces V2 that, together, provide channels or tubes V2 extending adjacent and parallel with the capsules C. Notably, these channels provide SAP-free and hot-melt free passages for fluid flow. In certain embodiments, the tubes V2 may be of a dimension suitable for capillary flow to promote transport of fluid in the longitudinal direction of the core assembly.

In the embodiment of FIG. 21C, the elastics E and the nonwoven layer N1 are bonded with solid bonds, B2 in the gap or SAP-free lanes L0. The bonds B2 may, however, be placed of spaced-apart bond points such as the bond points B1.

Figure 22A:
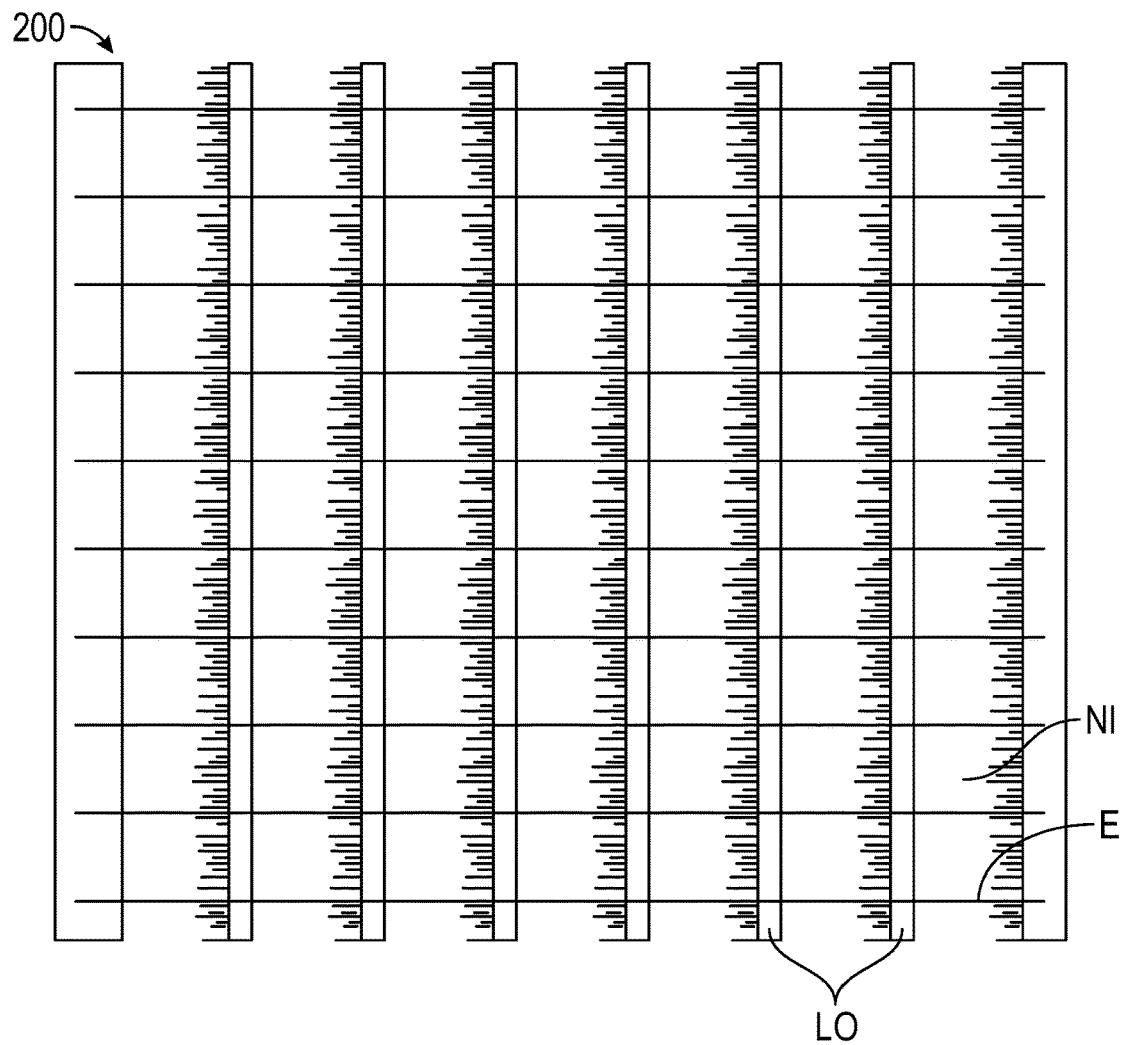
FIGS. 22A-22C are simplified illustrations of alternative elastic core assemblies, according to the present disclosure.
Figure 22B:
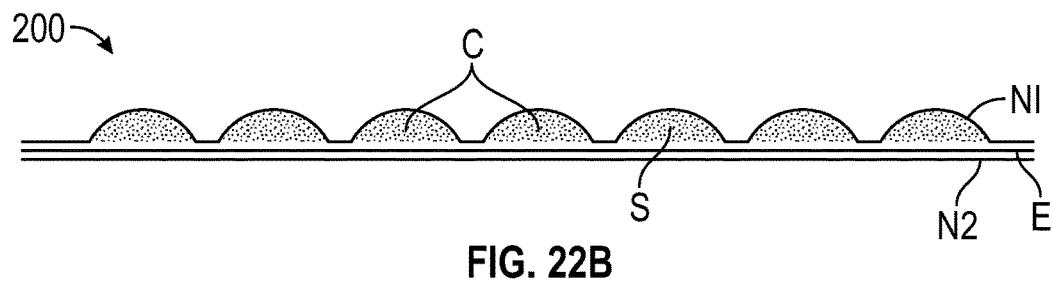
Figure 22C:
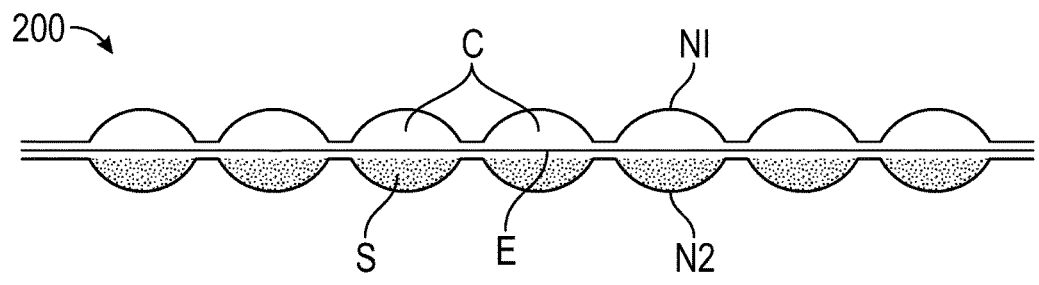

FIGS. 22A-22C illustrates another embodiment of an elastic core assembly 201, according to the present disclosure, wherein like reference numerals are used to indicate like elements. The plan view of FIG. 22A shows the continuous bond line B, preferably provided by strips of adhesive, and the resulting wider SAP-free lanes L0. In this embodiment, the base or bottom nonwoven layer N2 is secured to the elastic E while in an extended and generally flat state (as opposed to the top nonwoven layer N1 being so). The end cross-sectional view of FIG. 22B shows the profile of the elastic core assembly 200 in the stretched state, wherein the base layer N2 is flat but the slacked top layer N2 provides a void space for SAP storage. FIG. 22C then shows the profile of elastic core assembly 200 in the relaxed state, as commonly found when the diaper 201 is opened and ready for wear. During wear, the elastic core assembly 200 may be take on a slightly stretched profile or configuration, somewhere between FIGS. 22A and 22B.

Figure 23:
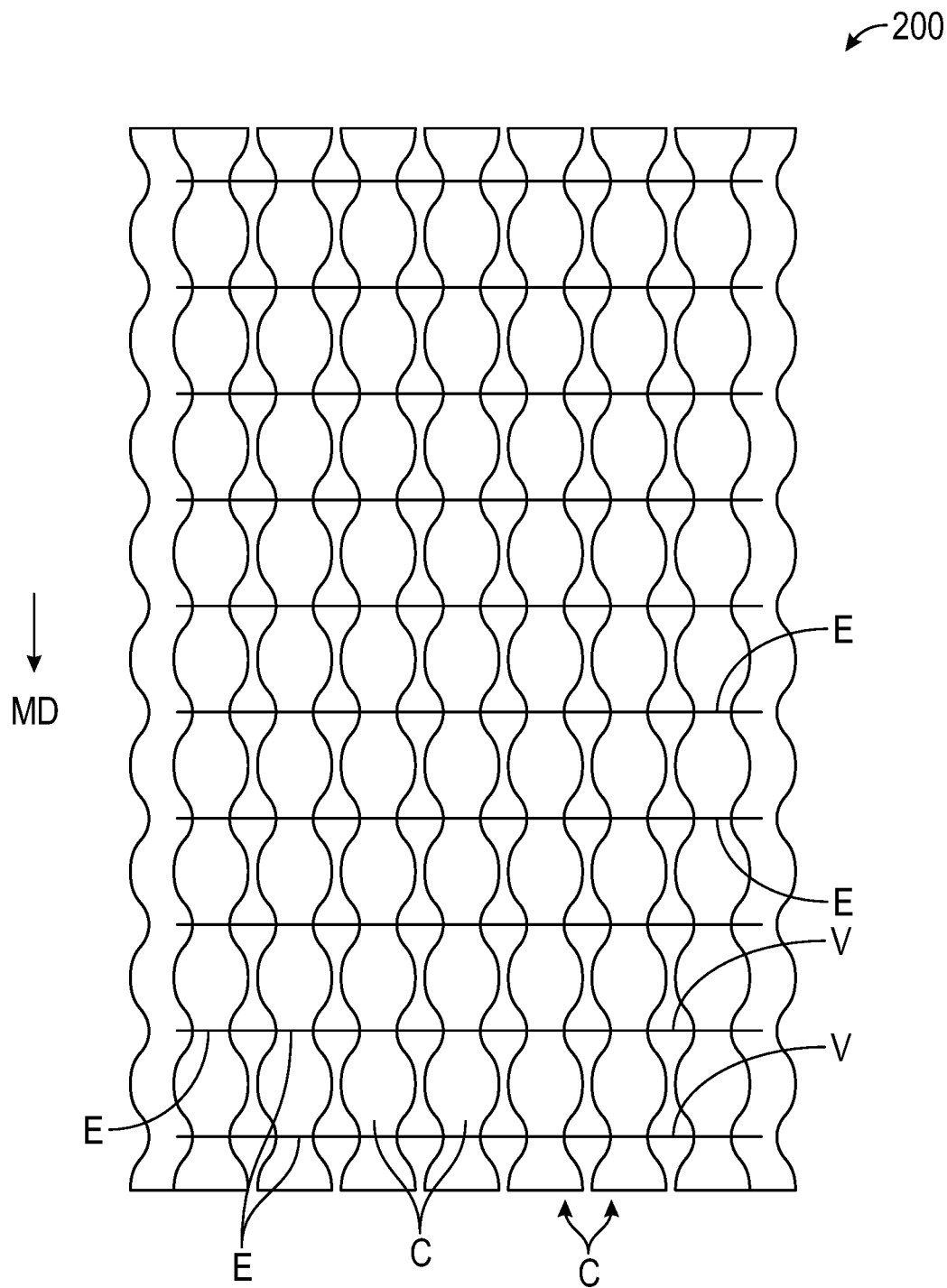
FIG. 23 is a simplified illustration, in plan view, of yet another exemplary elastic core assembly, according to the present disclosure.

FIG. 23 is a plan view of an alternate embodiment of an elastic core assembly 201 according to the present disclosure, wherein like reference numerals are used to indicate like elements. In this embodiment, the nonwoven layers N1, N2 are not secured continuously along a longitudinal bond line. Instead, the nonwoven layers are secured only at bond sites B0 with elastics E. As a result, the capsules C are generally open to adjacent capsules and in fluid communication therewith. Fluid and SAP can, therefore, travel laterally (as well as longitudinally) from capsule C to capsule C, except at the bond sites B. In the plan view, valleys or depressions V are shaped nearly circular or even near diamond shape at and about the bond sites or bond points B. In comparison to the other embodiments, the capsules C are less defined, at least in the machine or longitudinal direction. The capsules C are not isolated and segregated from one another, as illustrated in FIGS. 20-22, and there is fluid communication and travel in the lateral direction. In one respect, a fluid channel is created in the cross direction and between spaced apart elastics. In another respect, the capsule C may also be characterized functionally and structurally as being directed laterally or both laterally and longitudinally. In yet another characterization, the capsules C may be characterized as being replaced or being comprised of individual cells or pockets C'. Each of these pockets C' are substantially open and bounded (and formed) by four spaced apart bond sites or points, and two segments of elastics.

An elastic absorbent assembly or composite according to various embodiments supports and maintains absorbent materials at desired locations on the diaper 201. The absorbent material is primarily and preferably superabsorbent particles and additives that are confined between facings provide by sheet materials (i.e., nonwovens) and with elastic filaments or strands arranged within the assembly to provide stretch and recovery to the composite. Each strands is intermittently attached to at least one of the top layer and the base layer at spaced apart attachment points along the length of the strand such that attachment of the plurality of elastic strands with the top or bottom layer at said attachment points form spaced apart ridges between pairs of spaced apart attachment points. The elastic filaments are arranged appropriately to provide CD-stretch, MD-stretch or both MD and CD stretch.

Such an elastic absorbent composite has good flexibility, elastic stretch and garment-like properties that enables good fit with the body of the user. Features of the absorbent composite include creation of absorbent-containing tubes or capsules that can direct fluid along its length and absorbent-free channels that can allow fluid to flow along its length and hence provide another path for delivering the liquid to the absorbent material contained in the capsules. Additionally, composites with a surface topography that can be varied can be produced. Such topography can be produced by varying the spacing of the elastic filaments to vary the protrusion height established when the elastic is allowed to relax. The topography can be used to reduce side leakage, back or front waist leakage. For example, higher protrusions along the sides of the absorbent core can provide a barrier for side leakage. (See e.g., FIG. 32A). It is also contemplated to vary the absorbent loading is each channel to achieve a SAP profile that can enhance the leakage performance of an absorbent core made from this material. For example, an elastic core assembly with a profile providing higher absorbent content adjacent the side edges can reduce side leakage.

Figure 24A:
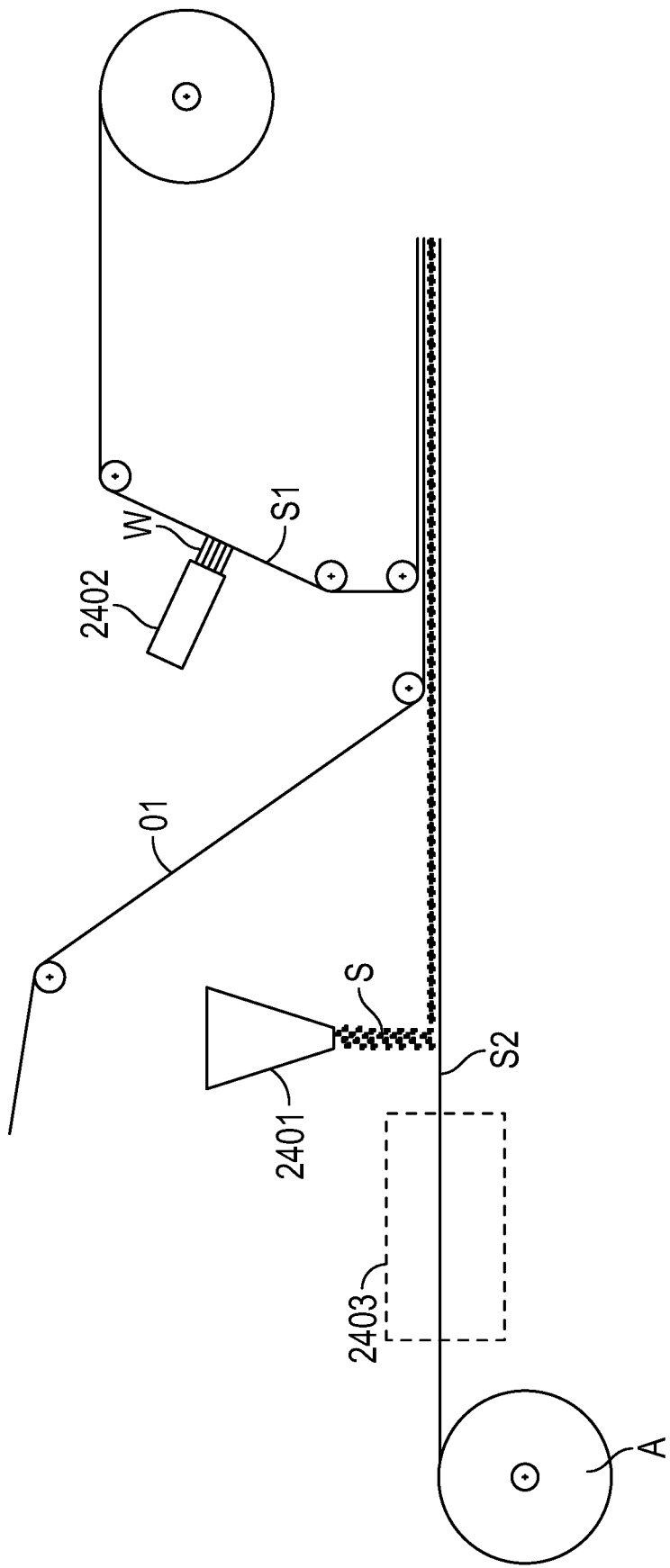
FIG. 24A is a simplified schematic of an exemplary system and method of making an elastic core assembly, according to the present disclosure.
Figure 24B:
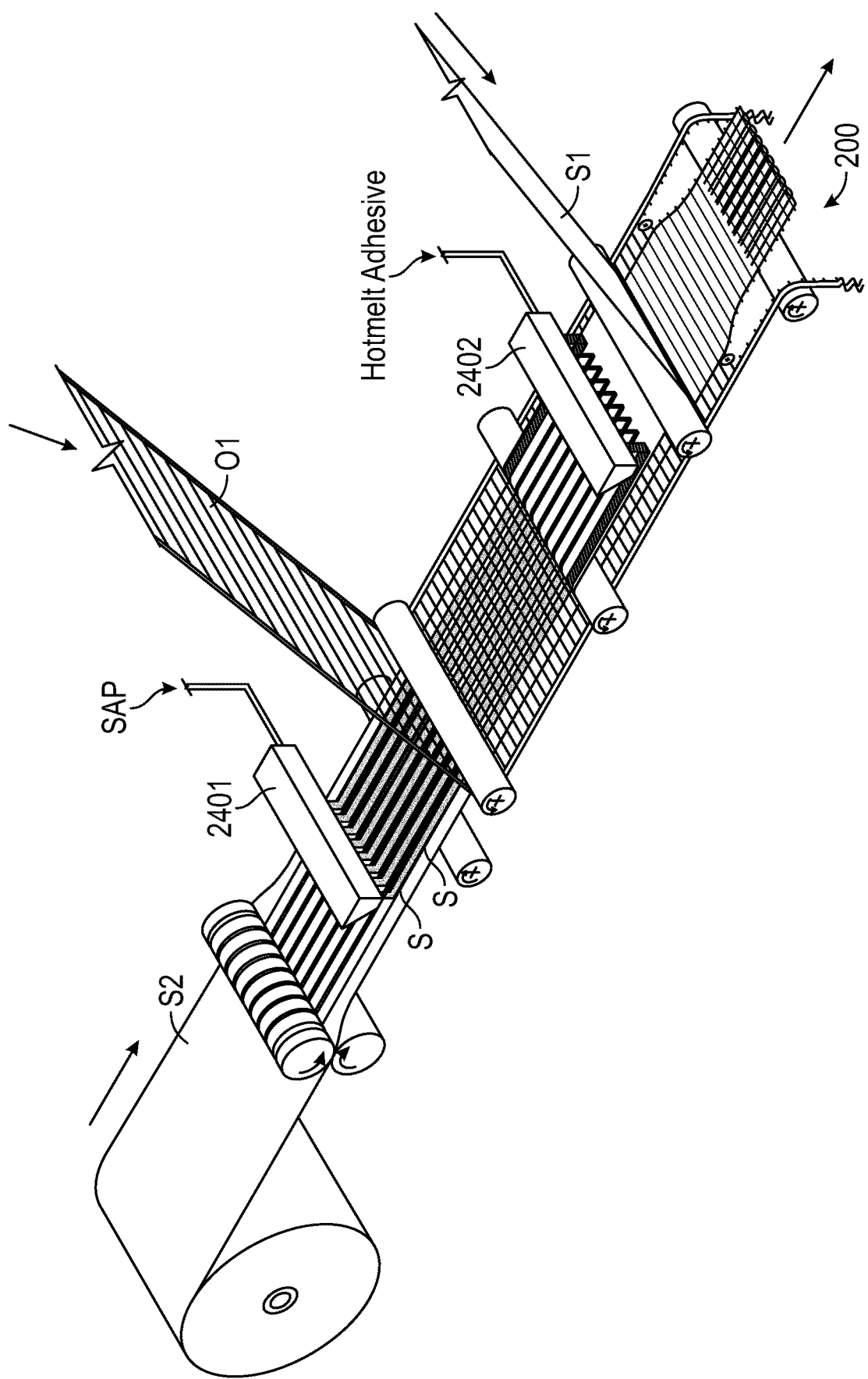
FIG. 24B is a simplified illustration and isometric of a system for making an elastic core assembly, according to the present disclosure.

The elastic core assembly may be formed in several ways. FIG. 24A is a simplified illustration of a system and method of making the elastic core assembly 200, according to the present disclosure. FIG. 24B is an isometric view of an exemplary system, in operation, for use in making the elastic core assembly (wherein like reference numerals are used to indicate like elements). The exemplary process entails conveying a shaped substrate S2 or web of nonwoven sheet N2, and depositing thereon, populations of absorbent material. The absorbent material is deposited onto one or more target locations on the moving substrate S2. In this embodiment, a hopper 2401 is employed to dispense and apply SAP particles S with the aid of gravity along spaced apart locations or lanes on the moving substrate S2. A web of an elastic composite O1 with spaced-apart elastic strands E is then applied over the SAP-supplied substrate S2. The elastic composite O1 is conveyed and applied while secured in a stretched or tensioned state and engages the substrate S2 of nonwoven N2 co-incidentally or linearly (i.e., moving along the same linear and planar direction at engagement), as shown also on FIG. 24B. Notably, the elastic composite is secured in tension and driven by way of the carriers (see earlier FIGURES and accompanying descriptions). After engagement, the plurality of elastics E are disposed in the cross-machine direction in the resulting elastic composite SO1 (of S2 and O1). See FIG. 24B. A second substrate S1 of nonwoven sheet N1 is then applied on the resulting un-finished elastic composite SO1 to produce the elastic core assembly SO2 formed with a plurality of capsules C.

The shape of the capsules C may be dictated, at least partly, by the manner and pattern by which the elastics E and nonwoven layers N1,N2 are mutually secured. In the process according to FIG. 24, an adhesive applicator 2402 is positioned to apply adhesive W to the moving substrate S1 at predetermined lanes, lines or spots, prior to the substrate S1 engaging substrate S2 and elastic composite O1. Referring to FIG. 24B, a multi-port adhesive applicator may be operated to apply lanes of hot melt adhesive W prior to the substrate S1 being rolled upon unfinished elastic composite S01. The resulting adhesive lanes coincide with SAP-free lanes L0 on substrate S2 and away from the lanes of SAP S. The resulting elastic absorbent composite SO2 remains tensioned as it moves forward from roller R2 and before moving past cutters K. The severing edges of cutters K are positioned inwardly of the carriers to cut through the elastic composite SO2, including through elastics E. As a result, the elastics E are released from the carriers and from tension, and the resulting elastic absorbent composite 200 contracts to finished form. As shown in FIG. 24B, the contracted elastic absorbent composite 200 is provided with a plurality of tube-shaped capsules C containing SAP.

Figure 27A:
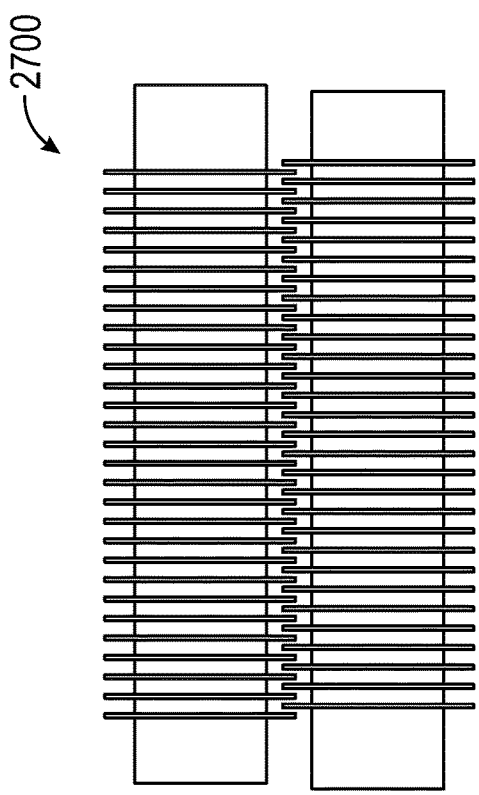
FIGS. 27A-27C are simplified illustrations of a set of rollers for corrugating a substrate for use in the elastic core assembly according to the present disclosure.
Figure 25:
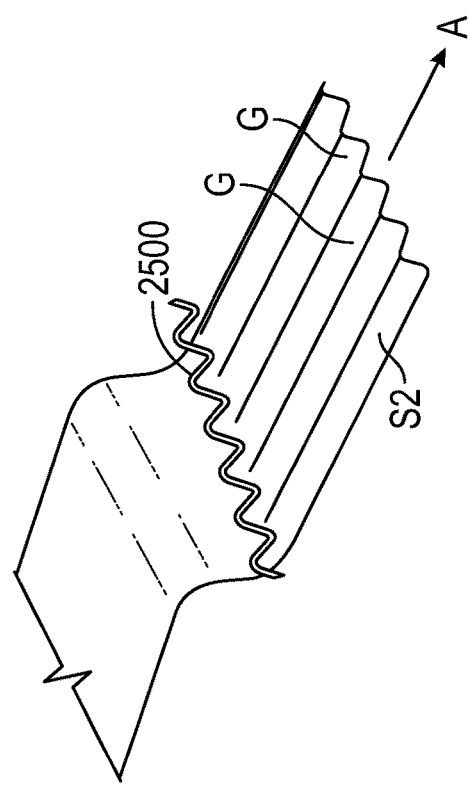
FIG. 25 is a simplified illustration, to accompany the schematic of FIG. 24, of a suitable sub-process of conforming a substrate for input into the process according to FIG. 24.
Figure 27B:
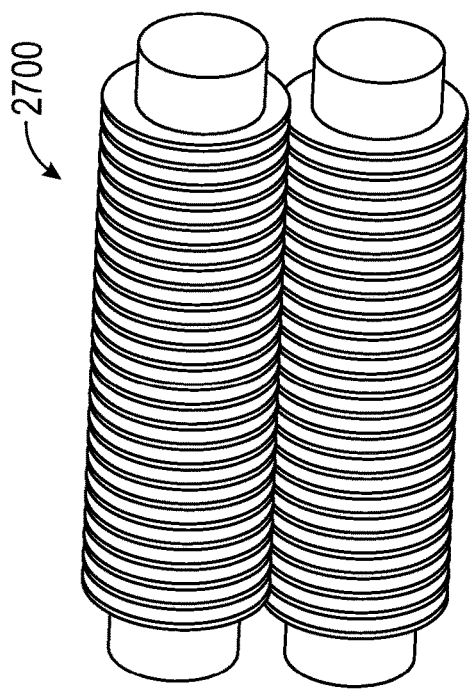
Figure 27C:
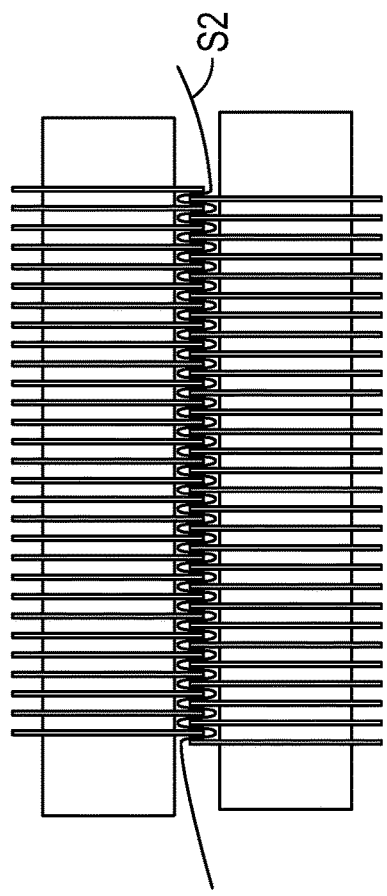

A primary but optional input (designated by Box 2403) to the process of FIG. 24 is a base nonwoven N2 that is shaped with longitudinally-oriented channels or grooves. The channels are shaped and positioned to receive the SAP particles. The substrate S2 may be shaped by folding, corrugating or having the sheet conform to a shaped surface. FIG. 25 illustrates such a sub-process of shaping and providing substrate S2 as input to the exemplary process. In this sub-process, the nonwoven substrates S2 is passed through a shaped plate or fingers that jut out and, by force, form corrugations on the passing substrate sheet. The sub-process FIGS. 27A-27C illustrates exemplary roller combinations suitable for shaping or conforming the substrate S2 as desired. The interlocking teeth on the rollers form corrugations on the nonwoven sheet that is passed between the rollers.

Figure 26B:
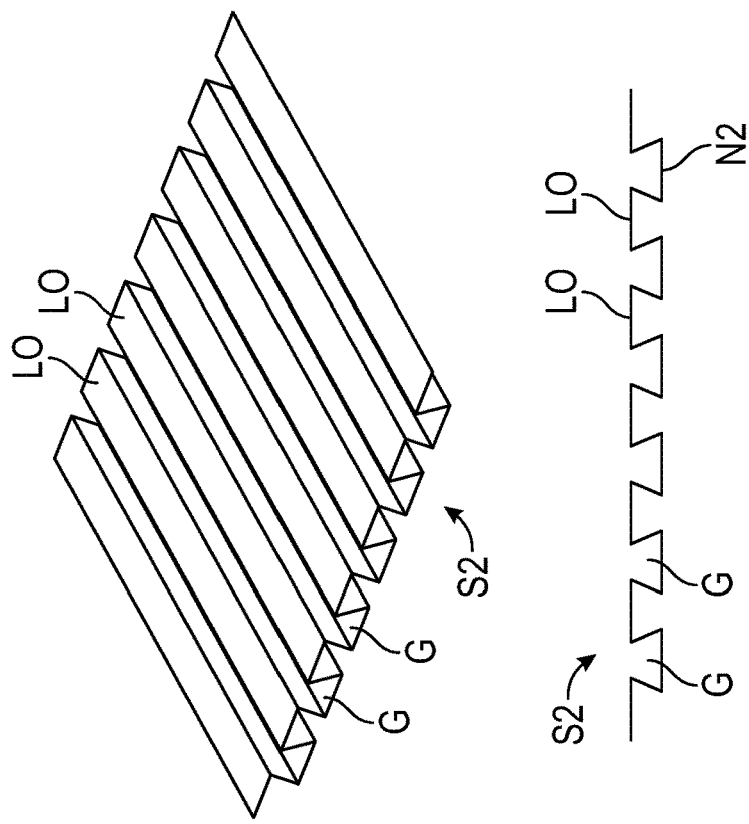
FIGS. 26A-26B are simplified illustrations, in perspective view, of a pre-conformed substrate for use in the making of an elastic core assembly, according to the present disclosure.
Figure 26A:
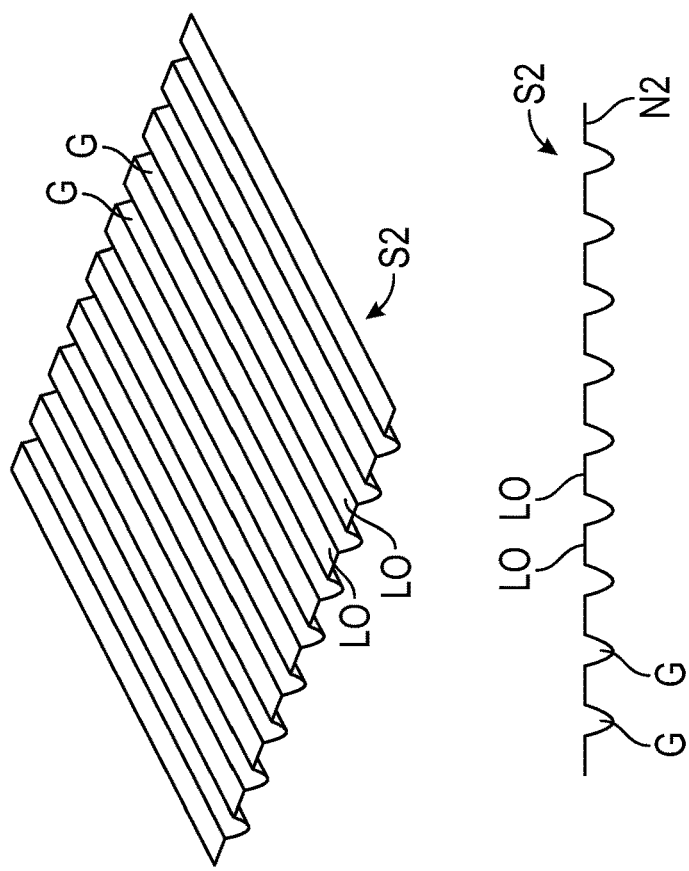
Figure 28:
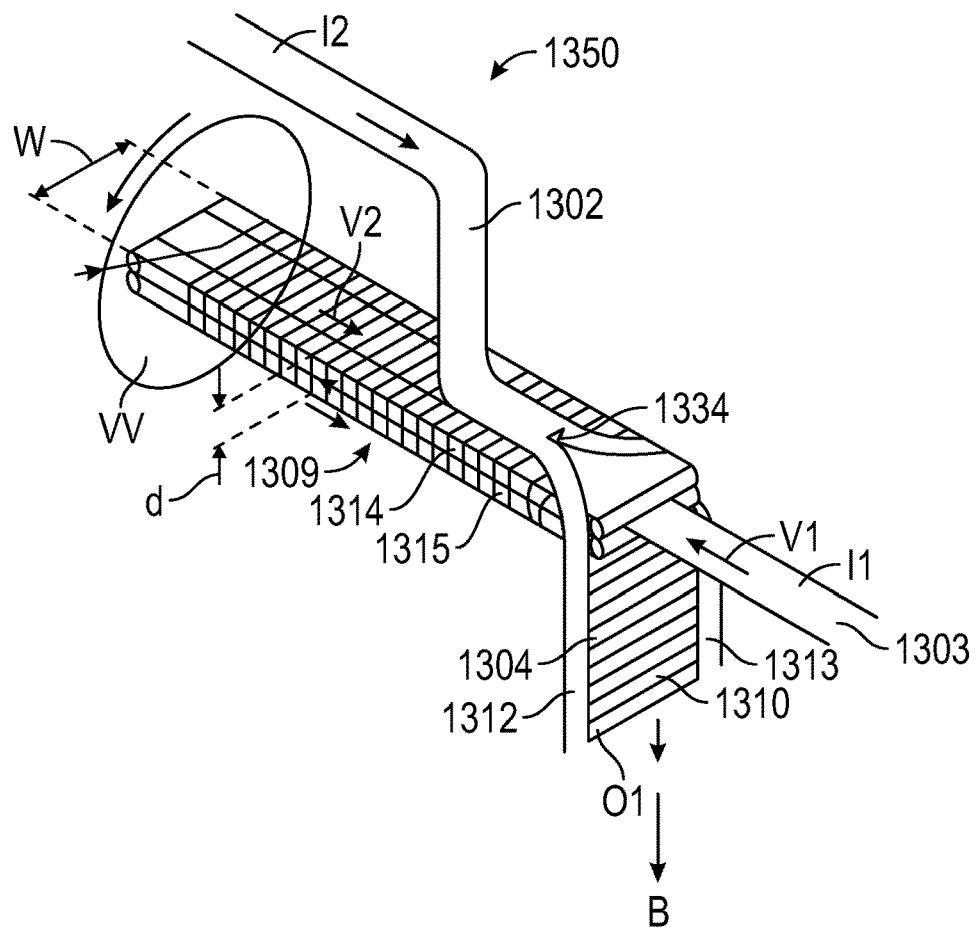
FIG. 28 is an isometric of a suitable sub-process and sub-system, to accompany the schematic of FIG. 24, for making an elastic composite for input to the process according to FIG. 24.
Figure 28A:
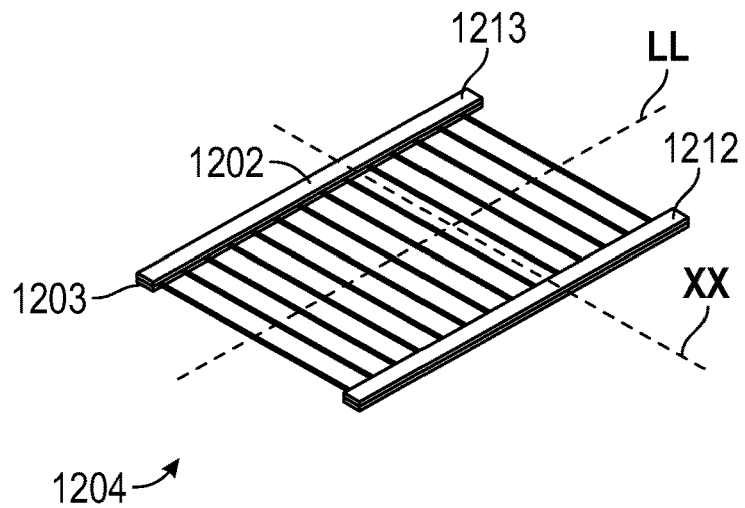
FIG. 28A is a simplified illustration of an elastic composite.

FIGS. 26A and 26B illustrate two suitable substrate S2 configurations. The substrate S2 in FIG. 26A may be configured preferably employing a conforming process such as that illustrated in FIG. 25. The substrate S2 in FIG. 26B may be configured preferably employing a similar conforming process wherein the surface of the nonwoven sheet is forcibly shaped. In the alternative, the substrate S2 of FIG. 26B may be pre-formed by a folding sub-process. Suitable folding sub-processes may be similar to those previously described herein. The substrate S2 is sourced from a nonwoven sheet that is conformed with a plurality of channels or grooves G in the machine or longitudinal direction. The substrate S2 also features a plateau or lane (SAP-free lane) L0 between the grooves G. Product design requirements may specify a desired depth of the grooves G and width of the lanes L0.

Referring again to FIG. 24, absorbent material such as superabsorbent particles may be supplied from hopper 2401 or set of SAP dispensers above the substrate S2, while the substrate S2 is moved forwardly in a generally horizontal disposition. The SAP particles S will fill the grooves G preferentially, while the SAP free lanes L0 are preferably maintained clear of SAP. A CD-arranged assembly of stretched filaments is simultaneously conveyed linearly toward and atop the moving SAP-filled substrate S2. A suitable assembly of elastic filaments is the elastic composite O1 produced by the process illustrated in FIG. 28 and described previously (in respect to FIG. 13 for example). The elastic composite O1 is overlaid on the SAP-filled nonwoven substrate S2, with the elastic filaments disposed in the cross-machine direction and across the SAP-filled grooves.

FIGS. 29A and 29B each depicts, in simplified form, an alternative system and process for making the elastic core assembly 200 (wherein like reference numerals are used to indicate like elements). In the system and process variation of FIG. 29A, the SAP dispenser 2401 is positioned downstream of engagement between the elastic composite O1 and substrate S2, and applies SAP S to the substrate S2 in laterally-spaced apart strips. The substrate S2 in this example may or may not be preformed or corrugated. If pre-formed with grooves, the strips of SAP are conveniently applied (e.g., dropped) into the grooves. Alternatively, strips of adhesives may be pre-applied on substrate S2 at laterally-spaced locations corresponding to SAP applications. In this way, the SAP strips are maintained in the designated lanes during manufacturing. In another variation, the SAP may be pre-mixed with adhesive (e.g. HMA) prior to the dispenser 2401 applying adhesive-laden absorbent material S onto the substrate S2 in the designated lanes.

Referring again to the embodiment of FIG. 29A, substrate S1 is pre-applied with strips of adhesive W as it is conveyed toward substrate S2 and elastic composite O1. Engagement between substrate S1 with substrate S2 and the elastics adheres these components together. Thereafter, tension on elastic composite O1 may be released and substrates S1 and S2 contracts with elastics E. Contraction creates excess material or slack in the substrates S1, S3, which results in expanding and shaping the desired capsules C. With substrate S2 and S1 in adherence, SAP is confined in the capsules C.

FIG. 29B depicts, in simplified form, an alternative system and process for making the elastic core assembly 200. In this system and process variation, the SAP dispenser 2401 is positioned downstream of engagement between the elastic composite O1 and substrate S2'. Further, an adhesive applicator is positioned upstream of engagement between the elastic composite O1 and Substrate S2, and applies spaced apart strips of adhesives on the substrate S2. Accordingly, when the elastic composite O1 engages with the substrate S2 in stretch mode, the elastic composite O1 adheres to the substrate S2. When elastic composite O1 is later released, it contracts the substrate S2 and, as pre-designed, creates downwardly urging void space with the excess material. In such variations, conforming or corrugating of the substrate S2 may not be needed for creating the capsules C. The SAP dispenser is positioned downstream of where the elastic composite is released and after the void spaces are formed. SAP can then be deposited onto the void spaces or capsules C.

Referring again to FIG. 29B, adhesive is applied on substrate S1 prior to engagement with substrate S2 and elastic composite O1. When continuous lines of adhesive are used and aligned with sap-free lanes on substrate S2, substrate S1 adheres to both elastic composite O1 and substrate S2. Elastic composite O1 may be maintained in the same stretched state after engagement with substrate S2 and during engagement with substrate S1. Upon release, elastic composite O1 contracts with both substrates S1, S2. The substrates S1, S2 relaxes and with the excess material, expands the profile of resulting capsule C. In a variation, elastic composite O1 is released to some degree after engagement with substrate S2 and substrate S1 is applied generally flatter and extended over SAP-filled and semi-contracted substrate S2 and semi-relaxed elastic composite O1. Upon full release of elastic composite O1, substrate S1 will contract and substrate S2 will contract further. The resulting profile of the elongated capsules C will project predominantly downward.

As reflected in the discussion above, the degree of release of elastic composite O2 at various points or stages in the process is a design variable that can be utilized to achieve different shapes of the capsules, different properties and different functionalities. The degree of slack on the substrates S1, S2 prior to engagement with elastic composite O1 is also design variable that may be varied in conjunction with the degree and process point of tension release (of elastic composite). Further yet, the pre-forming of substrate S1 and\or S2, including the creation of SAP-free lanes of specific dimensions, may also be useful in achieving design objectives.

Figure 30:
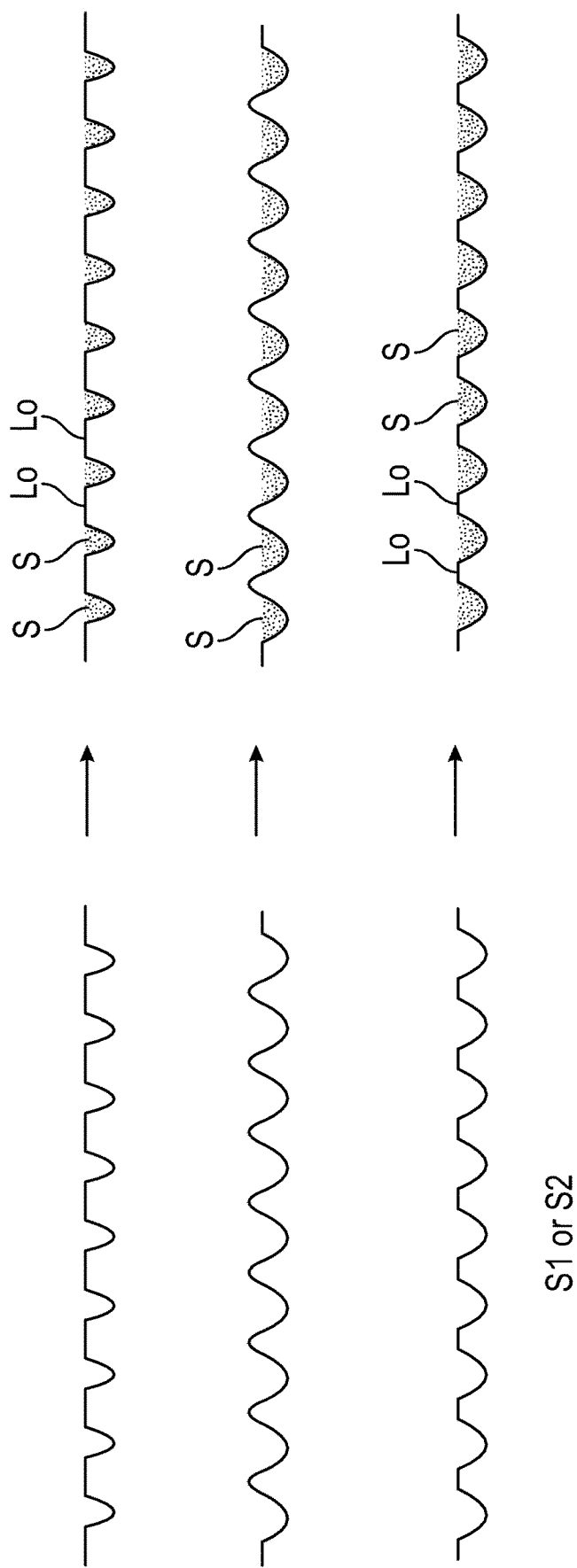
FIG. 30 are simplified illustrations of providing substrates of different configuration for receipt of absorbent material, according to the present disclosure.
Figures 31A, 31B:
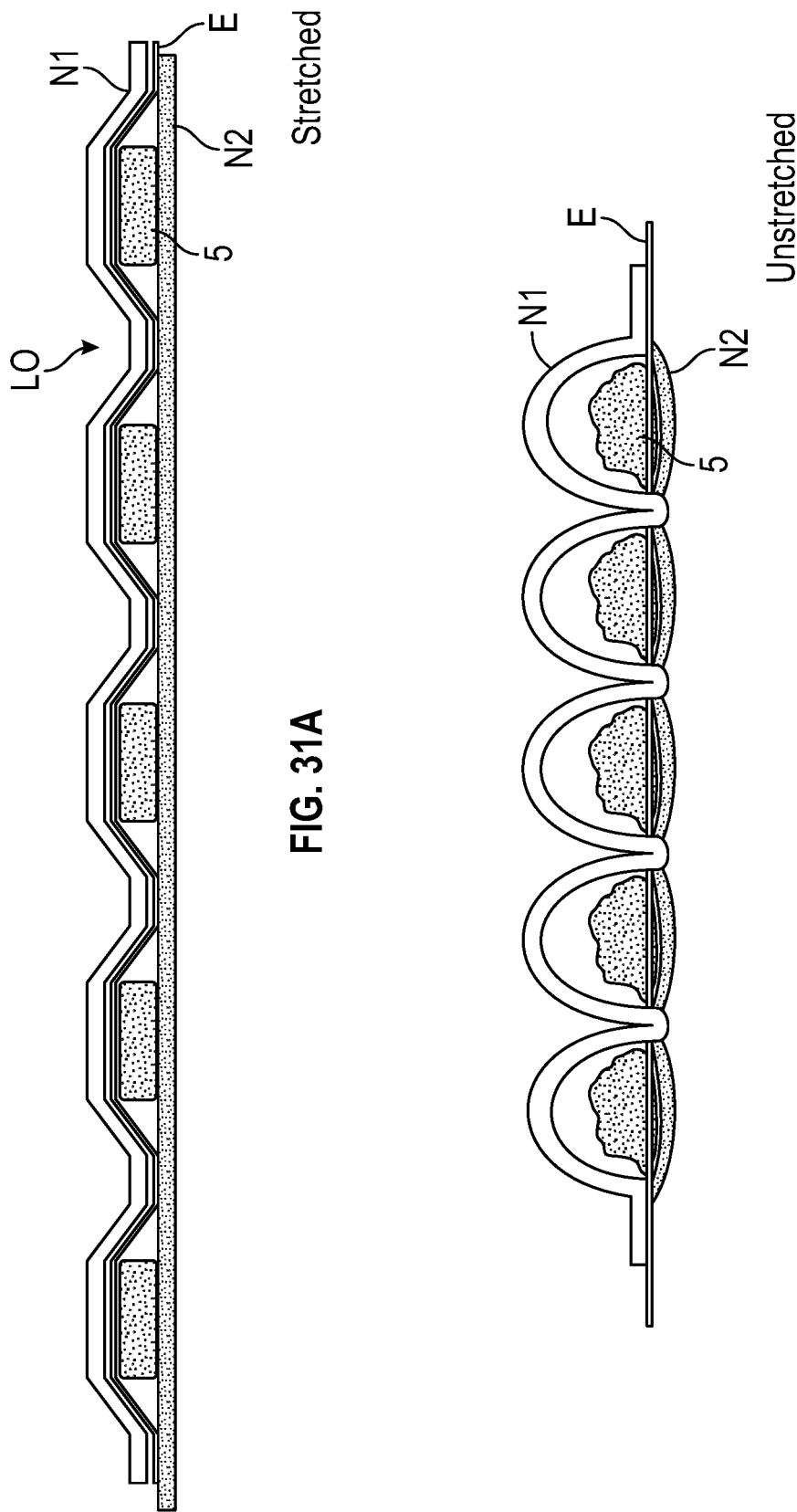
FIGS. 31A-31B are cross sectional views depicting the stretched and un-stretched configurations of exemplary elastic core assemblies, according to the present disclosure.

FIG. 30 illustrates three possible configurations of the substrates S1,S2 in making the elastic core assembly 201 (wherein like reference numerals are used to indicate like elements). The first configuration of substrate S1, S2 (on the top) is corrugated with wider SAP-free lanes L0, while the second or middle configuration of substrate S1, S2 is not equipped with any SP-free lanes. The third configuration of substrate S1, S2 is provided with intermediate size SAP-free lanes L0. The figures on the illustrate the varying SAP-loading capacities of the substrate. The first configuration has the wider SAP-free lanes but sacrifices SAP loading capacity.

FIGS. 30A and 30B provides additional simplified illustrations of an elastic core assembly 200 (wherein like reference numerals are used to indicate like elements) in the stretched state (FIG. 30A) and then the relaxed state (FIG. 30B). The embodiment of FIG. 30 provides another example of core assembly designs that achieve a desired dynamic and\or desired stretched and un-stretched configurations. Substrate S1 of nonwoven N2 is pre-applied with stripes of adhesives located to align with the SAP-free lanes L0 in substrate S2. The substrate S1 is then applied over the sub-assembly of substrate S1 and elastic composite O1, such that elastic filaments E are bonded in discrete points or areas to both the bottom and top sheets N1, N2. This merger forms the CD-stretchable absorbent composite 200 in its relaxed state (FIG. 30B). The extent of stretch in the composite 200 is determined by the amount of stretch in the elastic filaments when bonded and fixed to the nonwoven facing sheets N1, N2 from its relaxed state.

Figure 32A:
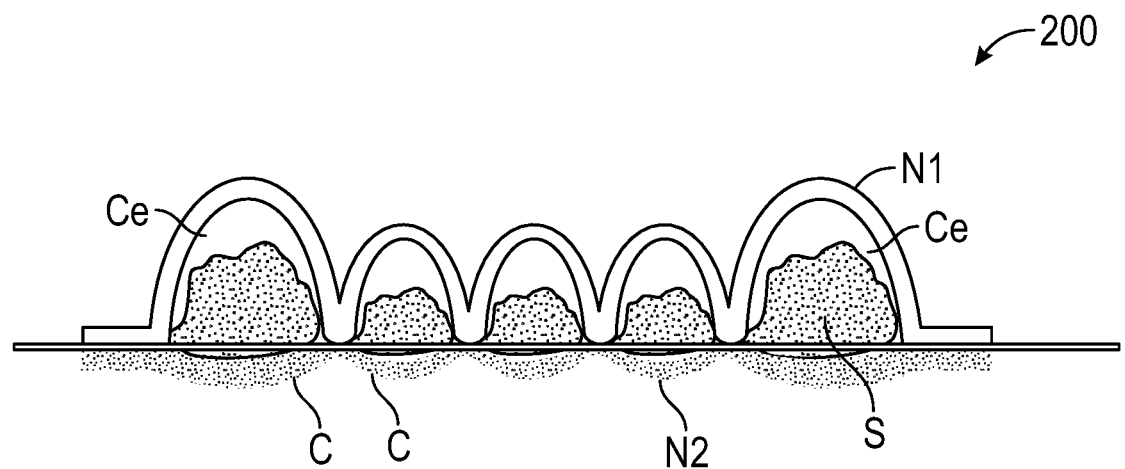
FIGS. 32A-32B are cross sectional views depicting alternate configurations of exemplary elastic core assemblies, according to the present disclosure.
Figure 32B:
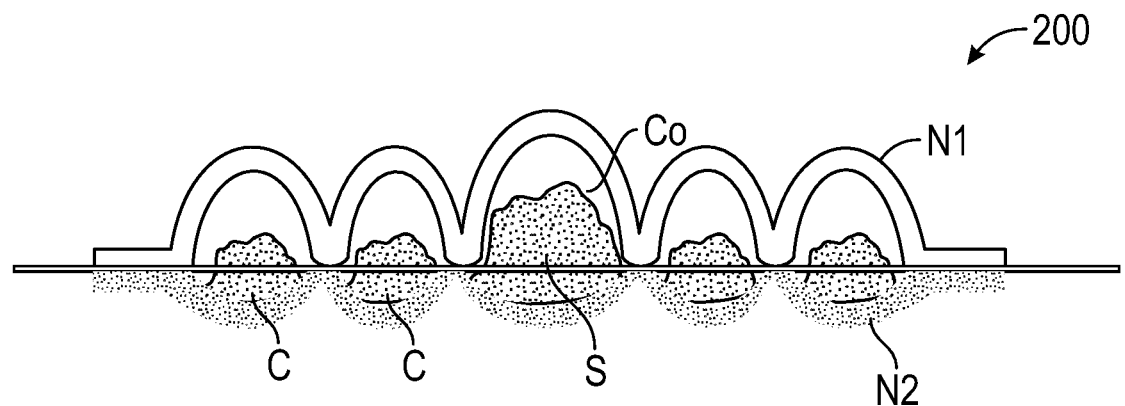

FIGS. 32A and 32B illustrate alternative embodiments of the elastic core assembly 200 wherein the spacing between spaced part bond points on the elastic E are varied to achieve a desired profile (wherein like reference numerals are used to indicate like elements). In FIG. 32A, greater elastic spacing proximate the side edges create larger capsules Ce. Such end capsules Ce preferably have greater SAP loading and advantageously present "bumpers" at the side edges effective at preventing side leakage. In FIG. 32B, greater spacing at the center provide for a larger capacity capsule Co. The center capsule Co is positioned to align with negative curvature regions of the wearer, as shown in the "baby waist contour" map of FIG. 33. In this instance, the large capsule C0 aligns to accommodate the negative curvature of the back. The elastic core assembly 200 of FIG.

32B may be modified and described as having large capsules Ce that align to accommodate a negative curvature regions on either side of the baby's tummy.

Bonding of the elastic filaments to the nonwoven may also be accomplished by adhesives that can be applied either to a nonwoven facing sheet or to the elastic filament prior to its inclusion into the composite, or via ultrasonics to entrap the filament in discrete points or areas on the nonwoven facings. When the adhesive is applied to the nonwoven facing sheet, it may be applied in an overall manner, as adhesive stripes or any other discrete pattern. When the adhesive is added to the elastic filaments, it may be applied over the length of each filament or on selected areas of each filament. In the instance where the adhesive is applied to the length of each filament, one option is to bond the elastic filament along its length to only one facing.

The two facings may consist of nonwovens with basis weights ranging from 8-120 grams/square meter (gsm) and of sheet density from 0.03-1.0 g/cc. Preferably, the facing sheet accepting the absorbent particles will be a bulky nonwoven for the purpose of fixing or immobilizing the particles. At least one of the facings will be hydrophilic, such hydrophilicity can be conferred by the inclusion of inherently wettable fibers such as rayon, synthetic fibers treated for wettability, or having the formed sheet treated for wettability such as surfactant addition, corona or plasma treatment. The use of a wettable substrate will allow enhanced liquid distribution due to wicking within the substrate that is supported by a favorable fiber wettability and an appropriate web density that can support capillary wicking. The web density and wettability combination can be determined using capillarity considerations (see for example, "Interfacial Forces in Aqueous Media, $2^{nd}$ ed, Carel J. van Oss, p. 140). (A substrate that can support a capillary rise of at least 1 cm is preferred).

The loading (amount) of absorbent material (primarily SAP) may be varied from tube to tube or capsule to/capsule. Additionally, the type of absorbent material or composition can be varied such as SAP retention capacity, absorption speed, average particle size, gel strength or permeability. These parameters change the absorption behavior of the absorbent aggregate such as speed of fluid lock-up, fluid flow rate and movement within the absorbent composite. Differences in these properties may be used to design specific flow patterns needed to enhance absorbent article performance. Other absorbent properties may also be varied through additives such as surfactants for wettability, odor control agents and the like.

Figure 34A:
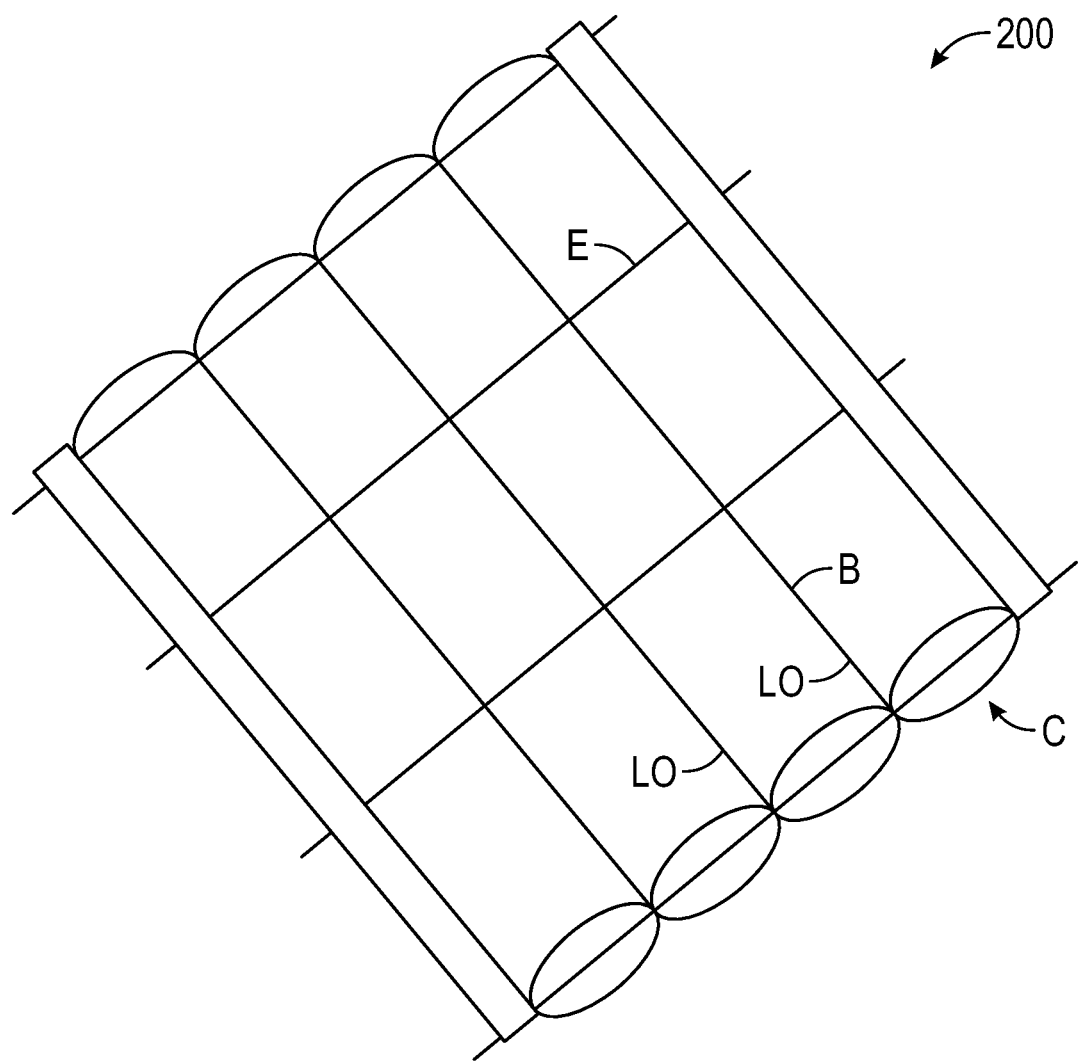
FIGS. 34A-34D are simplified illustrations, in perspective view, of alternate elastic core assemblies, according to the present disclosure.
Figure 34B:
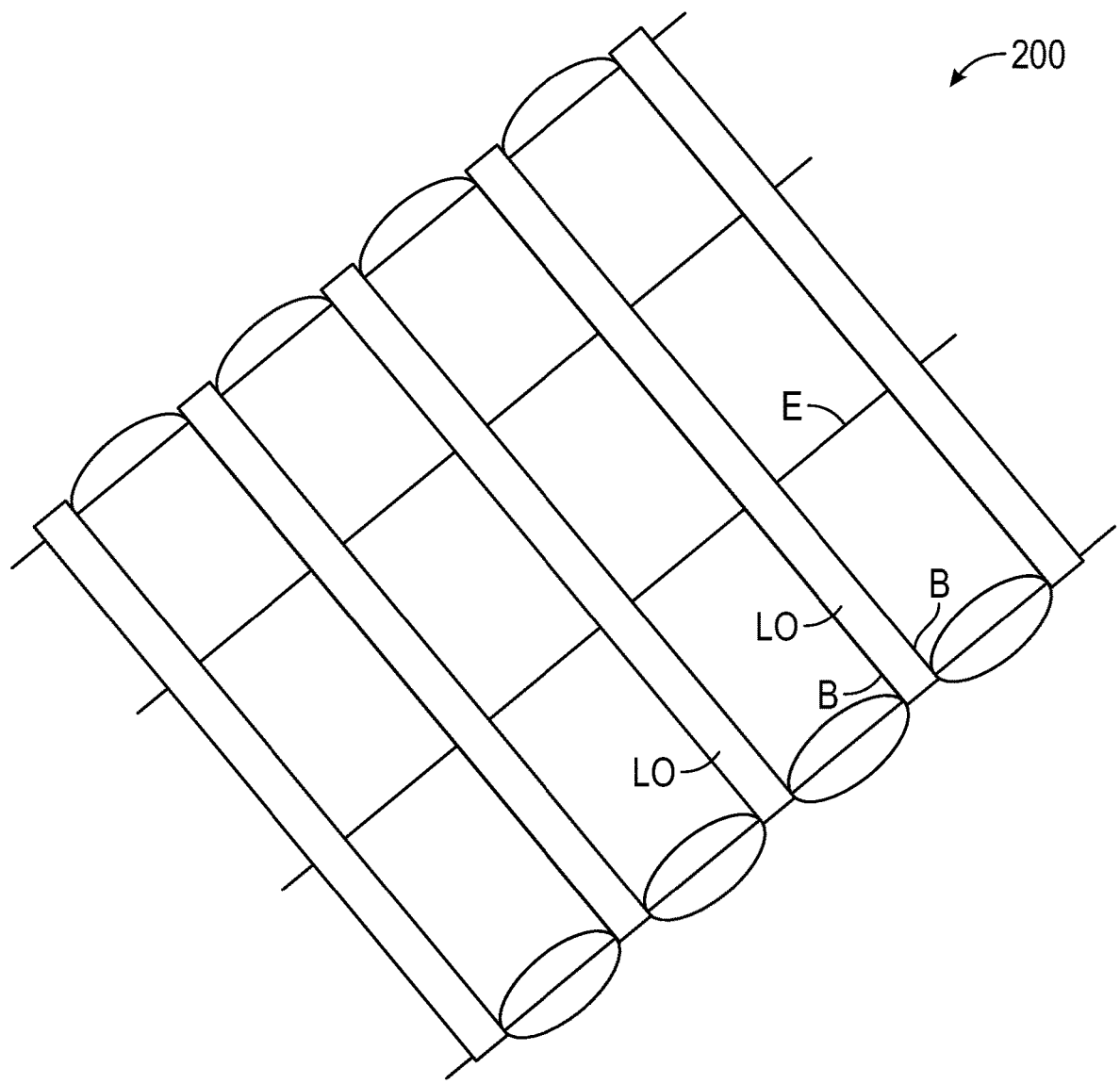

FIGS. 34A-34B illustrate design and functional variations achieved through modification of the SAP-free lanes L0 between capsules C and between bond edges to the elastics. In FIG. 34A, a narrow SAP-free lane is produced and a single bonding line is directed along the narrow lane to bond the substrates and elastics. In FIG. 34B, a wide SAP-Free lane is produced and two bonding lines are used to seal the gap between capsules. See also FIG. 21C and accompanying description. The width of the SAP-free lane is varied to produce SAP-free exterior channels of different widths. These channels may be utilized for enhanced fluid flow along the length of the channels. Alternatively, more absorbent particles/SAP may be deposited in these exterior channels to provide additional capacity. (See e.g., FIGS. 35 and 36). The, another nonwoven sheet may be added to cover the additional SAP stripes. This sheet can also provide ADL or topsheet functionalities. (See FIG. 35). A SAP constituent with properties different from the SAP within the capsules is preferred for the additional SAP stripe. For example, SAP with higher permeabilities and slower liquid absorption rates (vortex time) will have relatively faster liquid spreading, transport liquid to the SAP within the capsules in a controlled manner and enhance the overall performance of the composite.

The elastic absorbent composite may also be made as a finished absorbent insert for use as a removal absorbent core insert. The bottom nonwoven will be hydrophobic and can function as a breathable backsheet. The upper nonwoven facing can be a multifunctional material that can function both as an ADL and topsheet. Such a material may be made from dual layer nonwoven with a density gradient wherein one side is denser than the other. The denser side will function as the topsheet and the more open side will have ADL functionality (see FIG. 36).

Figure 34C:
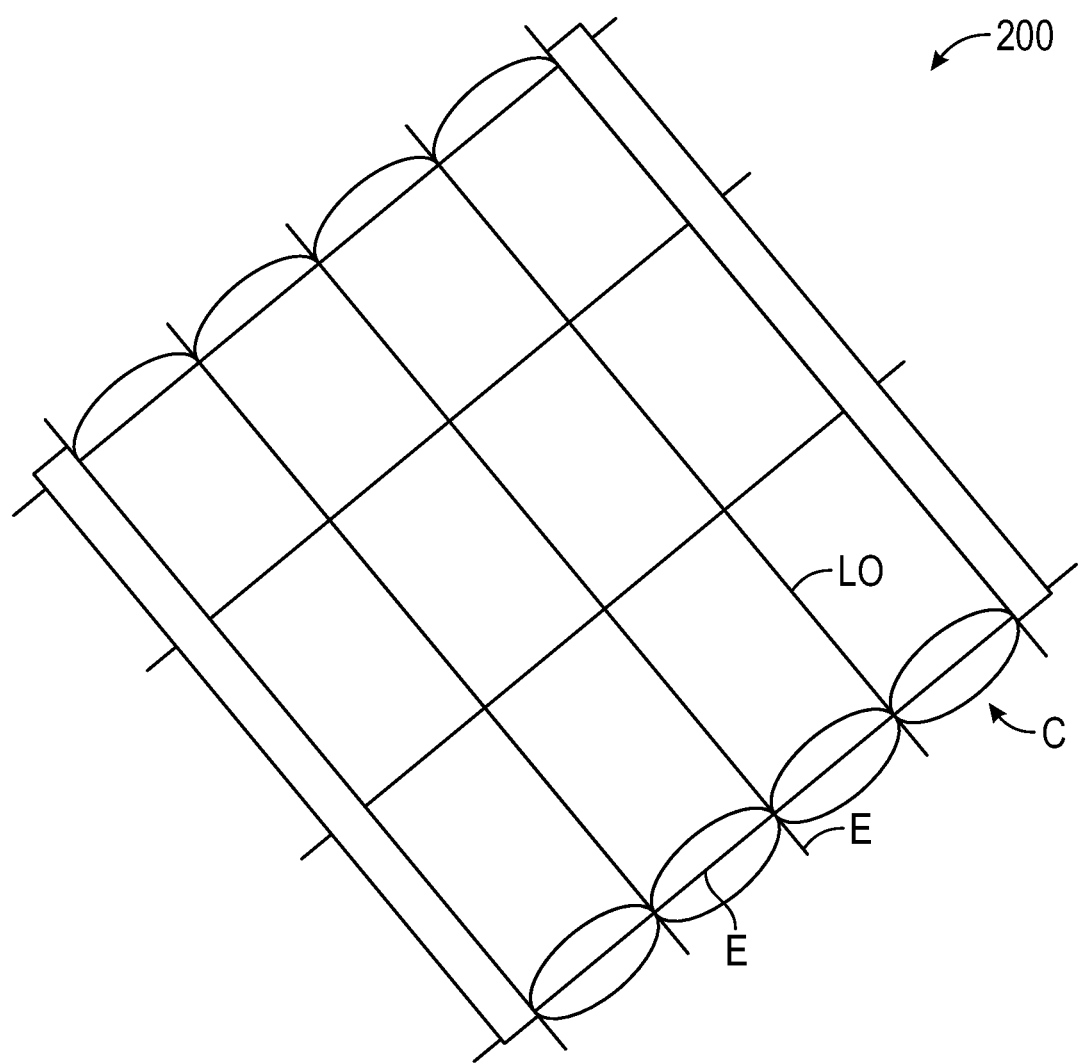
Figure 34D:
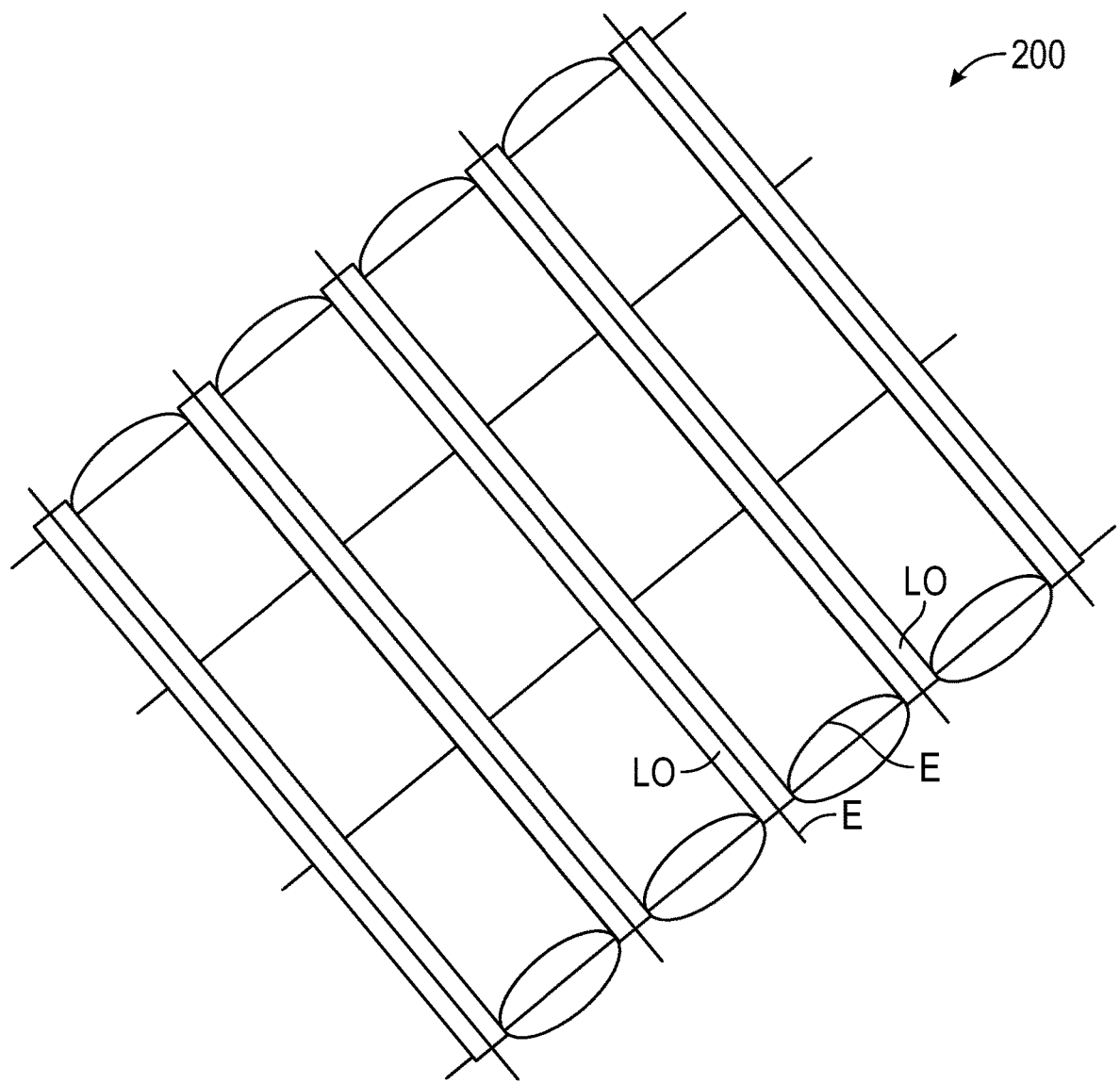
Figure 35:
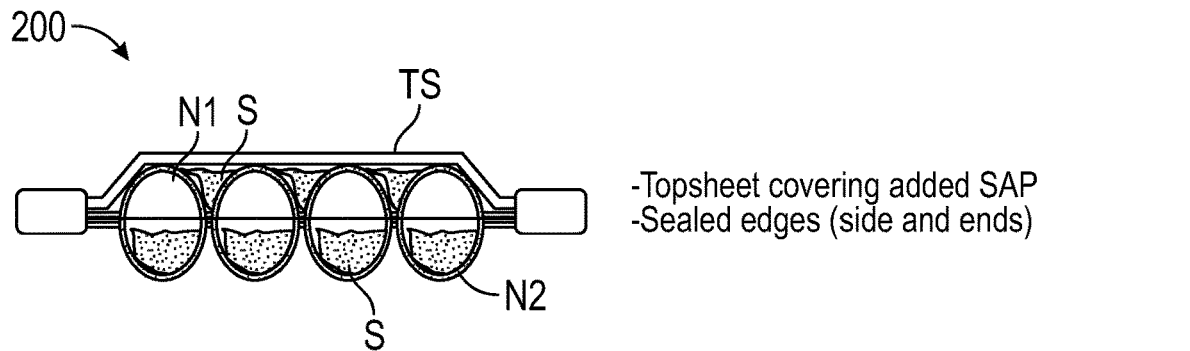
FIG. 35 are simplified illustrations, in cross-sectional view, of alternate elastic core assemblies with additional absorbent material-loading capacity, according to the present disclosure.
Figure 36:
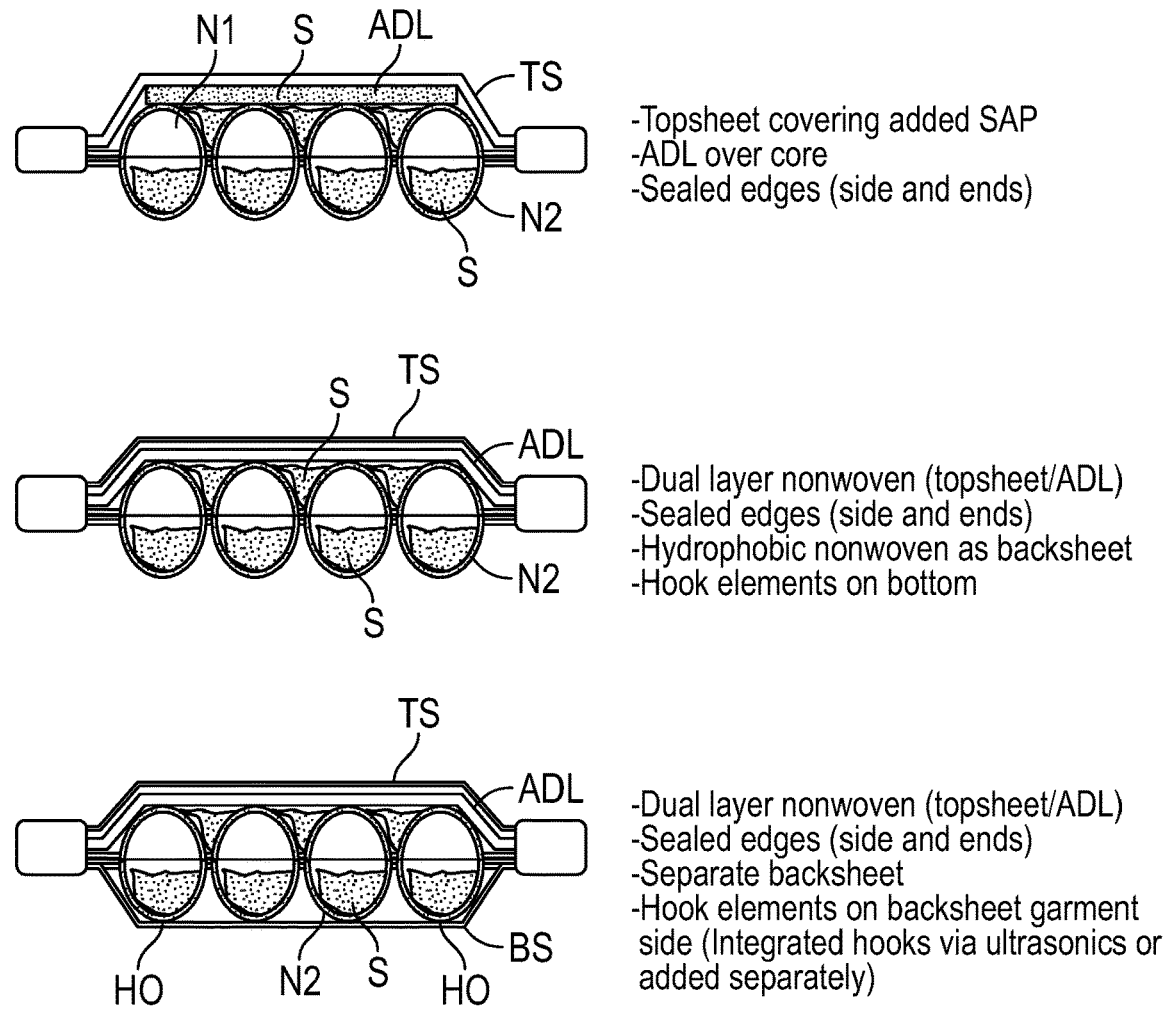
FIG. 36 are simplified illustrations, in cross-sectional view, of alternate elastic core assemblies incorporating additional absorbent material-loading capacity and a dual top cover layer, according to the present disclosure.

FIGS. 34C and 34D illustrate yet further embodiments of the elastic core assembly 200, with like reference numerals used indicate like reference numerals. In FIG. 34C, a narrow SAP-free lane is produced and a bonding line is applied to seal the lane. Then, at least in this embodiment, MD-elastics are conveniently applied over the same narrow SAP-free lane and over the bonding line, thereby creating a multi-directionally elasticized core assembly 200. The embodiment of FIG. 34D is a variation of the multi-directionally elasticized core assembly, wherein a wide SAP-free lane is utilized.

Other Design Variations

The simplified illustrations of FIG. 37 are used to illustrate additional design variations and applications, and to accompany the brief descriptions below, according to the present disclosure. The illustrations are of elasticized core assemblies, wherein like reference numerals are used to indicate like elements.

Figure 37A:
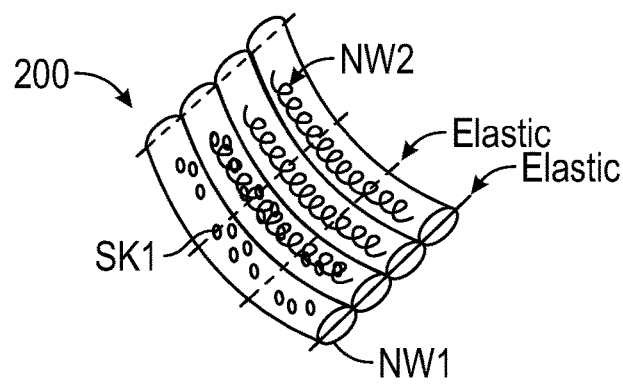
FIGS. 37A-37D are simplified illustrations, in perspective view, of alternate elastic core assemblies, according to the present disclosure.

FIG. 37A illustrates an elasticized core assembly 200 having a pronounced tubular shape. The configuration shown may be regarded as one of the basic designs of the elastic core assembly and applicable for many disposable absorbent applications. These applications include incorporation into a disposable absorbent diaper having an elasticized chassis, such as diaper 201 in FIGS. 2, 2A-2C.

Figure 37B:
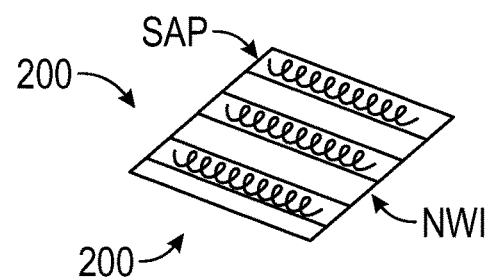

Referring to FIG. 37B, in an alternative embodiment, no folding or corrugating of the first nonwoven sheet is performed. Instead, the absorbent particles are deposited in stripes using vacuum assisted or striped material delivery. Examples of striped material delivery include the use of delivery tubes for depositing particles in stripes. Baffles could also be placed in the forming path of particle delivery to the substrate such that the particles are deposited in stripes.

Figure 37C:
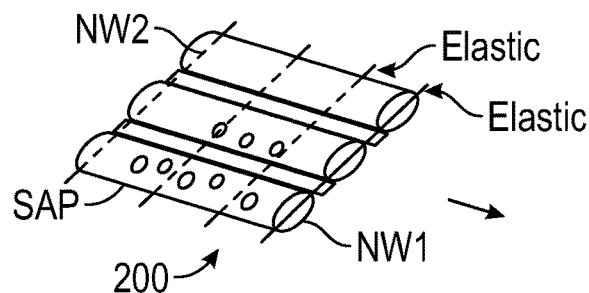

FIG. 37C illustrates an elasticized core assembly having a plurality of wide, SAP-free lane. The core assembly may be produced by using a wide elastic filament matrix.

Figure 37D:
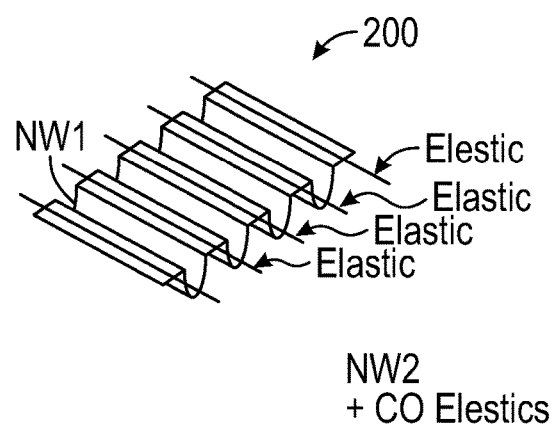
Figure 38:
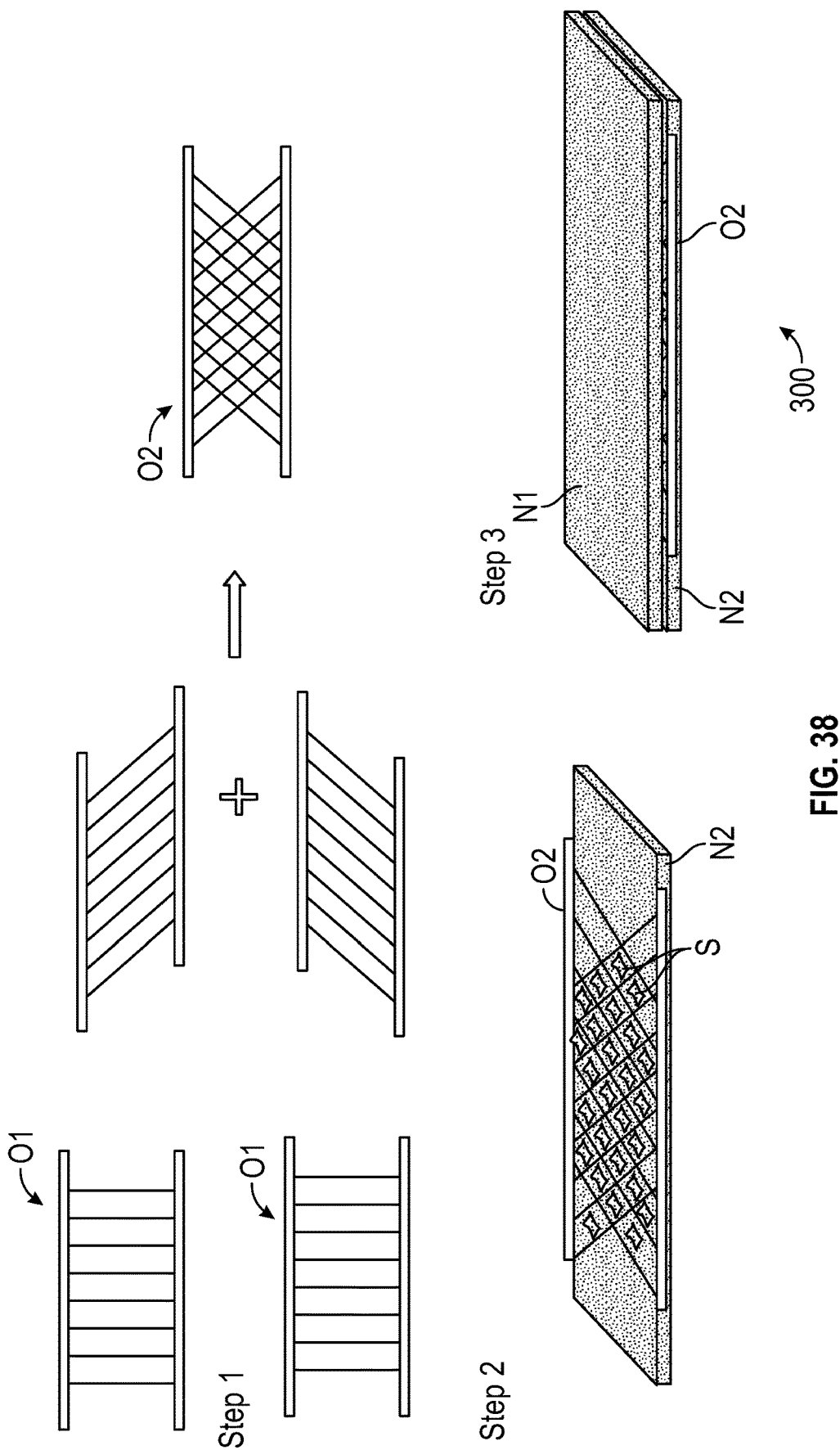
FIG. 38 is a process diagram of making a multi-directionally elastic core assembly, according to the present disclosure.

FIG. 37D illustrates an embodiment of the elastic core assembly, wherein the elastic construction includes elastic filaments introduced in the MD direction. Furthermore, at least one filament is disposed along the SAP-free lanes. Preferred bonding may employed as described above to produce an absorbent composite sandwich that is both MD and CD stretchable. FIG. 38 further illustrates a method of producing an multi-directional elastic core assembly 300, wherein like reference numerals are used to indicate like elements. In Step 1 according to FIG. 38, an elastic filament matrix O2 is produced from two cross-directional elastic composites O1 that are overlaid. One composite O1 is configured with the elastic filaments forming an angle between 0 and 90 degrees relative to the CD-axis and in the plane of the sheet (as in the process described above). The other composite O1 is preferably configured with the angle direction opposite that of the first. The angle shift can be produced by relative movement of one edge of the elastic composite with the opposing edge. The resulting elastic filament matrix O2 features crossed elastics with an oblique angle between filaments. See FIG. 38. The resulting elastic absorbent composite is both MD and CD stretchable.

As further shown in Step 2 of FIG. 38, adhesive may be applied to all elastic filament surfaces or in discrete area. Alternatively, adhesive may be applied on the substrate wholly or according to a pattern. The elastic matrix O2 the engages and bonds to the substrate. Then, SAP is applied in the cells outlined by the elastic matrix, before a top substrate or facing is applied over the SAP-filled matrix, as shown in Step 3 of FIG. 38.

It is also contemplated to create non-uniform elastication patterns along the longitudinal direction by various means such as:

1. Periodic variation in the elastic tension of the CD filaments by changing elongation prior to bonding the composite to the facings. For example, the filaments can be quickly extended
2. Initially uniform tension in the CD filaments followed by deactivation (ie. cutting) of selected filaments
3. Initially uniform tensions, but bonding to attach the elastic filaments to the facings is non-uniform An absorbent core with non-uniform shapes and profiled basis weights can be formed from a uniformly rectangular composite. For instance, an hourglass-shaped core with a higher basis weight and higher protrusion in the crotch area/target zone can be made. Similarly, the array of MD elastic filaments may also be introduced into the composite at different tensions and can cause the article to conform to preferred 3D configurations. For example, higher tensions along the side edges will result in a cup-shaped configuration which is advantageous for product fit. The interaction between non-uniform MD and CD elastication may also produce a variety of configurations that can result in fit and performance product advantages.

Figure 39:
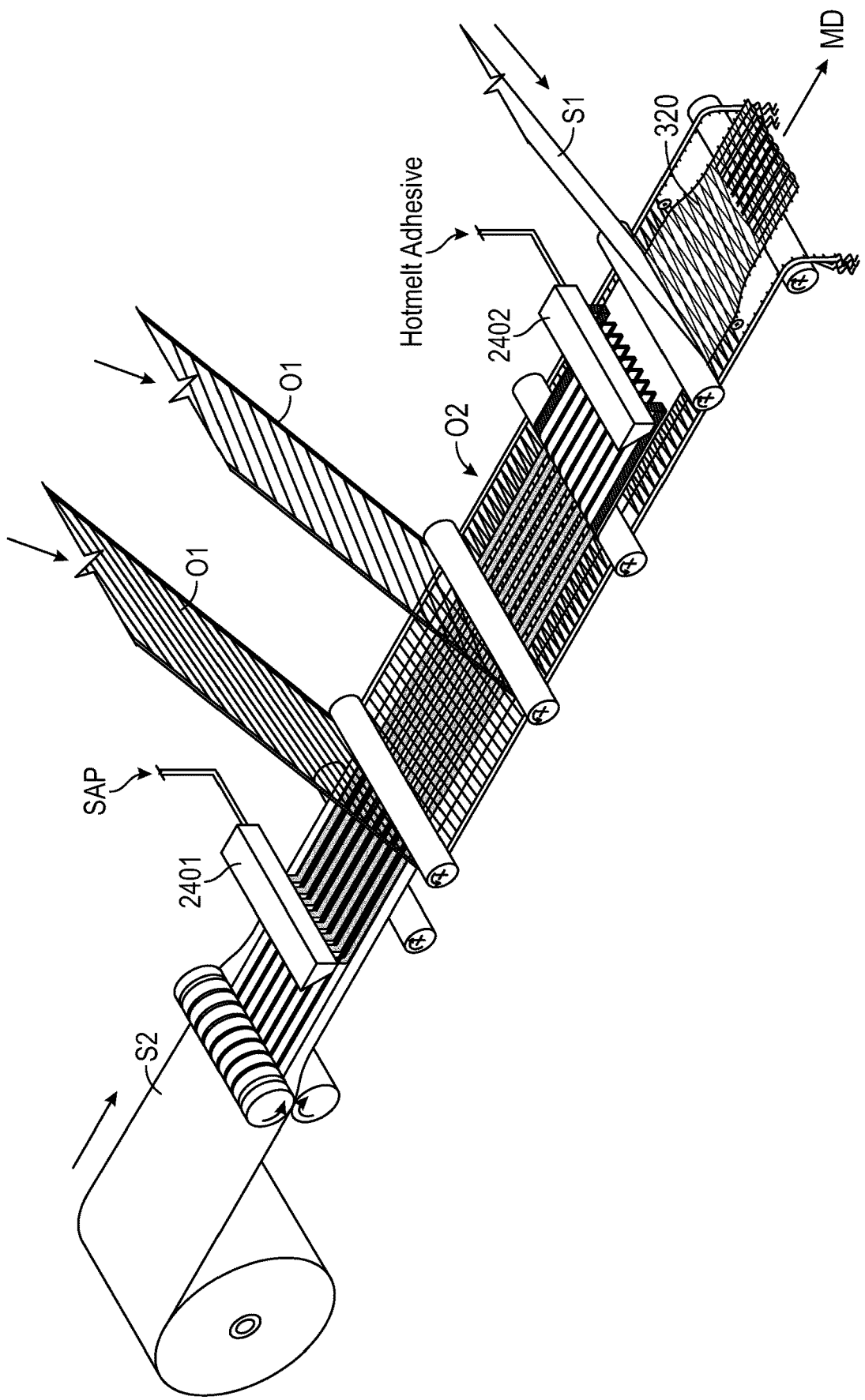
FIG. 39 is a simplified illustration and isometric of a system and a method for making a multi-directionally elastic core assembly according to the present disclosure.

FIG. 39 illustrates an exemplary system and process for making the absorbent core assembly 300 described above and in respect to FIG. 38 (wherein, in respect to FIGS. 24 and 38, like reference numerals are used to indicate like elements). The system in FIG. 39 may also be described as a modification of the system earlier described in respect to FIG. 24B.

Although the presently disclosed product, system and\or process and their advantages have been described in detail, it should be understood that various changes, substitutions and alterations can be made herein without departing from the spirit and scope of the disclosure and as defined by the appended claims. Moreover, the scope of the present disclosure is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim:

1. An elastic absorbent core assembly for incorporation into a disposable absorbent garment, the elastic absorbent core assembly comprising:
    a top material layer;
    a base material layer;
    an elastic construction sandwiched between the top layer and the base layer, the elastic construction including a plurality of spaced apart elastic elements each in the form of a strand having a length, wherein each strand is intermittently attached to at least one of the top layer and the base layer at spaced apart attachment points along the length of the strand such that attachment of the plurality of elastic strands with the top material layer or the base material layer at said attachment points form spaced apart ridges between pairs of spaced apart attachment points; and
    a plurality of populations of superabsorbent polymer particles each disposed between a pair of said ridges or between a ridge of the top or base layer on which the ridge is formed and the other of the top or base layers;
    wherein the top material layer and the base material layer are adhered to each other along bond lines, wherein the spaced apart attachment points are along the bond lines, and wherein the bond lines extend generally transverse to the elastic elements.

2. The elastic absorbent core assembly of claim 1, wherein said attachment points form spaced apart ridges extending transversely to the elastic strands and in coincidence with a line of spaced apart attachment points on a plurality of said elastic strands.

3. The elastic absorbent core assembly of claim 1, wherein the populations of superabsorbent polymer particles are disposed in spaces between the top layer and base layer.

4. The elastic absorbent core assembly of claim 3, wherein said spaces in which the superabsorbent materials are disposed extend transversely to said plurality of spaced apart elastic strands.

5. The elastic absorbent core assembly of claim 1, wherein void spaces are formed between said top and base layers coincident with said ridges, and wherein said populations of superabsorbent polymer particles are disposed in said void spaces.

6. The elastic absorbent core assembly of claim 5, wherein said ridges and said void spaces extend transversely across the plurality of spaced apart elastic strands.

7. The elastic absorbent core assembly of claim 5, wherein said void spaces are formed between said elastic strands and populations of superabsorbent polymer particles disposed in said void spaces form a plurality of spaced apart aggregates of superabsorbent particles.

8. The elastic absorbent core assembly of claim 1, wherein said elastic strands are adhered to the top layer or base layer in a stretched state and disposed in a relax state.

9. The elastic absorbent core assembly of claim 1, wherein the ridges are coincident with non-adhered areas between the top material layer and the base material layer.

10. The elastic absorbent core assembly of claim 1, wherein the top material layer and the base material layer are continuously attached to each other.

11. The elastic absorbent core assembly of claim 1, wherein the elastic absorbent core assembly has a first longitudinal edge, a second longitudinal side edge, a first laterally extending edge, and a second laterally extending edge, wherein the longitudinal side edges are longer than the laterally extending edges, wherein the elastic absorbent core assembly has a longitudinal centerline extending from the first laterally extending edge to the second laterally extending edge and parallel with the longitudinal side edges, and wherein the elastic elements extend transverse to the longitudinal centerline.

12. The elastic absorbent core assembly of claim 11, wherein the base material layer comprises grooves, and wherein the grooves extend parallel with the longitudinal centerline.

13. An elastic absorbent core assembly for use in manufacturing disposable absorbent garments, the elastic absorbent core assembly comprising
a top nonwoven layer;
a base nonwoven layer;
a plurality of spaced apart elastic elements bonding with the top layer and the base layer at bond sites, wherein the top and base layers are spaced apart from each other between said bond sites to form encapsulating spaces therebetween; and
absorbent material located in said encapsulating spaces, wherein said encapsulating spaces include a void space above and below said elastics.

14. The elastic absorbent core assembly of claim 13, wherein said bond sites are spaced apart bond sites.

15. The elastic absorbent core assembly of claim 13, wherein said top and base layers are bonded along bond lines that intersect said spaced apart bond sites.

16. The elastic absorbent core assembly of claim 13, wherein said nonwoven layers form, from said encapsulating spaces, elongated capsules of superabsorbent material.

17. The elastic absorbent core assembly of claim 16, wherein said elastic elements are elastic strands disposed transversely to said elongated capsules.

18. The elastic absorbent core assembly of claim 17, wherein said elastic elements are elastic strands disposed transversely to said elongated capsules and bonded to said top and base layers in a stretched state, such that said elongated capsules are provided by said nonwoven layers and said elastic strands in relaxed state.

19. The elastic absorbent core assembly of claim 13, wherein one of the top layer and base layer is a bulky nonwoven layer.

20. The elastic absorbent core assembly of claim 13, wherein said absorbent material includes superabsorbent particles mixed with hot melt particles.

21. The elastic absorbent core assembly of claim 13, wherein said encapsulating spaces are generally elongated and closed off from one another along continuous bond lines mutually securing said nonwoven layers and said elastics.

22. The elastic absorbent core assembly of claim 13, wherein each elongated capsule is open to and in fluid communication with an adjacent elongated capsule.

23. The elastic absorbent core assembly of claim 13, wherein the elastic absorbent core assembly has a first longitudinal edge, a second longitudinal side edge, a first laterally extending edge, and a second laterally extending edge, wherein the longitudinal edges are longer than the laterally extending edges, wherein the elastic absorbent core assembly has a longitudinal centerline extending from the first laterally extending edge to the second laterally extending edge and parallel with the longitudinal side edges, and wherein the elastic elements extend transverse to the longitudinal centerline.

24. A disposable absorbent article comprising:
a chassis having a first longitudinal end edge, a second longitudinal end edge, and a longitudinal centerline that extends through the chassis; and
an elastic absorbent core assembly supported on said chassis, the elastic absorbent core assembly including a top nonwoven layer, a base nonwoven layer, a plurality of spaced apart elastic elements bonding with at least one of the top nonwoven layer and the base nonwoven layer along bond lines extending transversely to said elastic elements, wherein the top and base nonwoven layers are spaced apart to form encapsulating spaces between said bond lines, wherein said elastic elements extend transverse to and perpendicular to said longitudinal centerline; and
absorbent material located in said encapsulating spaces.

25. The disposable absorbent article of claim 24, wherein said elastic elements are attached to said nonwoven layers at a plurality of spaced apart bond points, and wherein said encapsulating space is formed between each of a plurality of pairs of said spaced apart bond points, said bond lines being formed by alignment of said spaced apart bond points.

26. The disposable absorbent article of claim 25, wherein said encapsulating space is an elongated encapsulating space directed transversely to and through said spaced apart elastic elements, and wherein said encapsulating space contains superabsorbent material.

27. The disposable absorbent article of claim 26, wherein said elastic absorbent core assembly is elasticized in both the cross machine direction and machine direction.

28. An elastic absorbent core assembly for incorporation into a disposable absorbent garment, the elastic absorbent core assembly comprising:
a top material layer;
a base material layer;
an elastic construction sandwiched between the top layer and the base layer, the elastic construction including a plurality of spaced apart elastic elements each in the form of a strand having a length, wherein each strand is intermittently attached to at least one of the top layer and the base layer at spaced apart attachment points along the length of the strand such that attachment of the plurality of elastic strands with the top material layer or the base material layer at said attachment points form spaced apart ridges between pairs of spaced apart attachment points; and
a plurality of populations of superabsorbent polymer particles each disposed between a pair of said ridges or between a ridge of the top or base layer on which the ridge is formed and the other of the top or base layer;
wherein spaced apart ridges are formed in the top material layer between pairs of spaced apart attachment points.

29. The elastic absorbent core assembly of claim 28, wherein each strand is intermittently attached to the top layer and the base layer at spaced apart attachment points along the length of the strand such that attachment of the plurality of elastic strands with the top material layer at said attachment points form said spaced apart ridges in the top material layer between pairs of spaced apart attachment points, and such that attachment of the plurality of elastic strands with the base material layer at said attachment points form spaced apart ridges in the base material layer between pairs of spaced apart attachment points.

* * * * *

UNITED STATES PATENT AND TRADEMARK OFFICE
CERTIFICATE OF CORRECTION

PATENT NO. : 10,799,400 B2
APPLICATION NO. : 15/360776
DATED : October 13, 2020
INVENTOR(S) : Eugenio G. Varona and Andrew Christopher Wright It is certified that error appears in the above-identified patent and that said Letters Patent is hereby corrected as shown below:

In the Specification

Column 5, Line 46, delete "an" and insert --a--.
Column 21, Line 43, delete "illustrate" and insert --illustrates--.
Column 22, Line 31, delete "illustrates" and insert --illustrate--.
Column 26, Line 35, delete "provides" and insert --provide--.

In the Claims

Column 30, Line 7, insert --material-- after the word "top".
Column 30, Line 8, insert --material-- after the word "base".
Column 30, Line 11, insert --material-- after the word "top".
Column 30, Line 12, insert --material-- after the word "base".
Column 30, Line 20, insert --material-- after the word "base".
Column 30, Line 21, insert --material-- after the word "base".
Column 30, Line 34, insert --material-- after the word "top".
Column 30, Line 34, insert --material-- after the word "base".
Column 30, Line 40, insert --material-- after the word "base".
Column 30, Line 53, insert --material-- after the word "top".
Column 30, Line 53, insert --material-- after the word "base".
Column 31, Line 15, insert --nonwoven-- after the word "top".
Column 31, Line 15, insert --nonwoven-- after the word "base".
Column 31, Line 16, insert --nonwoven-- after the word "base".
Column 31, Line 26, insert --nonwoven-- after the word "base".
Column 31, Line 37, insert --nonwoven-- after the word "base".
Column 31, Line 41, insert --nonwoven-- after the word "top".
Column 31, Line 41, insert --nonwoven-- after the word "base".
Column 32, Line 35, insert --material-- after the word "top".
Column 32, Line 36, insert --material-- after the word "base".
Column 32, Line 39, insert --material-- after the word "top".

Signed and Sealed this
Twenty-first Day of March, 2023

Katherine Kelly Vidal
*Director of the United States Patent and Trademark Office*

CERTIFICATE OF CORRECTION (continued)
U.S. Pat. No. 10,799,400 B2

Column 32, Line 40, insert --material-- after the word "base".
Column 32, Line 48, insert --material-- after the word "base".
Column 32, Line 49, insert --material-- after the word "base".
Column 32, Line 53, insert --material-- after the word "top".
Column 32, Line 54, insert --material-- after the word "base".